(12) United States Patent
Song et al.

(10) Patent No.: US 7,622,919 B2
(45) Date of Patent: Nov. 24, 2009

(54) NUCLEAR MAGNETIC RESONANCE MEASUREMENT TECHNIQUES IN NON-UNIFORM FIELDS

(75) Inventors: Yi-Qiao Song, Ridgefield, CT (US);
Nicolas Caudal, Le Chesnay (FR);
Martin Hürlimann, Newton, MA (US);
Eric E. Sigmund, New York, NY (US)

(73) Assignee: Schlumberger Technology Corporation, Ridgefield, CT (US)

( * ) Notice: Subject to any disclaimer, the term of this patent is extended or adjusted under 35 U.S.C. 154(b) by 2 days.

(21) Appl. No.: 11/496,557

(22) Filed: Jul. 31, 2006

(65) Prior Publication Data
US 2008/0024128 A1    Jan. 31, 2008

(51) Int. Cl.
*G01V 3/00* (2006.01)
(52) U.S. Cl. .................................... 324/307
(58) Field of Classification Search ......... 324/300–322; 600/410–435; 382/128–134, 276–308; 702/5–14, 702/19–32, 57–80
See application file for complete search history.

(56) References Cited

U.S. PATENT DOCUMENTS

| | | | | |
|---|---|---|---|---|
| 4,531,093 | A | * | 7/1985 | Rollwitz et al. ............. 324/300 |
| 4,902,973 | A | * | 2/1990 | Keren ......................... 324/312 |
| 5,204,625 | A | * | 4/1993 | Cline et al. ................. 324/306 |
| 6,512,371 | B2 | | 1/2003 | Prammer |
| 6,665,616 | B2 | * | 12/2003 | Mickael ........................... 702/8 |
| 6,686,738 | B2 | * | 2/2004 | Edwards ...................... 324/303 |
| 6,795,330 | B2 | | 9/2004 | Demange et al. |
| 6,850,060 | B2 | * | 2/2005 | Song et al. ................... 324/303 |
| 6,856,134 | B1 | * | 2/2005 | Reeder et al. ................ 324/309 |
| 6,883,702 | B2 | * | 4/2005 | Hurlimann et al. .......... 324/303 |
| 6,903,547 | B2 | * | 6/2005 | Sigal et al. ................... 324/303 |
| 6,956,371 | B2 | * | 10/2005 | Prammer ..................... 324/303 |
| 6,972,564 | B2 | | 12/2005 | Chen et al. |
| 7,171,257 | B2 | * | 1/2007 | Thomson ..................... 600/427 |

OTHER PUBLICATIONS

Carr, H.Y. et al., Effects of Diffusion on Free Precession in Nuclear Magnetic Resonance Experiments, Physical Review, 1954, pp. 630-638, vol. 94, No. 3.

Edzes, H.T., An Analysis of the Use of Pulse Multiplets in the Single Scan Determination of Spin-Lattice Relaxation Rates, Journal of Magnetic Resonance, 1975, pp. 301-313, vol. 17.

(Continued)

*Primary Examiner*—Brij B. Shrivastav
*Assistant Examiner*—Dixomara Vargas
(74) *Attorney, Agent, or Firm*—James McAleenan; Jody Lynn DeStefanis; Dale Gaudier

(57) ABSTRACT

Methods and pulse sequences for facilitating nuclear magnetic resonance (NMR) measurements in grossly inhomogeneous fields. Methods and pulse sequences according to the invention may be used to accurately measure variables such as transverse relaxation time, longitudinal relaxation time, and diffusion, without the need for data at long recovery time, thereby allowing for faster measurements. In addition, methods and pulse sequences according to embodiment of the invention may allow simultaneous encoding of information in both the amplitude and the shape of echoes, so as to allow a single-shot measurement of multiple variables, e.g., both transverse relaxation time (from the decay of echo amplitudes) and longitudinal relaxation time (from the echo shape). CPMG detection may be used to overcome the often limited signal-to-noise ratio in grossly inhomogeneous fields.

15 Claims, 44 Drawing Sheets

OTHER PUBLICATIONS

Freeman, R., et al., Fourier Transform Study of NMR Spin-Lattice Relaxation by "Progressive Saturation", The Journal of Chemical Physics, 1971, 3367-3377, vol. 54, No. 8.

Freeman, R., et al., An Adaptive Scheme for Measuring NMR Spin-Lattice Relaxation Times, Journal of Magnetic Resonance, 1972, pp. 82-98, vol. 7.

Gupta, R.K., et al., A Modified Fast Inversion-Recovery Technique for Spin-Lattice Relaxation Measurements, Journal of Magnetic Resonance, 1980, pp. 447-452, vol. 38.

Hsu, J.-J., et al., Spin-lattice relaxation and a fast T1-map acquisition method in MRI with transient-state magnetization, Journal of Magnetic Resonance, 2004, pp. 270-278, vol. 169.

Hurlimann, M.D., Carr-Purcell Sequences with Composite Pulses, Journal of Magnetic Resonance, 2001, pp. 109-123, vol. 152.

Hurlimann, M.D., Diffusion and Relaxation Effects in General Stray Filed NMR Experiments, Journal of Magnetic Resonance, 2001, pp. 367-378, vol. 148.

Hurlimann, M.D., Encoding of diffusion and T1 in the CPMG echo shape: Single-shot D and T1 measurements in grossly inhomogeneous fields, Journal of Magnetic Resonance, 2006, pp. 114-129, vol. 184.

Hurlimann, M.D., et al., Spin Dynamics of Carr-Purcell-Meiboom-Gill-like Sequences in Grossly Inhomogeneous B0 and B1 Fields and Application to NMR Well Logging, Journal of Magnetic Resonance, 2000, pp. 120-135, vol. 143.

Hurlimann, M.D., et al. The diffusion-spin relaxation time distribution function as an experimental probe to characterize fluid mixtures in porous media, Journal of Chemical Physics, 2002, pp. 10223-10232, vol. 117, No. 22.

Kaiser, R., et al., Diffusion and field-gradient effects in NMR Fourier spectroscopy, The Journal of Chemical Physics, 1974, pp. 2966-2979, vol. 60, No. 8.

Kingsley, P.B., Methods of Measuring Spin-Lattice (T1) Relaxation Times: An Annotated Bibliography, Concepts in Magnetic Resonance, 1999, pp. 243-276, vol. 11, No. 4.

Loening, N.M., et al., Single-scan longitudinal relaxation measurements in high-resolution NMR spectroscopy, Journal of Magnetic Resonance, 2003, pp. 321-328, vol. 164.

Look, D.C., et al., Time Saving in Measurement of NMR and EPR Relaxation Times, The Review of Scientific Instruments, 1970, pp. 250-251, vol. 41, No. 2.

Meiboom, S., et al., Modified Spin-Echo Method for Measuring Nuclear Relaxation Times, The Review of Scientific Instruments, 1958, pp. 688-691, vol. 29, No. 8.

Sezginer, A., et al., Very Rapid Simultaneous Measurement of Nuclear Magnetic Resonance Spin-Lattice Relaxation Time and Spin-Spin Relaxation Time, Journal of Magnetic Resonance, 1991, pp. 504-527, vol. 92.

Sigmund, E.E., et al., Rapid T1 measurement via decay-recovery decomposition: Applications in fringe field and distributed relaxation experiments, Solid State Nuclear Magnetic Resonance, 2006, pp. 232-241, vol. 29.

Song, Y.-Q, et al., A one-shot method for measurement of diffusion, Journal of Magnetic Resonance, 2004, pp. 136-148, vol. 170.

Song, Y.-Q., et al., T1-T2 Correlation Spectra Obtained Using a Fast Two-Dimensional Laplace Inversion, Journal of Magnetic Resonance, 2002, pp. 261-268, vol. 154.

S. Sykora, et al., Null-Biased Fast-Field-Cycling Sequences, 4th Conference on FC NMR relaxometry, 2005, Poster—p. 24.

Tang, X.-P., et al., A novel nuclear spin-lattice relaxation filter for separating the free and absorbed water in a matrix of titanate nanotubes, Chemical Physical Letters, 2004, pp. 456-460, vol. 399.

Ungersma, S.E., et al., MR Imaging with T1 Dispersion Contrast, Proceedings International Society of Magnetic Resonance in Medicine, 2004, p. 179, Vol. 11.

Redpath et al., Magnetic resonance image synthesis from an interleaved saturation recovery/inversion recovery sequence, British Journal of Radiology, vol. 61, 1988, pp. 619-624.

\* cited by examiner

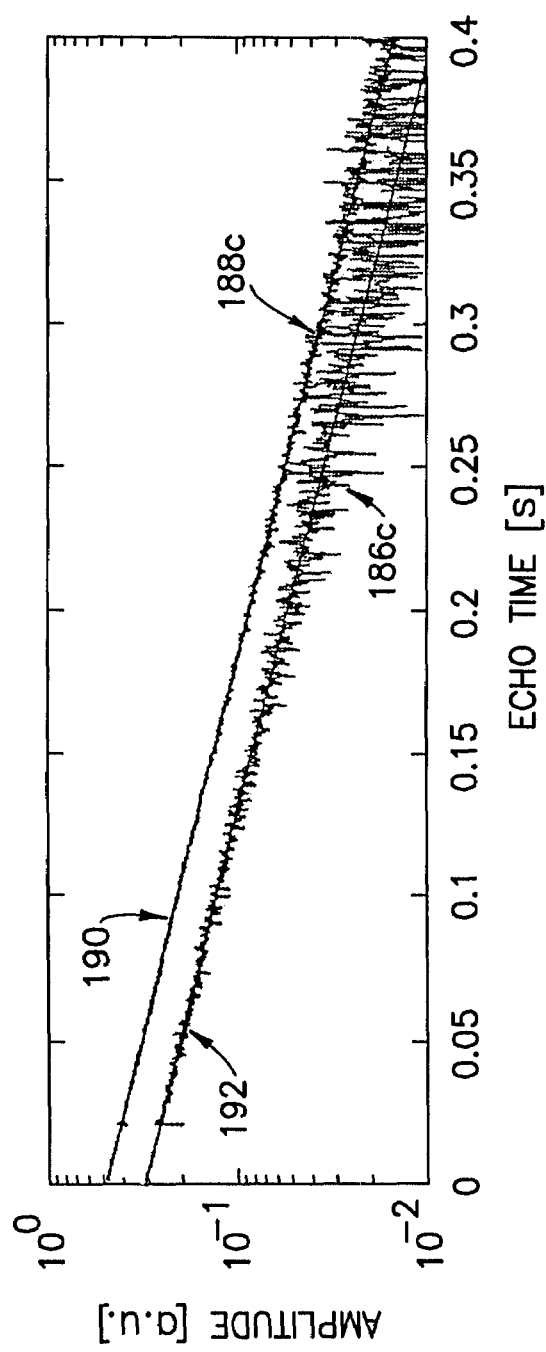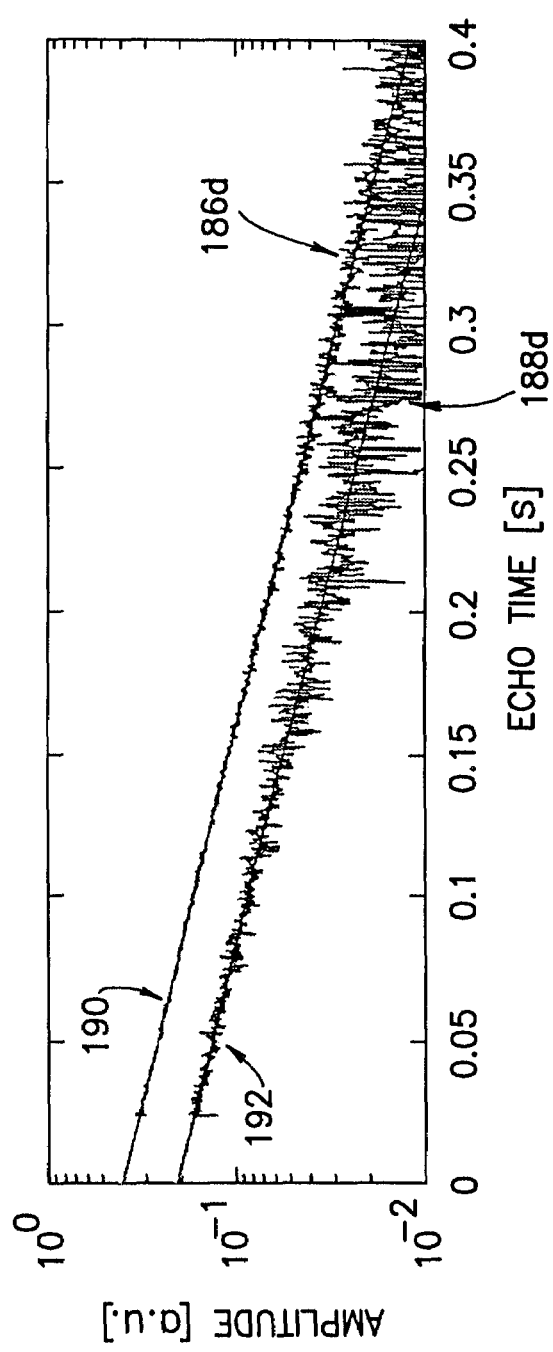

NUCLEAR MAGNETIC RESONANCE MEASUREMENT TECHNIQUES IN NON-UNIFORM FIELDS

BACKGROUND

1. Field of Invention

The present invention relates to nuclear magnetic resonance techniques for measuring parameters of a sample, particularly in inhomogeneous magnetic fields.

2. Discussion of Related Art

In standard nuclear magnetic resonance (NMR) spectroscopy, the primary information of interest is contained in the spectrum of the signal. This is made possible because magnets are now available with homogeneities typically better than 1 part in $10^8$. However, some applications require large samples which are unable to fit inside standard superconducting magnets, and thus require the use of one-sided magnet systems. As a result, the magnetic field across these samples is necessarily inhomogeneous and the signal-to-noise ratio is intrinsically low. One such application is in the field of oil-well logging.

A natural scale by which to measure inhomogeneities in the static field, $B_0$, is the amplitude of the RF field $B_1$. In this disclosure, the term grossly inhomogeneous fields is used to describe those fields in which the inhomogeneities of the static field, $\Delta B_0$, exceed the strength of the RF field, $B_1$. In this case, the NMR signal spectrum depends mainly on $B_1$ and the value of the dephasing time of the free induction decay, $T^*_2$, is on the order of the pulse duration. This implies that standard NMR spectroscopy cannot be used encode chemical or spatial information in the signal spectrum. As a consequence, the standard "spectral approach" fails with downhole NMR logging devices that have grossly inhomogeneous fields.

Spin relaxation times, such as the longitudinal relaxation time, $T_1$, and the transverse relaxation time, $T_2$, are important for characterization of crude oils. Most NMR logging measurements are currently based on measurements of transverse relaxation times, $T_2$, because they can be measured very efficiently using a Carr-Purcell-Meiboom-Gill (CPMG) pulse sequence. The CPMG sequence generates a long train of echoes whose amplitudes decay with the time constant $T_2$. In this case, the echo amplitudes provide the essential information, in particular, the initial amplitude and the decay time. The measurement of the longitudinal relaxation time, $T_1$, is more time consuming. However, there are circumstances when $T_1$ measurements may be more desirable than $T_2$ measurements, particularly when the intrinsic relaxation times are long, for example, greater than one second. In such cases, the intrinsic $T_2$ sometimes cannot be determined because the measurement becomes dominated by diffusion and motion effects, whereas in contrast, $T_1$ is not affected by diffusion and is less affected by motion effects.

A large number of $T_1$ measurement techniques can be found in the literature. The majority of schemes are based on inversion recovery or saturation recovery. This requires measurements with long recovery times (e.g., greater than several times $T_1$) to determine the equilibrium magnetization, $M_0$. In samples with long $T_1$, this results in very lengthy measurement cycles. There are many techniques that attempt to speed up measurements of $T_1$, such as measuring the approach to steady-state magnetization, progressive saturation measurements (in which a series of steady state signals with different relaxation weightings are measured), speed-optimized fast-inversion recovery (FIR) methods, and many others. However, common to most existing methods is the requirement to take one or several data for recovery times much longer than $T_1$ in order to obtain the equilibrium signal.

Single-scan measurements are the fastest $T_1$ measurement schemes. Many of these schemes are a modification of the so-called "triplet method," in which the recovering longitudinal magnetization is monitored by briefly converting it into transverse magnetization, detecting it, and the restoring it back to longitudinal magnetization. However, in grossly inhomogeneous fields, off-resonance effects prevent complete conversion into transverse magnetization and back. As a result, the measured relaxation time is not a pure $T_1$ relaxation time, but with a strong admixture of $T_2$. Another single-scan approach to measure $T_1$ is based on a standard two-dimensional inversion-recovery sequence, but the second dimension is encoded in the spatial dimension using pulsed field gradients. This allows the second dimension to be encoded simultaneously with the first dimension to reduce the measurement time to that of a one-dimensional experiment. However, this technique is also not easily adapted to grossly inhomogeneous fields.

SUMMARY OF INVENTION

Aspects and embodiments of the invention are directed to methods and pulse sequences for facilitating nuclear magnetic resonance (NMR) measurements in grossly inhomogeneous fields. There are described herein methods and pulse sequences that may be used to accurately measure variables such as transverse relaxation time, longitudinal relaxation time, and diffusion, without the need for data at long recovery time. This may allow faster measurements. In addition, there are described herein methods and pulse sequences that may allow simultaneous encoding of information in both the amplitude and the shape of echoes, so as to allow a single-shot measurement of multiple variables, e.g., both transverse relaxation time (from the decay of echo amplitudes) and longitudinal relaxation time (from the echo shape). CPMG detection may be used to overcome the often limited signal-to-noise ratio in grossly inhomogeneous fields.

According to one embodiment, a method of measuring a longitudinal relaxation time in a sample having an initial magnetization may comprise disturbing the initial magnetization with a first series of RF pulses, after a recovery time period has elapsed, applying a second series of RF pulses to the sample to acquire a first signal comprising at least two echoes, disturbing the initial magnetization differently with a third series of RF pulses, after the recovery time period has elapsed, applying a fourth series of RF pulses to the sample to acquire a second signal comprising at least two echoes, obtaining a difference signal from the first signal and the second signal, and analyzing the difference signal to obtain the longitudinal relaxation time. The measurement may be repeated for a series of recovery times including both short recovery times (i.e., less that the longitudinal relaxation time) and long recovery times (e.g., several times the length of the longitudinal relaxation time).

In one example, the second and fourth series of RF pulses may be substantially identical, and may comprise a Carr-Purcell-Meiboom-Gill (CPMG) pulse sequence. In another example, analyzing the difference signal may comprise fitting a function, such as a single or double exponential function, or a one- or two-dimensional numerical Laplace inversion, to the difference signal. In one example, the first series of RF pulses may comprise a first pair of 90° pulses and the third series of RF pulses may comprise a second pair of 90° pulses, wherein the first and second pairs of 90° RF pulses may have different phase cycling. In another example, the first series of RF pulses may comprise a 180° pulse and the third series of RF pulses may have no corresponding pulse.

Another embodiment may be directed to a method of measuring a longitudinal relaxation time in a sample having an initial magnetization, the method comprising applying a sequence of RF pulses to the sample, the sequence including an encoding portion and a detection portion, acquiring an echo signal using the detection portion of the sequence of RF pulses, decomposing the echo signal into at least two coherence pathway components; and analyzing at least one of the two coherence pathway components to determine the longitudinal relaxation time. In one example, decomposing the echo signal into at least two coherence pathway components may include decomposing the echo signal into a decay component and a recovery component. In another example, analyzing at least one of the two coherence pathway components may include analyzing the decay component. In one example, the encoding portion of the sequence of RF pulses may comprise a pair of 127° pulses separated from one another by a first time period.

According to another embodiment, a method of measuring diffusion in a sample may comprise applying a sequence of RF pulses to the sample, the sequence including an encoding portion and a detection portion, acquiring an echo signal using the detection portion of the sequence of RF pulses, decomposing the echo signal into at least two coherence pathway components, and analyzing the at least two coherence pathway components to determine a diffusion coefficient. In one example, decomposing the echo signal into at least two coherence pathway components may include decomposing the echo signal into a direct echo component and a stimulated echo component. Analyzing the at least two coherence pathway components may then include extracting a first amplitude of the direct echo component, extracting a second amplitude of the stimulated echo component, and determining the diffusion coefficient from a ratio of the first and second amplitudes. In one example, the detection portion of the sequence of RF pulses may comprise a Carr-Purcell-Meiboom-Gill (CPMG) pulse train. In another example, the encoding portion of the sequence of RF pulses may comprise a 90° pulse and a pair of 180° pulses having phases that differ by 90°.

According to another embodiment, a nuclear magnetic resonance measurement device may comprise a transmitter constructed and arranged to generate a sequence of RF pulses and to apply the sequence of RF pulses to a sample, a receiver constructed and arranged to receive an echo signal from the sample, and a processor constructed and arranged to decompose the echo signal into at least two coherence pathway components, and to analyze the at least two coherence pathway components to determine a parameter of the sample. In one example, the sequence of RF pulses may comprise an encoding portion and a detection portion. The detection portion may comprise a Carr-Purcell-Meiboom-Gill (CPMG) pulse train. The encoding portion may comprise, for example, a pair of 127° pulses separated from one another by a first time period, or a 90° pulse and a pair of 180° pulses having phases that differ by 90°. In one example, the processor may be constructed and arranged to decompose the echo signal into a decay component and a recovery component. In one example, the processor may be constructed and arranged to analyze the decay component to obtain a measurement of a longitudinal relaxation time of the sample. In another example, the processor may be constructed and arranged to decompose the echo signal into a direct echo component and a stimulated echo component. The parameter of the sample may be a diffusion coefficient, and the processor may be constructed and arranged to analyze the direct echo component to extract a first amplitude, and to analyze the stimulated echo component to extract a second amplitude of the stimulated echo component; and wherein the processor is configured to determine the diffusion coefficient from a ratio of the first and second amplitudes.

BRIEF DESCRIPTION OF THE DRAWINGS

Various aspects and embodiments of the invention are described below with reference to the accompanying figures. In the drawings, which are not intended to be drawn to scale, each identical or nearly identical component that is illustrated in various figures is represented by a like numeral. For purposes of clarity, not every component may be labeled in every drawing. In the drawings:

FIGS. 27A-E are plots of extracted amplitudes versus time of in-phase and out-of-phase signal components for the corresponding echo shapes of FIGS. 26A-E;

DETAILED DESCRIPTION

Oilfield fluids may contain components that exhibit very long spin relaxation times, particularly, long longitudinal spin relaxation times, $T_1$. For example, oils with high gas-to-oil ratio (GOR) at high temperatures may present a $T_1$ on the order of about 10 seconds (s). However, conventional methods for measuring $T_1$, such as inversion recovery and saturation recovery, require data with recovery times comparable to, or several times larger than, $T_1$, making it difficult for continuous logging. Aspects and embodiments of the invention, therefore, are directed to methods for obtaining accurate measurements of $T_1$, particularly in inhomogeneous fields, without the need for data at long recovery times. Techniques according to various aspects of the invention may allow much faster acquisition of well-logging data, particularly for very light oil with high GOR, and/or a significant improvement in the accuracy of $T_1$ measurements.

According to one embodiment, there are provided pulse sequences that generate multiple echoes and are suitable for logging and other applications in inhomogeneous fields. Information may be extracted from an analysis of the echo amplitudes and/or echo shapes. In one embodiment, sequences are provided, using amplitude encoding, to measure transverse relaxation times, $T_2$, longitudinal relaxation times, $T_1$, diffusion coefficients, D, and the corresponding one-dimensional and two-dimensional distribution functions between these quantities, as discussed further below. In another embodiment, information about the above-mentioned properties may also be encoded in the echo shape, which may be particularly useful for measuring quantities such as $T_1$ and D that are time consuming to measure with conventional approaches. This echo shape encoding maybe combined with echo amplitude encoding, leading to significant decreases in measurement time, and/or increase in information obtained.

Figure 1:
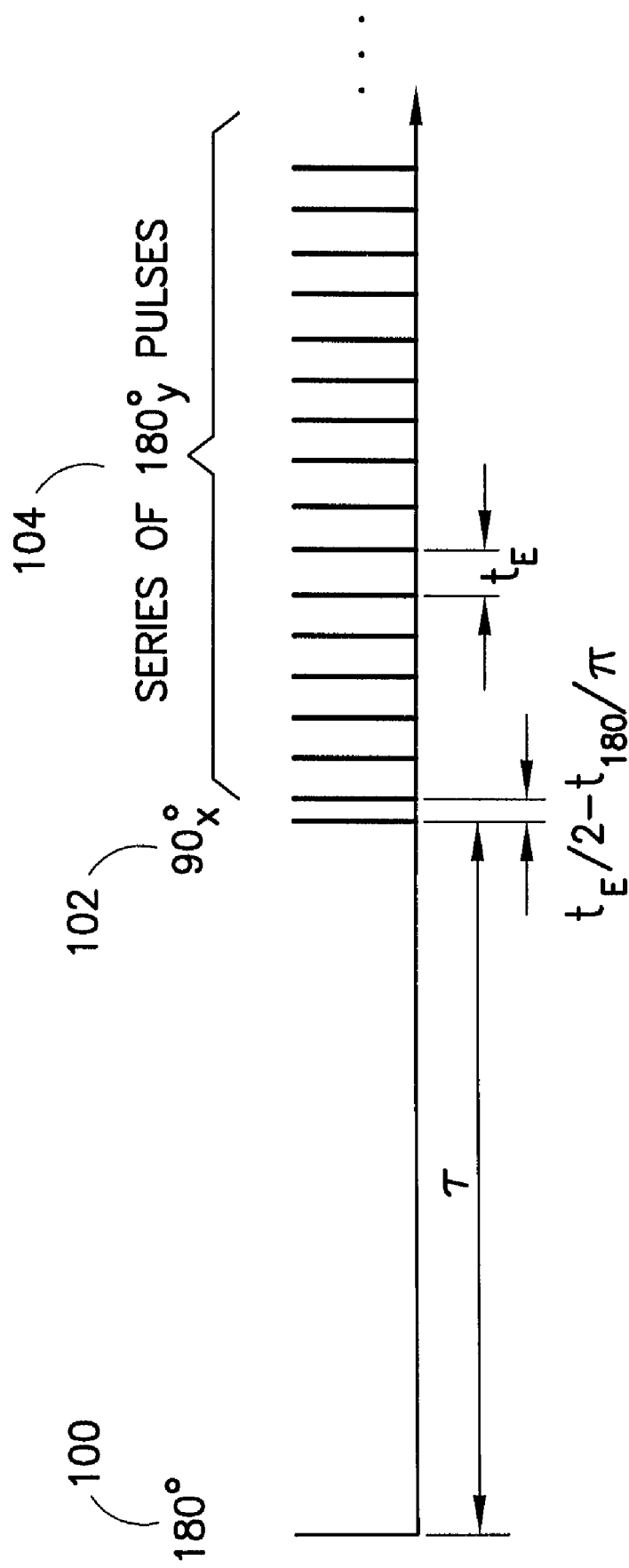
FIG. 1 is a diagram of a standard inversion recovery CPMG sequence using nominal 180° and 90° pulses.

The standard Carr-Purcell-Meiboom-Gill (CPMG) pulse sequence comprises an initial nominal 90° pulse that generates transverse magnetization. For multi-dimensional measurements, the initial 90° pulse may be replaced by a preparation pulse sequence that may be varied to change the sensitivity to a quantity of interest. For example, the preparation sequence may be an inversion recovery sequence (180°-τ-90°) to encode $T_1$ information or a stimulated echo sequence (90°-δ-90°-$T_d$-90°-δ) to encode diffusion information (where $T_d$ and δ are pulse spacings. $T_d$ often being referred to as the diffusion time, and δ being the gradient encoding time). This initial pulse sequence is then followed by a long series of closely-spaced 180° refocusing pulses. Referring to FIG. 1, there is illustrated one example of a standard inversion recovery CPMG pulse sequence. The inversion recovery sequence, 180°-τ-90°, includes nominal 180° and 90° pulses 100 and 102, respectively, separated by a time, τ. The initial RF pulse 100 modifies the equilibrium magnetization. Next, the second RF pulse 102 is applied after some time, τ, has elapsed in order to monitor the recovery of the magnetization to equilibrium. The initial pulse sequence is followed by the series of refocusing pulses 104. The refocusing pulses are separated from one another by a time, $t_E$. In CPMG-like sequences, the repeated refocusing may serve two purposes. First, many echoes may be averaged to obtain the echo shape S(t). This may help to overcome the intrinsically small signal-to-noise ratio in grossly inhomogeneous fields. Second, the time dependence of the echo amplitudes allows measurement of the magnetization spin relaxation times, as discussed further below.

In grossly inhomogeneous fields, the spectrum of echoes from a CPMG-like sequence quickly approaches an asymptotic form and may be given by:

$$S(\omega_0) = (\vec{M}_A \cdot \hat{n})\hat{n} \tag{1}$$

For the standard CPMG sequence, on resonance, $S(\omega_0=0) = M_0$, the thermal equilibrium magnetization. The magnetization of the k-th echo may be given by:

$$\vec{M}_k = (\vec{M}_A \cdot \hat{n})\hat{n} \exp(-kt_E/T_{2,eff}) \tag{2}$$

where:

$\vec{M}_A$ is the magnetization after the initial preparation period;
$t_E$ is the echo spacing; and
$T_{2,eff}$ is the transverse spin relaxation time.

According to one embodiment, to calculate $M_A$ and its dependence on parameters such as diffusion or $T_1$, the magnetization evolution may be divided into different coherence pathways. Each coherence pathway may have a distinct dependence on parameters of interest, such as relaxation times or diffusion coefficients, and may generate a signal of known echo shape. The measured echo shape may then be decomposed into contributions from the individual coherence pathways and the relative amplitudes may be directly related to the parameters of interest, as discussed further below.

For any coherence pathway, i, the echo signal in grossly inhomogeneous fields may be factorized into a spectral portion $s_i(\omega_0)$ and an amplitude $a_i(D, T_1, \ldots)$. The spectral portion $s_i(\omega_0)$ may depend only on the applied RF pulses. On the other hand, the effects of diffusion, relaxation, flow or pulsed field gradients perpendicular to the static field gradient may be uniform across the spectrum and may be described by the amplitude $a_i$. This amplitude may depend on the duration of the time intervals between the RF pulses. The asymptotic spectrum of echoes from equation (2) may be written as a sum over the different coherence pathways:

$$S(\omega_0) = (\vec{M}_A \cdot \hat{n})\hat{n} = \sum_{i=1}^{N} s_i(\omega_0) a_i(D_i, T_1, \ldots) \tag{3}$$

Since different coherence pathways have, in general, different sensitivities to diffusion or $T_1$, the spectrum $S(\omega_0)$, or echo shape in the time domain, of the echo signal may depend on these parameters. Thus, information may be encoded not only in the amplitude of the echo signal, but also in the echo shape. This allows a two-dimensional measurement from a single echo pulse sequence.

In grossly inhomogeneous fields, the signal-to-noise ratio of a single echo acquisition may be insufficient to allow a detailed analysis of its shape. This may be overcome by using pulse sequences that comprise an initial preparation or encoding sequence followed by a long train of refocusing pulses (e.g., a CPMG sequence). The CPMG-like sequence may serve two distinct roles. First, the decay of the echo amplitudes may give a measurement of $T_2$. Second, it may greatly increase the precision of the echo shape measurement because, after the first few pulses, the echo shapes may not change and therefore, a large number of echoes may be averaged to obtain a robust shape with good signal-to-noise ratio. Further, in one embodiment, to optimize the "single-shot" measurement approach according to aspects of the invention, preparation sequences may be chosen with significant contributions from different coherence pathways that exhibit greatly different sensitivities to a parameter of interest (e.g., $T_1$) and that also have echo shapes that are as orthogonal to each other as possible. Examples of such preparation sequences are discussed below.

According to one embodiment, preparation sequences may be selected such that at least two coherence pathways contribute to the echo signal. This may be demonstrated with reference to the inversion recovery sequence combined with CPMG detection shown in FIG. 1. After the recovery time, $\tau$, at the time of the 90° pulse 102, the magnetization may have components from two different coherence pathways referred to as the "decay" component (from the decaying coherence pathway) and the "recovery" component (from the recovering coherence pathway). If the initial magnetization of a sample is $M_0$, then the spectrum of echoes after the first few refocusing pulses may be obtained from equation (3) and may be given by:

$$S(\omega_0) = s_d(\omega_0) \exp\{-\tau/T_1\} + s_r(\omega_0)(1 - \exp\{-\tau/T_1\}) \tag{4}$$

The first term of equation (4) is the contribution from the decaying coherence pathway and the second term is the contribution from the recovering coherence pathway. The spectra of the individual coherence pathways may be given by:

$$s_d(\omega_0) = M_0 Im((\Lambda_{+1,-1}^{(3)} \Lambda_{-1,0}^{(2)} \Lambda_{0,0}^{(1)}) e^{-i\omega_0 t_{180}/\pi} n_y^2) \tag{5}$$

$$s_r(\omega_0) = M_0 Im((\Lambda_{+1,-1}^{(3)} \Lambda_{-1,0}^{(2)}) e^{-i\omega_0 t_{180}/\pi} n_y^2) \tag{6}$$

where:

$\Lambda_{i,j}^{(k)}$ are transition probabilities for the k-th pulse between three different magnetization components ($M_{+1}$, $M_{-1}$, $M_0$);
$t_{180}$ is the time at the first of the series of 180° pulses 104 (see FIG. 1);
$n_y$ is the y-component of the effective rotation axis for the refocusing cycle; and
Im indicates that the imaginary component of the expression in brackets is important.

In one example, to maximize the signal, the pulse spacing between the 90° pulse 102 and the first 180° refocusing pulse may be reduced from half the echo spacing by $t_{180}/\pi$, as shown in FIG. 1. This reduction is reflected in equations (5) and (6) by the extra phase shifts of $\exp(-i\omega_0 t_{180}/\pi)$.

Based on equations (5) and (6), echo shapes due to the decay and recovery components may be calculated. For an extended sample along the field gradient direction, the echo shapes in the time domain are the Fourier transforms of equations (5) and (6). It is to be appreciated that after the first few echoes, all subsequent echoes may have substantially the same shape in the time domain and it is thus still possible to average many echoes to achieve good statistics. In the time domain, the overall echo shape may be given by a weighted sum of the characteristic echo shapes from the decaying, coherence pathway and the recovering coherence pathway:

$$S(t) = s_r(t)(1 - \exp(-\tau/T_1)) + s_d(t)\exp(-\tau/T_1) \tag{7}$$

In equation (7), the first term is referred to herein as the recovery component and the second term is referred to as the decay component.

Figure 2B:
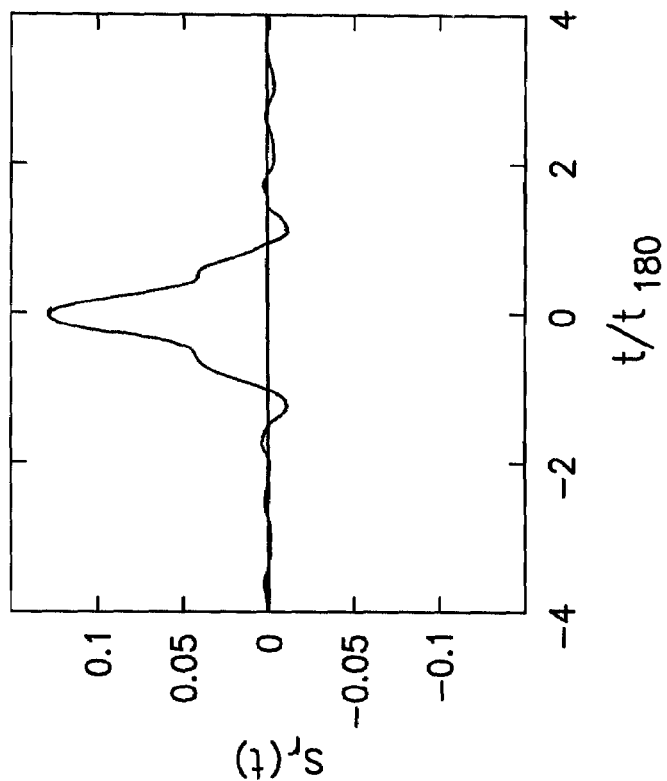
FIG. 2B is a diagram of the calculated echo shape of the in-phase signal for the recovering coherence pathway.
Figure 2A:
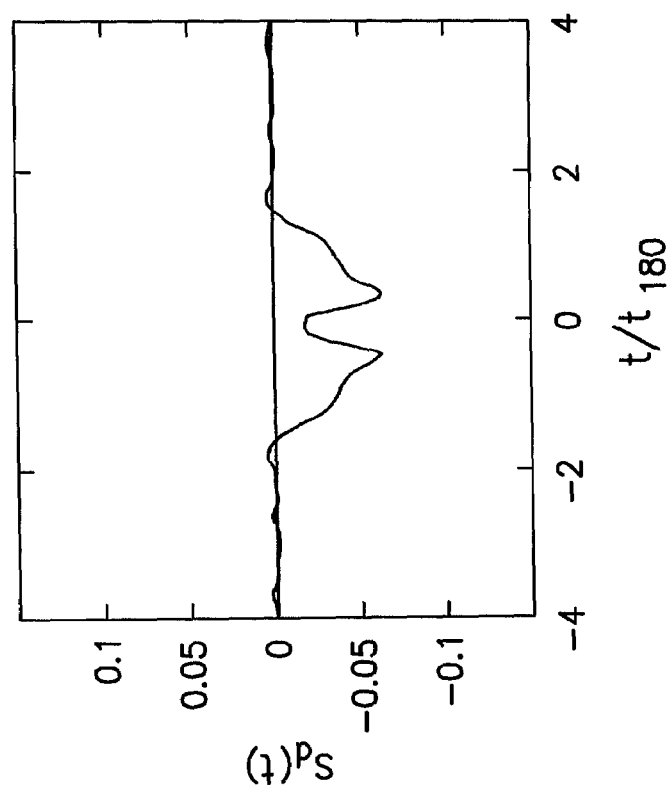
FIG. 2A is a diagram of the calculated echo shape of the in-phase signal for the decaying coherence pathway.

Referring to FIGS. 2A and 2B, there are illustrated calculated echo shapes for the decaying (FIG. 2A) and recovering (FIG. 2B) coherence pathway for the pulse sequence of FIG. 1. Both echo shapes have only contributions in phase with the 180° refocusing pulses. They differ significantly from one another so that the measured echo shape can be decomposed into the two shapes, $s_r(t)$ (the recovery component) and $s_d(t)$ (the decay component), as discussed below.

Figure 3:
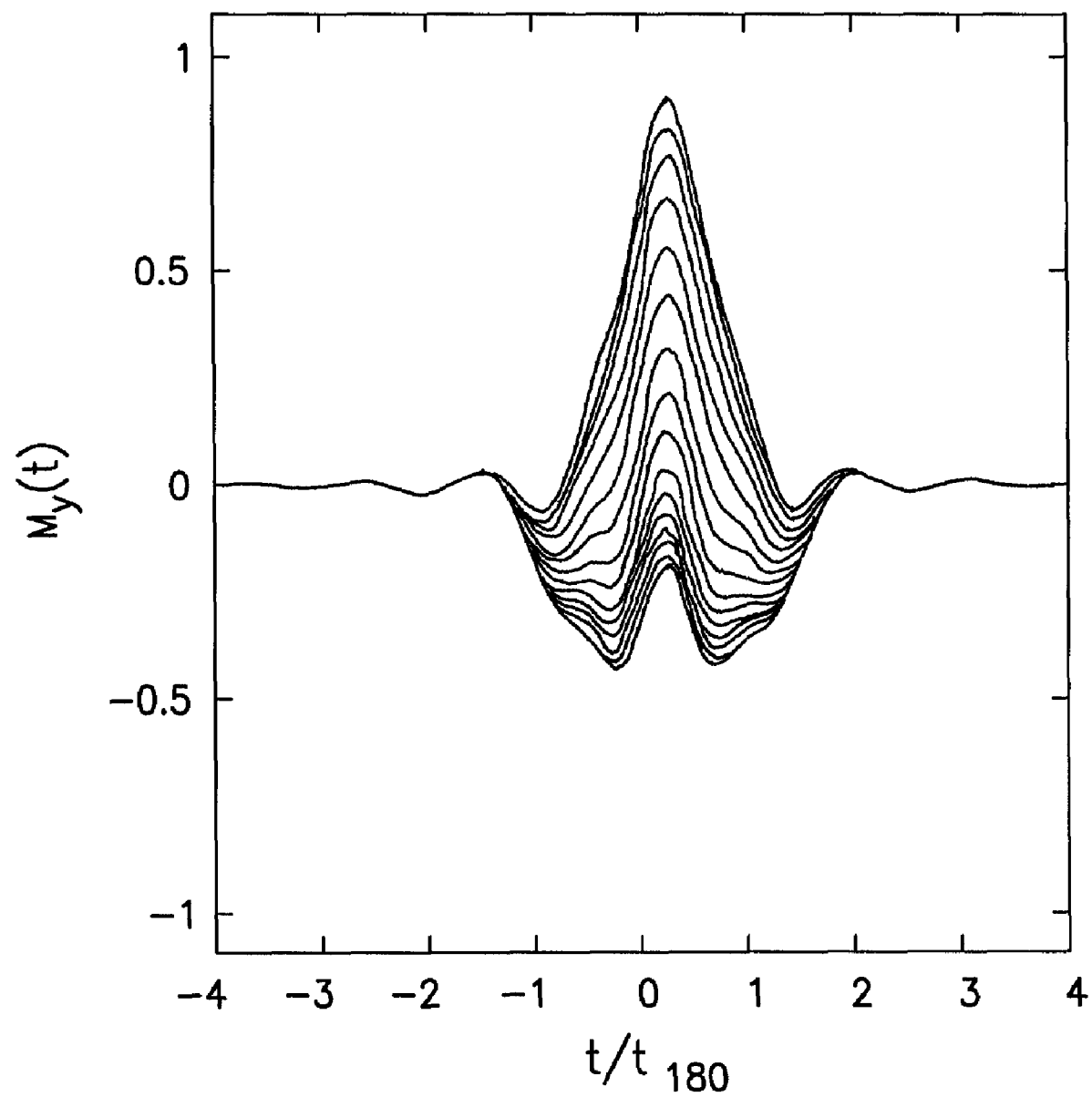
FIG. 3 is a diagram of example echo shapes of the in-phase signal for different recovery times between 1 ms and 10 s.

An example was performed to confirm the calculated results discussed above and illustrated in FIGS. 2A and 2B. In this example, a sample of doped water having a longitudinal relaxation time $T_1$=113.5 milliseconds (ms) was placed in the fringe field outside a superconducting magnet. The RF frequency was set to 1.764 Megahertz (MHz) and the static gradient was 132 millitesla per meter (mT/m). For most measurements, approximately 1000 to 2000 echoes were acquired in the CPMG train. The diameter of the sample was 38 millimeters (mm), which was much larger than the typical slice thickness (approximately 5 mm), such that to first order, the finite sample size may be neglected. The echo spacing, $t_E$, was chosen to be 384 μs and $t_{180}$=24 μs. In one example, the recovery time, τ, was varied logarithmically between 1 millisecond (ms) and 10 seconds (s). For the measurement at each recovery time, the signal from the $10^{th}$ to the $110^{th}$ echo was averaged to obtain the echo shapes illustrated in FIG. 3. For short recovery times, τ<<$T_1$, the measured echo shapes coincide with the shape of $s_d(t)$ (shown in FIG. 2A), whereas in the other limit, τ>>$T_1$, the echo shapes approach $s_r(t)$ (shown in FIG. 2B). This example therefore confirms the sensitivity of the echo shape to $T_1$. In addition, the example suggests the usefulness of the decay component in determining $T_1$ for short recovery times at which the composite echo shape tends to approach that of the decay component alone.

For a standard inversion recovery CPGM sequence, such as shown in FIG. 1, and for simplicity setting $s_r(t)$=$M_0$, equation (7) can be rewritten:

$$S(\tau) \propto M_0(1-\alpha \exp(-\tau/T_1)) \quad (8)$$

where α is determined from $M_0$ and $s_d(t)$. When the exponent is much less than unity (i.e., τ/$T_1$<<1), corresponding to a recovery time much smaller than the longitudinal relaxation time, then:

$$S(\tau) \approx M_0(1-\alpha)+(\alpha M_0/T_1)\tau \quad (9)$$

At short recovery time, τ, the signal shows a linear τ dependence with a slope of $\alpha M_0/T_1$. This demonstrates that from very short recovery time data, it is impossible to determine the values of $M_0$ and $T_1$ independently. On the other hand, if one acquires the decay signal, rather than a recovery signal, that is, taking the decay component alone from equation (7) and, for simplicity's sake, setting $s_d(t)$=$M_0$, the echo signal as a function of recovery time is given by:

$$S(\tau) \propto M_0 \exp(-\tau/T_1) \quad (10)$$

It can be seen that the two variables, $M_0$ and τ, are more independent than they are in equation (8). For example, the slope of the logarithm of S (log S) versus τ will determine $T_1$ directly. Therefore, it may be desirable to determine $T_1$ from the decay component to avoid the problems of conventional inversion recovery, particularly at short recovery times. Accordingly, aspects and embodiments of the invention are directed to schemes to isolate the two signal components in order to obtain $T_1$ reliably from data at short τ only, as discussed below. Although there have been some efforts in the prior art to demonstrate the use of the decay component for $T_1$ measurement, these experiments have been performed in uniform magnetic fields. In contrast, schemes according to various embodiments of the invention are applicable to NMR measurements in grossly inhomogeneous fields, such as in a fringe field as exists in NMR logging tools, as discussed below.

From the above analysis of the short time behavior of the inversion recovery measurement method and the decay measurement method, it is clear that, within the short time limit, the conventional inversion recovery technique cannot determine $T_1$ independent of the amplitude of the signal. By analyzing the error propagation of the two methods, advantages of using the decay component may be further demonstrated. Referring again to equation (8), there are three parameters present in this fitting, namely, $M_0$, α, and $T_1$. By differentiating the right hand side of equation (8), the variance of the signal S may be obtained:

$$\delta S(\tau)^2 = \delta M_0^2\left(\frac{\partial S}{\partial M_0}\right)^2 + \delta T_1^2\left(\frac{\partial S}{\partial T_1}\right)^2 + 2\delta M_0 \delta T_1\left(\frac{\partial S}{\partial M_0}\frac{\partial S}{\partial T_1}\right) + \ldots \quad (11)$$

where:
  $\delta M_0$ is the variance of the parameter $M_0$;
  $\delta T_1$ is the variance of the parameter $T_1$; and
  $\delta M_0 \delta T_1$ is the covariance of the two parameters Formally, this relationship can be obtained for a function $f(x,p)$ with variable x and parameters p by defining the Jacobian matrix:

$$J \equiv \begin{pmatrix} f'_{p1}(x_1, p) & f'_{p2}(x_1, p) & \cdots \\ f'_{p1}(x_2, p) & f'_{p2}(x_2, p) & \cdots \\ \cdots & \cdots & \\ f'_{p1}(x_n, p) & f'_{p2}(x_n, p) & \cdots \end{pmatrix} \quad (12)$$

where:
  $x_i$ is the $i^{th}$ variable (such as τ);
  $p_i$ is the $i^{th}$ parameter (such as $T_1$); and
  $f'_{pi}$ is the derivative of the function $f$ with respect to the $i^{th}$ parameter:
  ($f'_{pi} \equiv \partial f/\partial p_i$).

The covariance matrix may then be obtained through the formula $(J^T J)^{-1}$, where the exponent −1 indicates matrix inversion. The diagonal elements of the covariance matrix may be useful in determining the ratio of the variance of the fitting parameters, for example, $\delta T_1^2$, to that of the data, $\delta S^2$. This ratio may serve as a quality index for the measurements.

Figure 4:
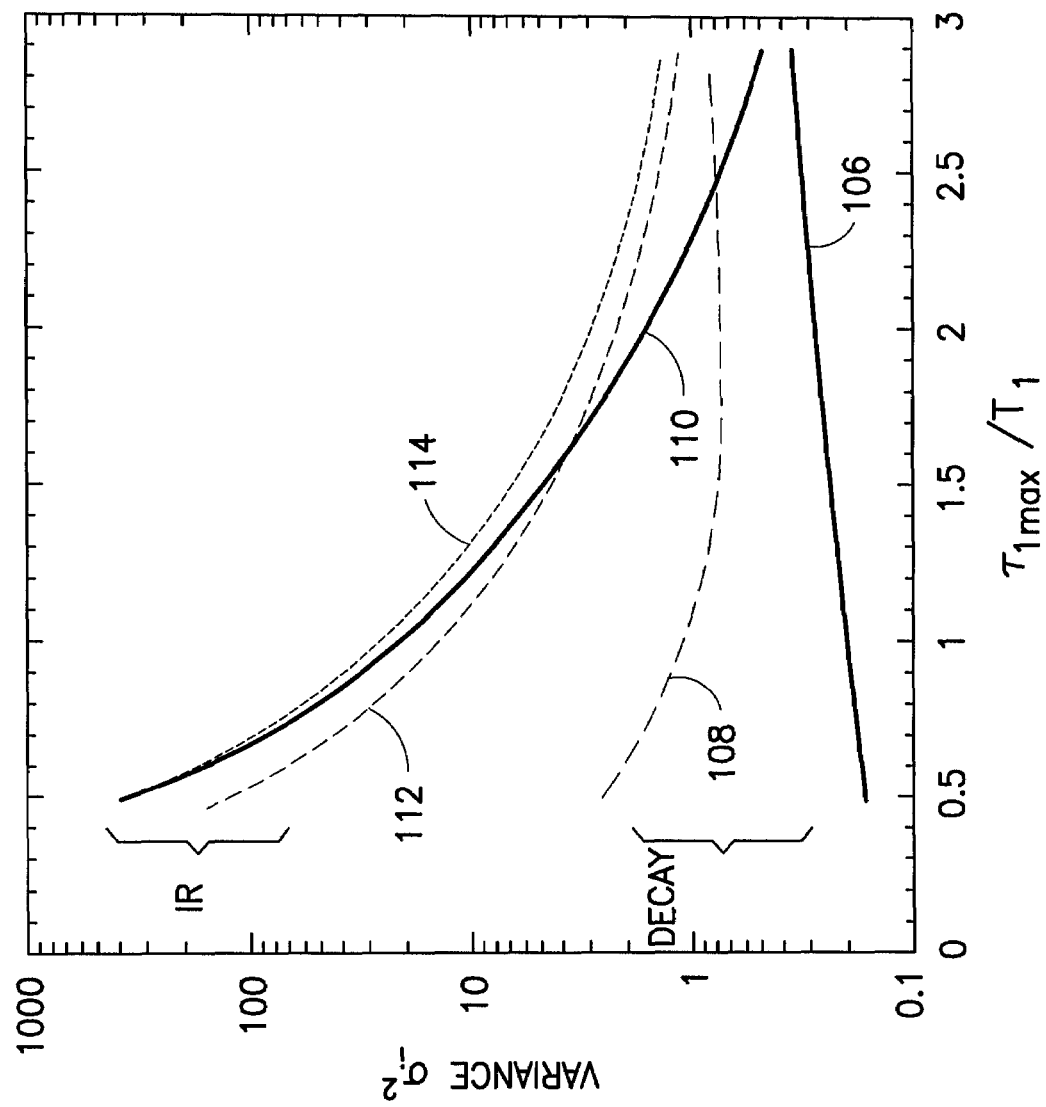
FIG. 4 is a plot showing the covariance matrix diagonal elements for inversion recovery and decay examples.

In one example, for both the inversion recovery method and the decay method (i.e. using only the decay component described by equation (10)), the covariance matrix was obtained for an example with 30 values of r over a range of τ from 0.1 $T_1$ to $\tau_{max}$. The diagonal elements from the covariance matrix are plotted in FIG. 4 as a function of $\tau_{max}$, with $\tau_{max}$ ranging from 0.5 $T_1$ to 3 $T_1$. Referring to FIG. 4, line 106 represents $M_0$ for the decay method example and line 108 represents $T_1$ for the decay method example. Line 110 represents $M_0$ for the inversion method recovery example and line 112 represents $T_1$ for the inversion recovery method example. For both examples, $M_0$ and $T_1$ were both assumed to be unity ($M_0$=1 and $T_1$=1). Line 114 represents α for the inversion recovery example, which was assumed to be equal to 2. As discussed above, when the recovery time $\tau_{max}$ is long (close to 3 $T_1$), the entire $T_1$ relaxation may be well observed in both the inversion recovery and the decay examples. Therefore, it is not surprising that both methods obtain similar and small variance for all the parameters. However, as $\tau_{max}$ is reduced, the variance for the inversion recovery method example increases dramatically, indicating larger errors in the estimate of the parameters ($M_0$ and $T_1$). By contrast, as can be seen in FIG. 4, the variance of these parameters in the decay method example (lines 106 and 108) remains relatively small and shows only a modest increase as $\tau_{max}$ approaches 0.5 $T_1$. These examples show that the inversion recovery method yields a variance about two orders of magnitude greater than does the decay method for the same parameters, providing mathematical evidence of an advantage of the decay method.

According to one embodiment, there is developed a class of preparation pulse sequences that may facilitate separating the recovery and decay components for an improved $T_1$ measurement. In one embodiment, a preparation pulse sequence may be constructed to acquire two signals by implementing the following steps. In a first scan, the equilibrium magnetization may be disturbed by a series of RF pulses, a time, $\tau$, may then be allowed to elapse, after which a second series of RF pulses may be applied to acquire the first signal. In a second scan, the equilibrium magnetization may be disturbed differently from the first scan, again a time, $\tau$, may be allowed to elapse, and then another series of RF pulses may be applied to acquire the second signal. Once the two signals are acquired, a difference signal (i.e., obtained by subtracting the first signal from the second signal, or vice versa) may be the decay component, and a summation of the two signals may provide the recovery component.

According to one embodiment, a class of pulse sequences that may be used to achieve separation of the decay component according to the above steps is referred to herein as Separation of Preexisting and Longitudinal Magnetization (SPARLM). It is to be appreciated that this acronym, as used herein, refers not only to the example pulse sequences described herein, but also to all analogous pulse sequences. In one example. the SPARLM sequence may comprise two 90° pulses with an (x,x) phase in one scan and another phase, (x,-x) in a second scan. The two 90° degree pulses may be separated by a short delay that may vary from one example to another and may be selected by a person performing the measurements. In one example, the signals in the two scans may be given by:

$$S_1 = M_0[1-\exp\{-\tau/T_1\}] - M_0 \exp\{-\tau/T_1\}$$

$$S_2 = M_0[1-\exp\{-\tau/T_1\}] + M_0 \exp\{-\tau/T_1\} \tag{13}$$

$S_1$ is the signal from the first scan and $S_2$ is the signal from the second scan. The difference of the signals from the two scans may produce the decay component (as can be seen with reference to equation (10)), and their addition may produce the recovery component. This process of subtraction or addition is referred to herein as decomposition because the effect is to divide the signal into the two-components.

Figure 5A:
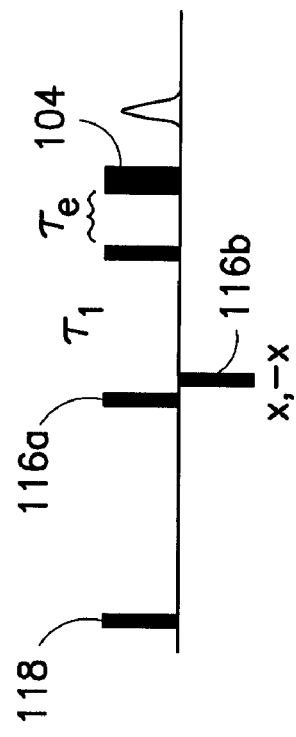
FIG. 5A is a diagram of a pulse sequence for a first measurement scan according to one embodiment of the invention.
Figure 5B:
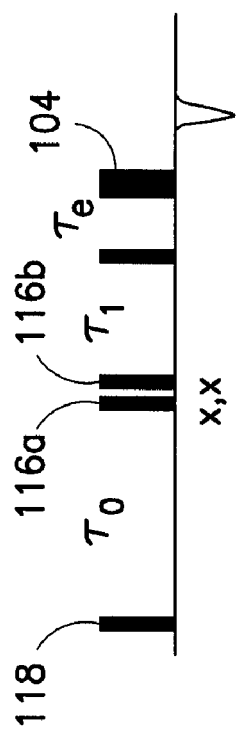
FIG. 5B is a diagram of a pulse sequence for a second scan, that forms a pair with the pulse sequence of FIG. 5A, according to one embodiment of the invention.

Referring to FIGS. 5A and 5B, there is illustrated one example of SPARLM pulse sequences. The narrower and wider boxes represent 90° and 180° pulses, respectively. FIG. 5A illustrates the signal in the first scan with the two 90° pulses 116a and 116b having phases (x,x). FIG. 5B illustrates the signal in the second scan with the pair of 90° pulses 116a,b having phases (x,-x). Both signals may also include a 90° presaturation pulse 118. This extra 90° pulse may be inserted at the beginning of the sequence to ensure equivalent preparation for all measured transients. The signal recovery during the $\tau_0$ period determines the magnetization before the pair of 90° pulses 116a,b. It is to be appreciated that the presaturation pulse 118 may be redundant because the long CPMG detection pulse train may establish a steady-state longitudinal magnetization with no memory of previous pulse sequences that may have been applied to the sample. The presaturation pulse 118 may therefore not be required, but may be included to serve as a quality control measure.

Figure 6A:
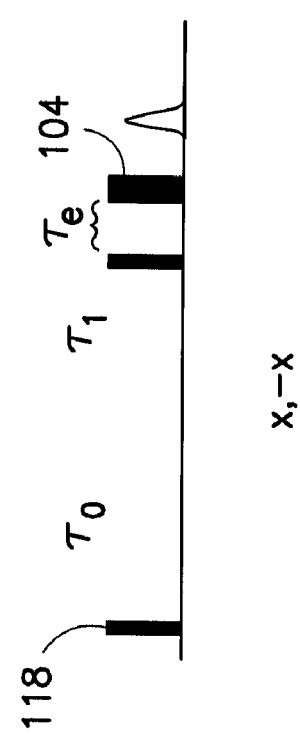
FIG. 6A is a diagram of another pulse sequence for a first measurement scan according to another embodiment of the invention.
Figure 6B:
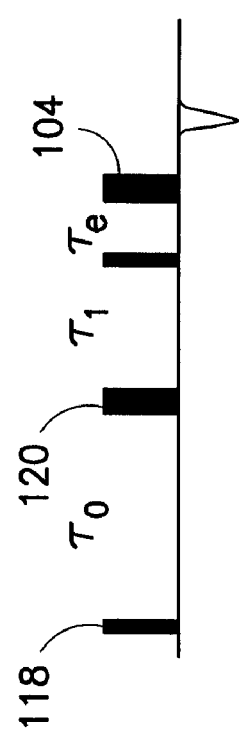
FIG. 6B is a diagram of a pulse sequence for a second scan, that forms a pair with the pulse sequence of FIG. 6, according to an embodiment of the invention.

Referring to FIGS. 6A and 6B, there is illustrated an example of a variation on the SPARLM pulse sequences of FIGS. 5A and 5B. In this example, the pair of 90° inversion pulses 116a,b may be merged, producing a 180° pulse 120 in the first scan (FIG. 6A) and no pulse in the second scan (FIG. 6B). This sequence may accomplish the same decay-recovery separation described above, but with a different (and simpler) spatial inversion profile. In this example, the sequences for the two scans resemble a "fast inversion recovery" (FIR) sequence (FIG. 6B) and a saturation recovery (SR) sequence (FIG. 6A). Therefore, this variation on the SPARLM sequence is referred to herein as FIR/SR.

For a pure on-resonance signal, it may be possible to adjust the excitation to achieve a uniform 90° pulse for the entire sample volume. However, when the sample is in a strong constant field gradient, all RF pulses are slice-selective and off-resonance effects may need to be accounted for. For example, a nominal 90° pulse may exhibit a nutation angle that is dependent on position. Therefore, to account for such effects, the signal equation for SPARLM may be modified:

$$S_1 = M_0[1-\exp\{\tau/T_1\}] + m_1 \exp\{-\tau/T_1\}$$

$$S_2 = M_0[1-\exp\{\tau/T_1\}] + m_2 \exp\{-\tau/T_1\} \tag{14}$$

where $m_1$ and $m_2$ may be different from each other and from $M_0$. However, even with this modification, the difference of $S_1$ and $S_2$ may still produce a pure decay signal:

$$S_d = (m_1 - m_2) \exp\{-\tau/T_1\} \tag{15}$$

Thus, the SPARLM pulse sequences may be compatible with grossly inhomogeneous field examples, as may occur in NMR well-logging tools.

Figure 7A:
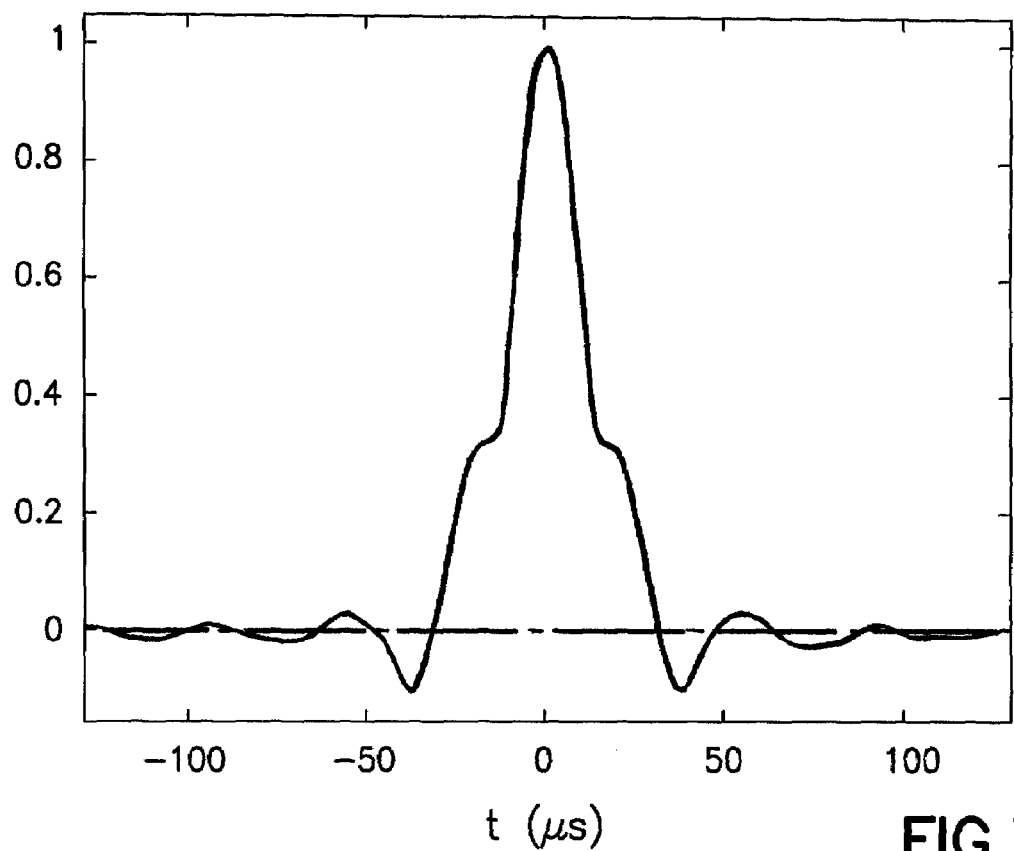
FIGS. 7A-H are illustrations of theoretical signal shapes in the time domain (FIGS. 7A, 7C, 7E and 7G) and frequency domain (FIGS. 7B, 7D, 7F and 7H) for a set of pulse sequences.
Figure 7B:
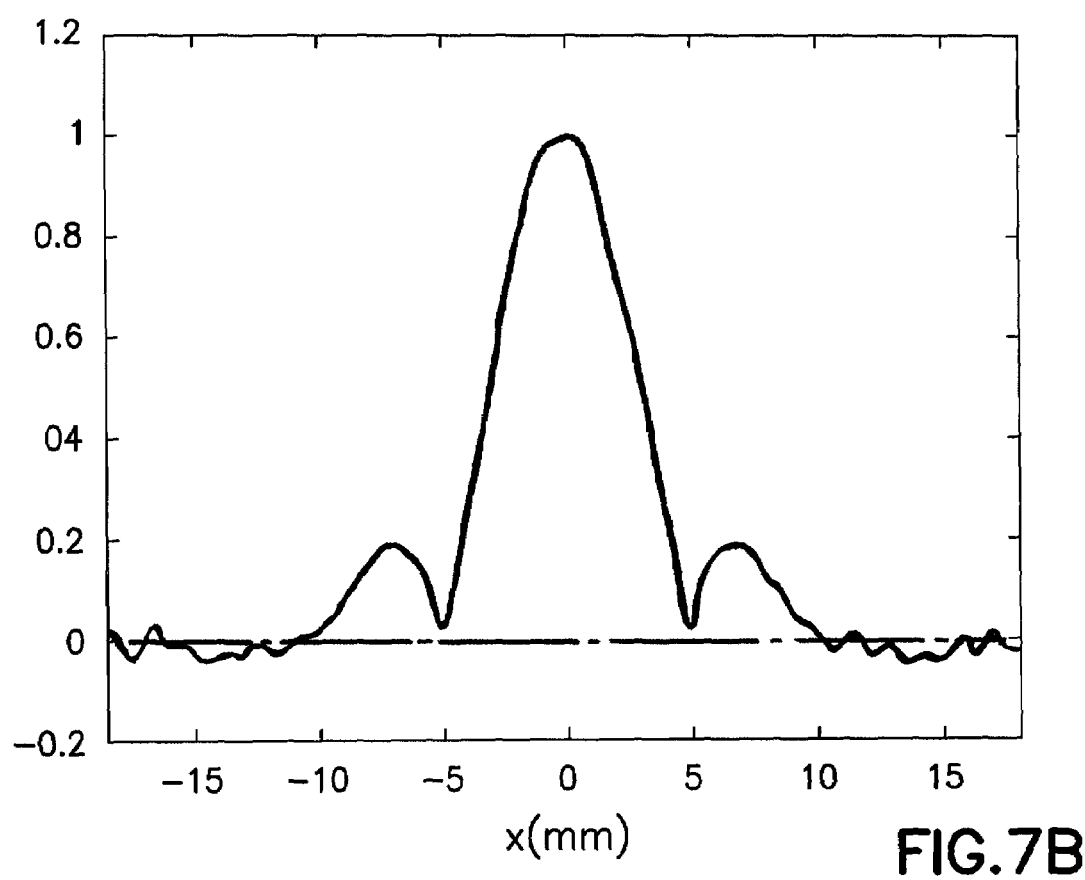
Figure 7C:
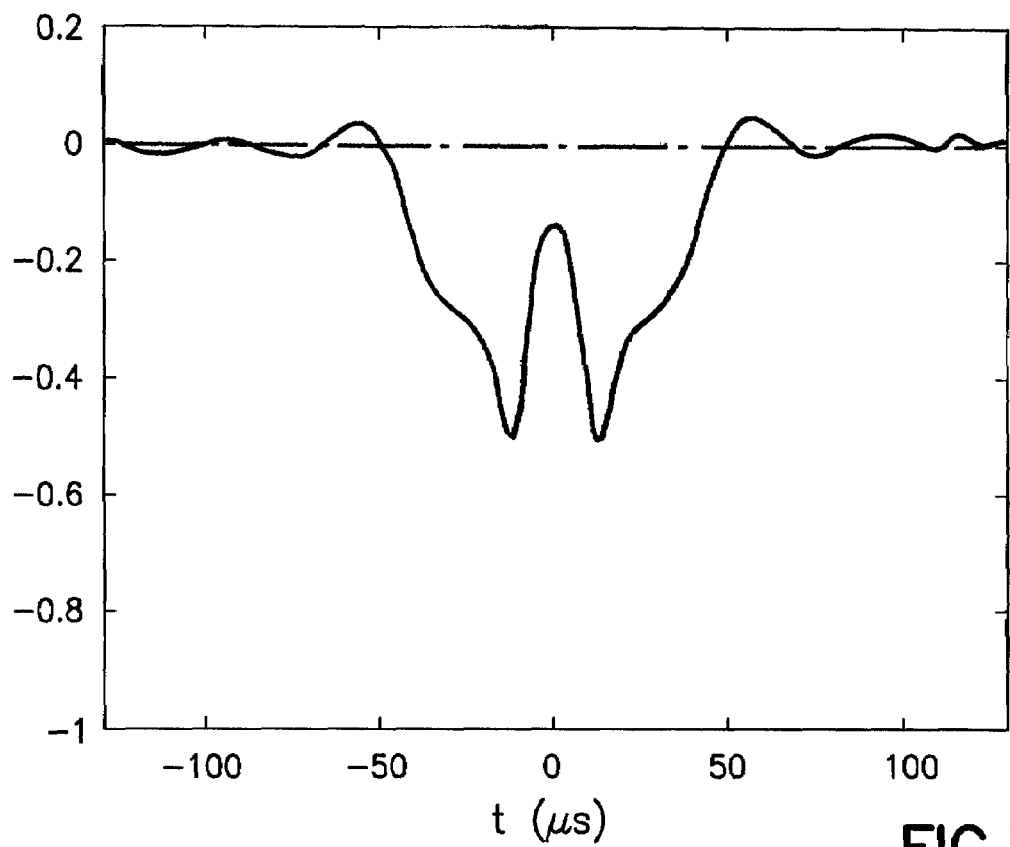
Figure 7D:
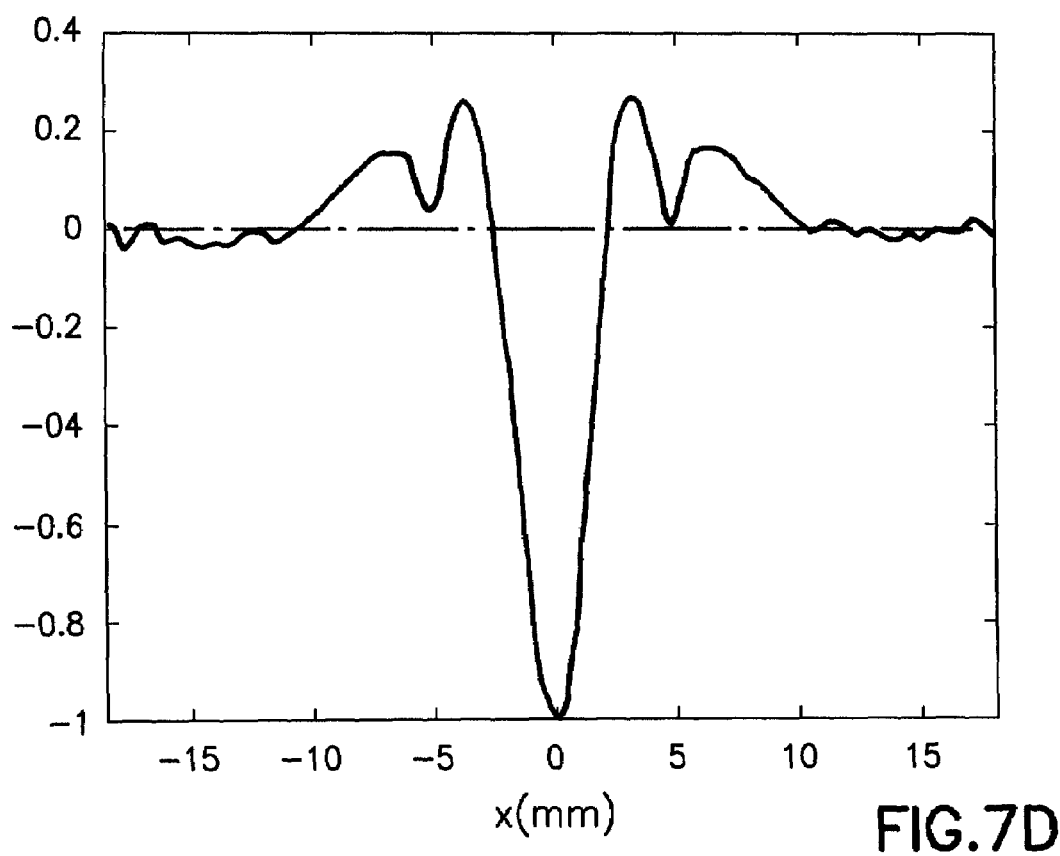
Figure 7E:
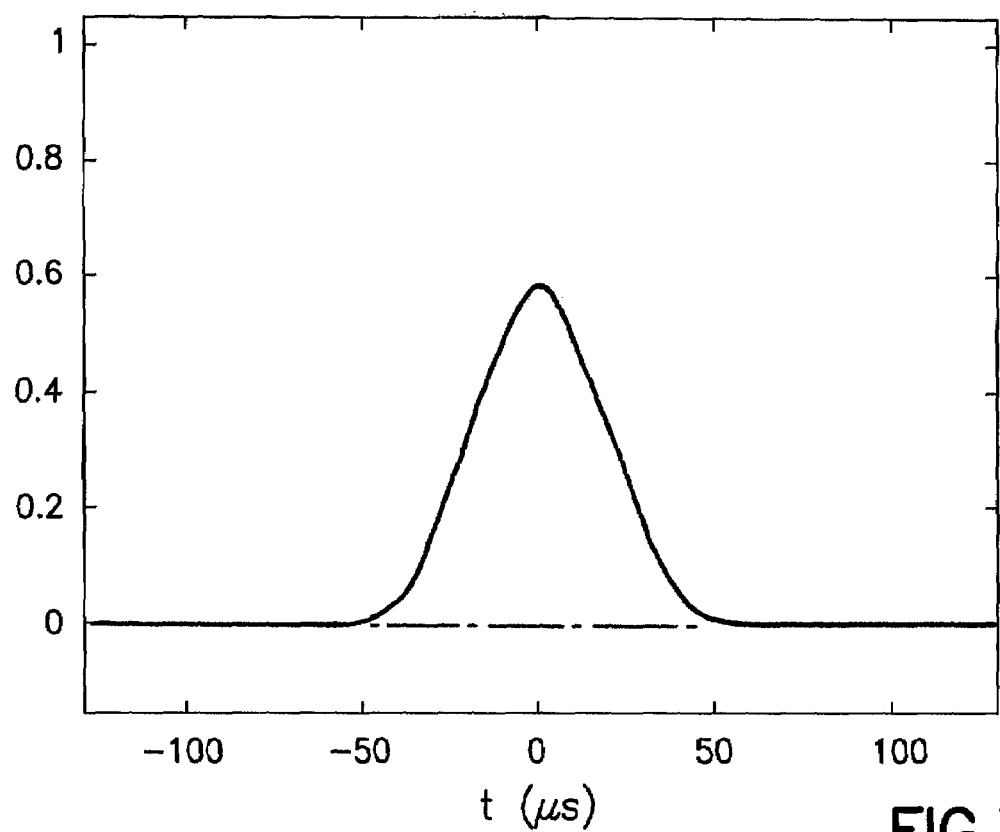
Figure 7F:
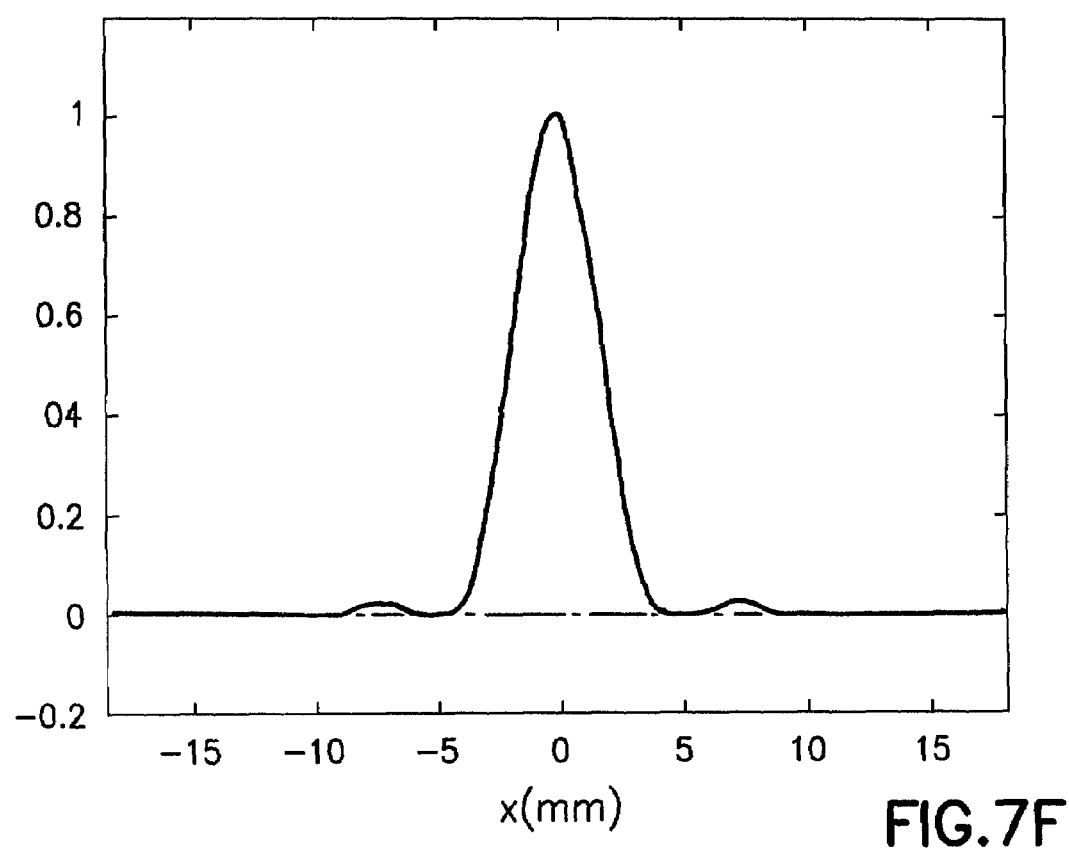
Figure 7G:
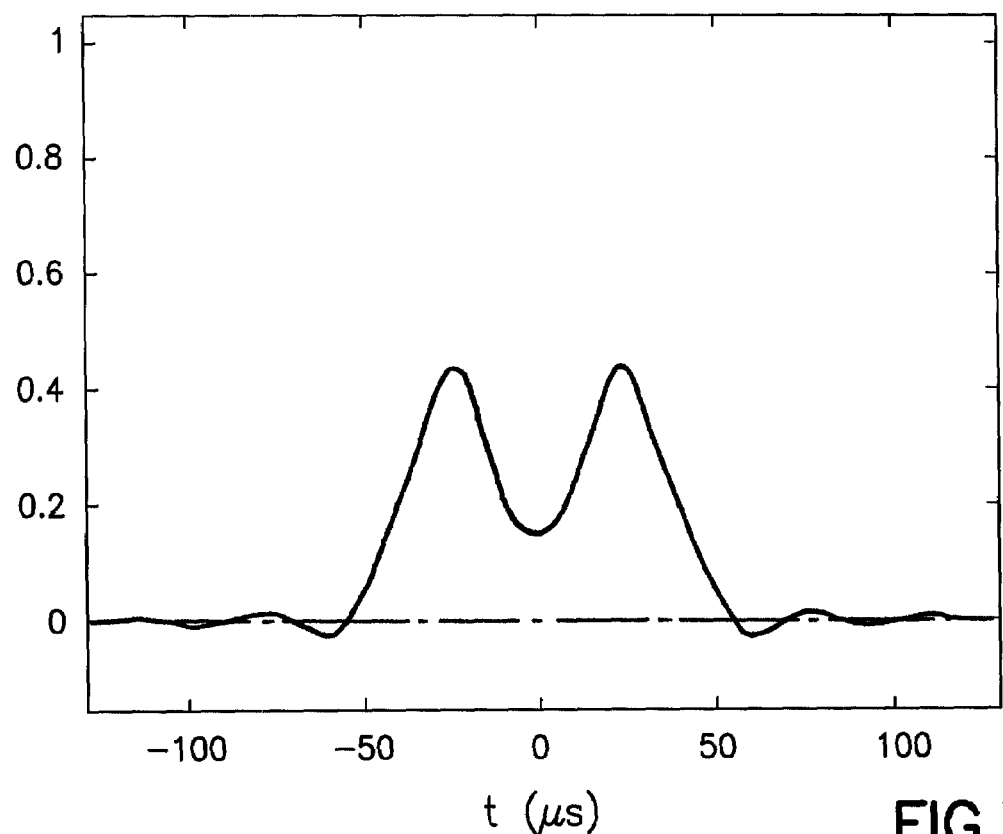
Figure 7H:
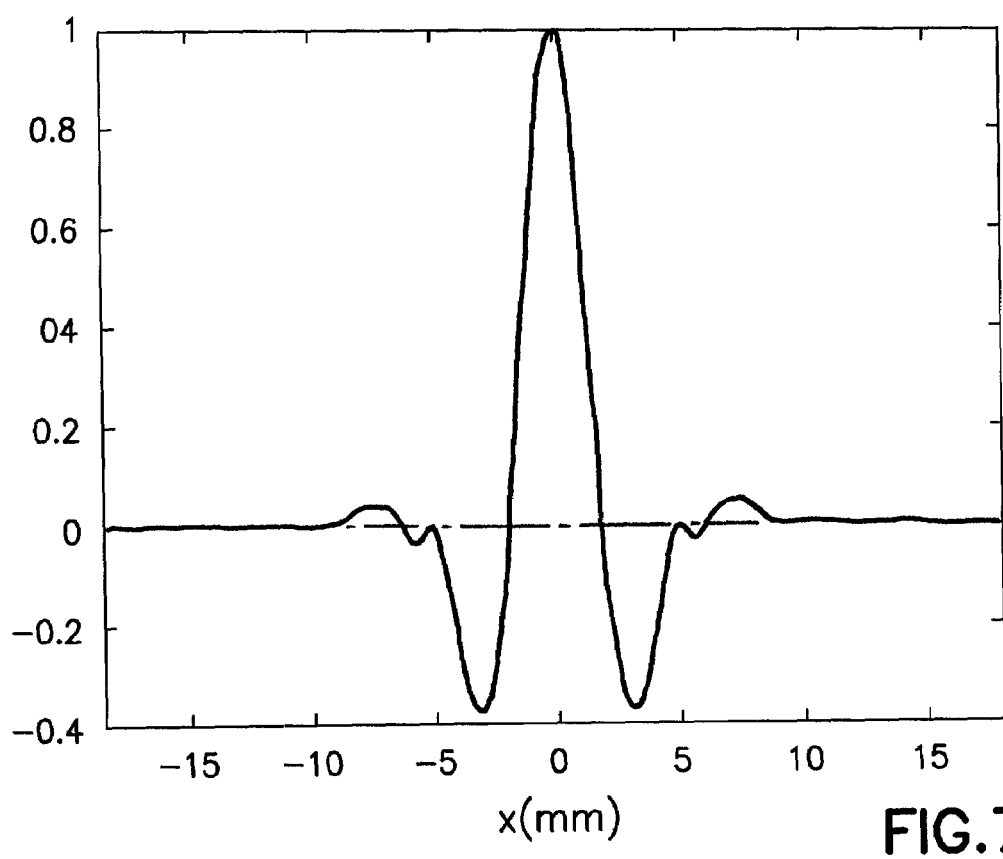

According to another embodiment, $m_1$ and $m_2$ may be frequency dependent. This frequency dependence, and thus the spectrum of the resulting echoes may be calculated. The results are illustrated in FIGS. 7A-H. In each figure, the solid line represents the real part and the dashed line represents the imaginary part. FIGS. 7A, 7C, 7E and 7G illustrate theoretical calculations of the signal shapes in the time domain, and FIGS. 7B, 7D, 7F and 7H illustrate corresponding theoretical calculations of the signal shapes (spectra) in the frequency domain. These theoretical signal shapes are obtained from a discrete isochromat simulation of a rectangular object whose size exceeds the slice width of the RF pulses. FIGS. 7A and 7B illustrate the calculated signal shape of a saturation recovery (SR) pulse sequence (see FIG. 6A) in the time and frequency domains, respectively. FIGS. 7C and 7D illustrate the signal shapes for a fast inversion recovery (FIR) sequence (see FIG. 6B) in the time and frequency domains, respectively. FIGS. 7E and 7F illustrate the calculated signal shapes for the decay component of FIR/SR decomposition in the time and frequency domains, respectively. Lastly, FIGS. 7G and 7H illustrate the calculated signal shapes for the decay component of SPARLM decomposition in the time and frequency domains, respectively.

Figure 8A:
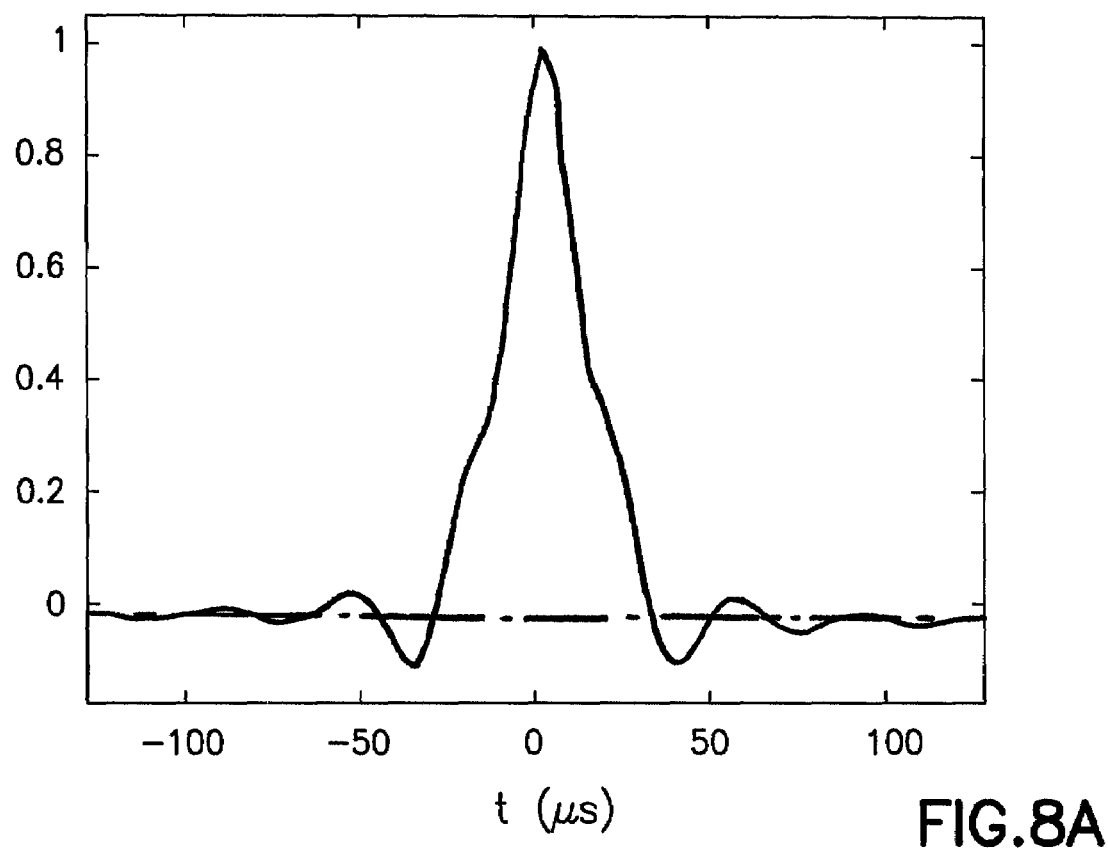
FIGS. 8 A-D are illustrations of example signal shapes using a sample containing tap water (Sample A) in the time domain (FIGS. 8A, 8C) and frequency domain (FIGS. 8B, 8D) for the same set of pulse sequences as used in FIGS. 7A-H.
Figure 8B:
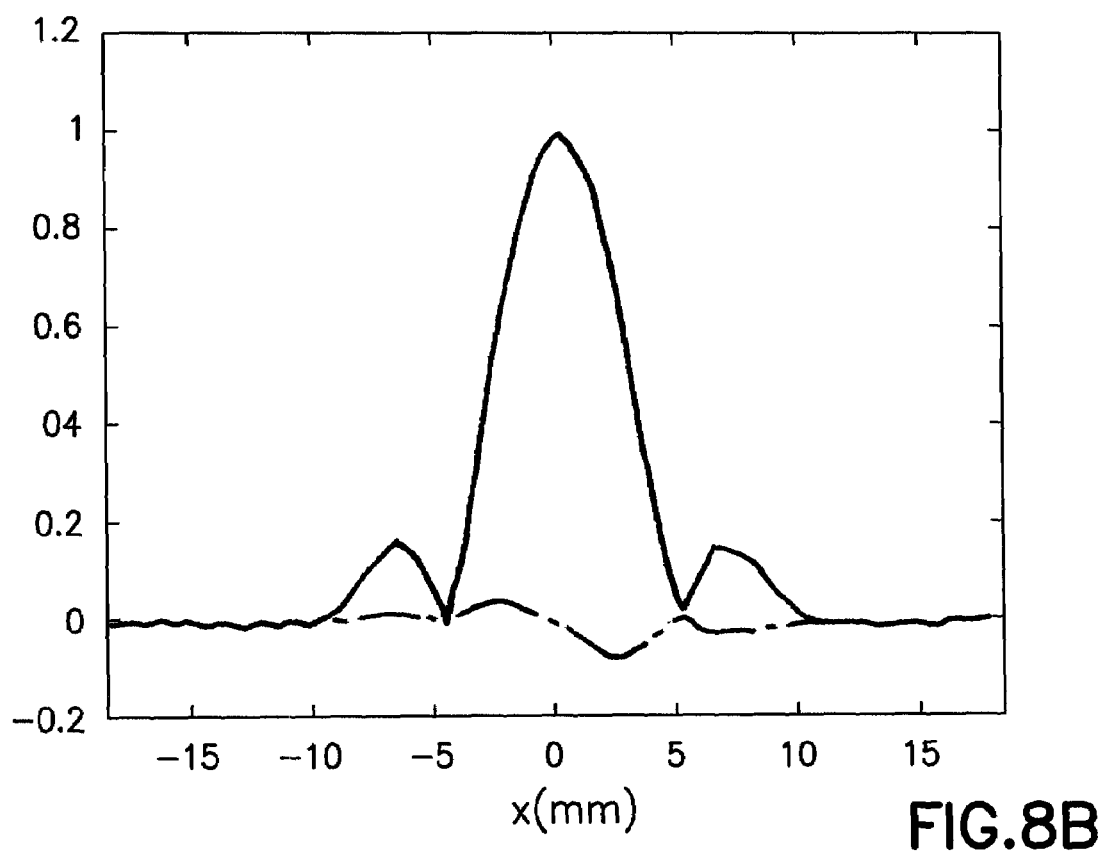
Figure 8C:
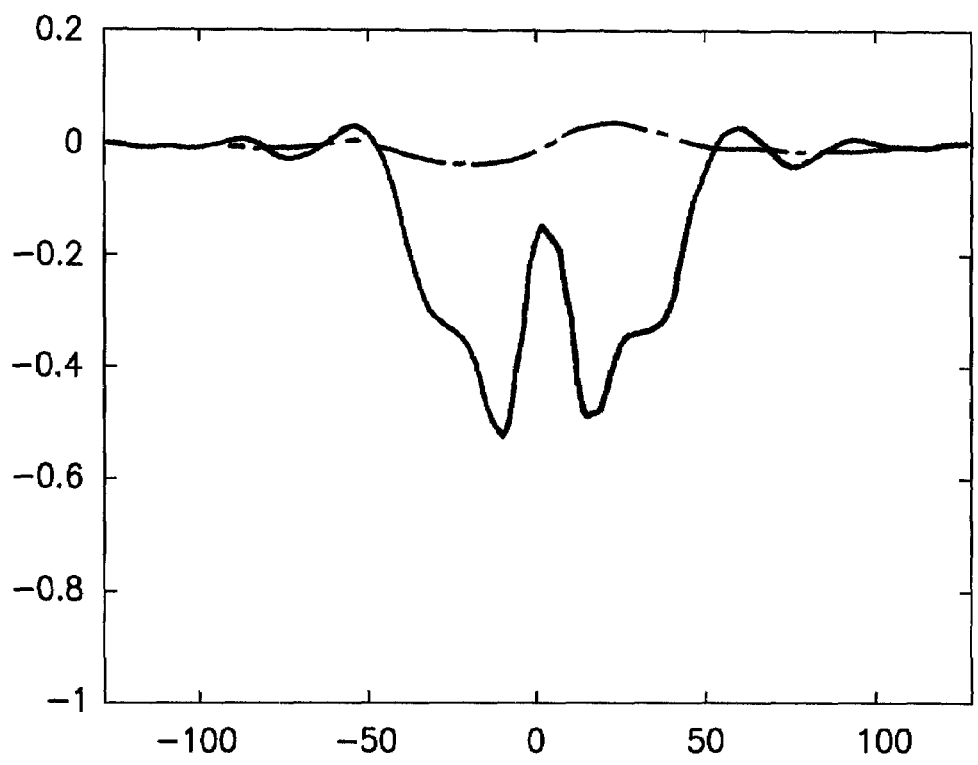
Figure 8D:
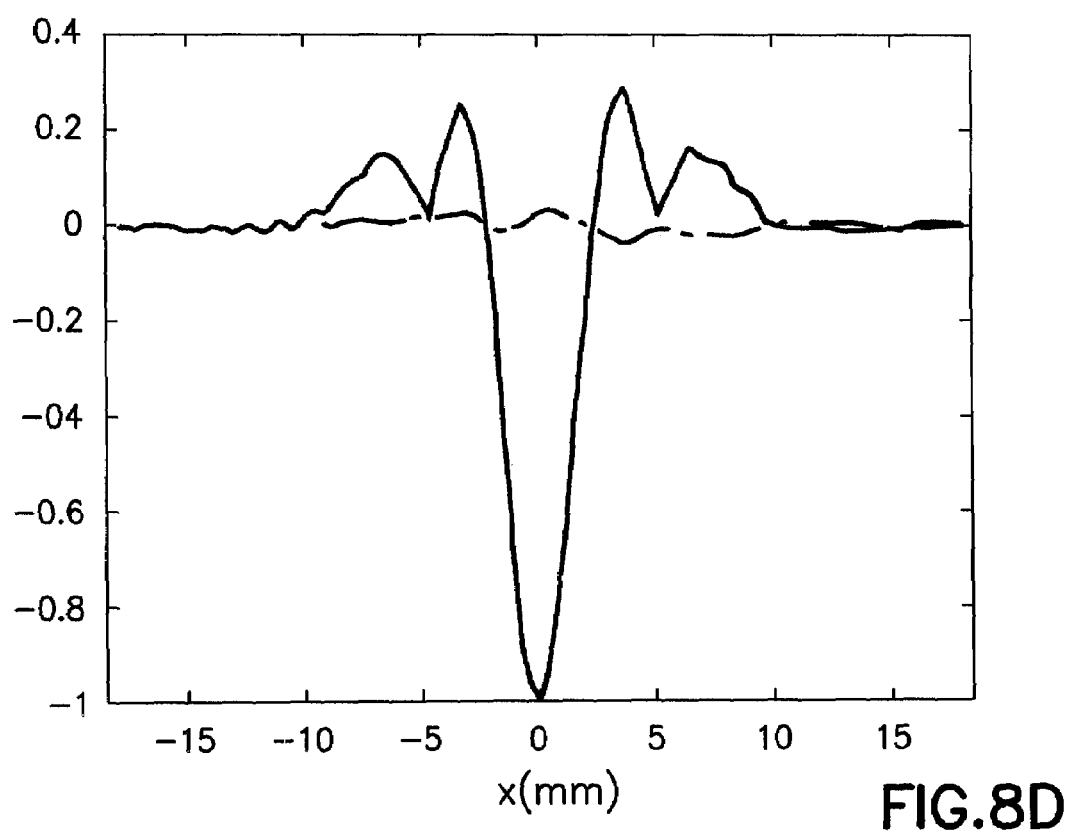

To verify these theoretical calculated echo shapes, an NMR example was performed on a sample in the fringe field of a Nalorac 2 T superconducting magnet (available from Nalorac Cryogenics) along the axis of the magnet using a TecMag Apollo spectrometer (available from TecMag, Houston, TX). The Larmor frequency was 1.7 MHz and the static field gradient was 13 G/cm. RF pulse widths of $t_{\pi/2}$=15.6 μs (for the 90° pulses) and $t_\pi$=31.2 μs (for the 180° pulses) were used. In one example, the sample was a 37 mm ID cylinder and contained tap water, which has a $T_1$ approximately equal to 2.5 s. This sample is referred to herein as Sample A. The field gradient was oriented along a diameter of the cylinder so that the resonant slice (thickness approximately 5 mm) was a slab oriented along the length of the cylinder. Referring to FIGS. 8A-D there are illustrated measured echo shapes for obtained for Sample A using the same signals for which the theoretical shapes were calculated and illustrated in FIGS 7A-H. Again, the solid lines represent the real part and the dashed lines represent the imaginary part. FIGS. 8A, 8C illustrate the measured signal shapes in the time domain and FIGS 8B, 8D illustrate the corresponding measured signal shapes in the frequency domain. Thus, FIGS. 8A and 8B illustrate the measured signal shape of the saturation recovery (SR) pulse sequence (see FIG. 6A) in the time and frequency domains, respectively. FIGS. 8C and 8D illustrate the measured signal shapes for the fast inversion recovery (FIR) sequence (see FIG. 6B) in the time and frequency domains, respectively.

Figure 9A:
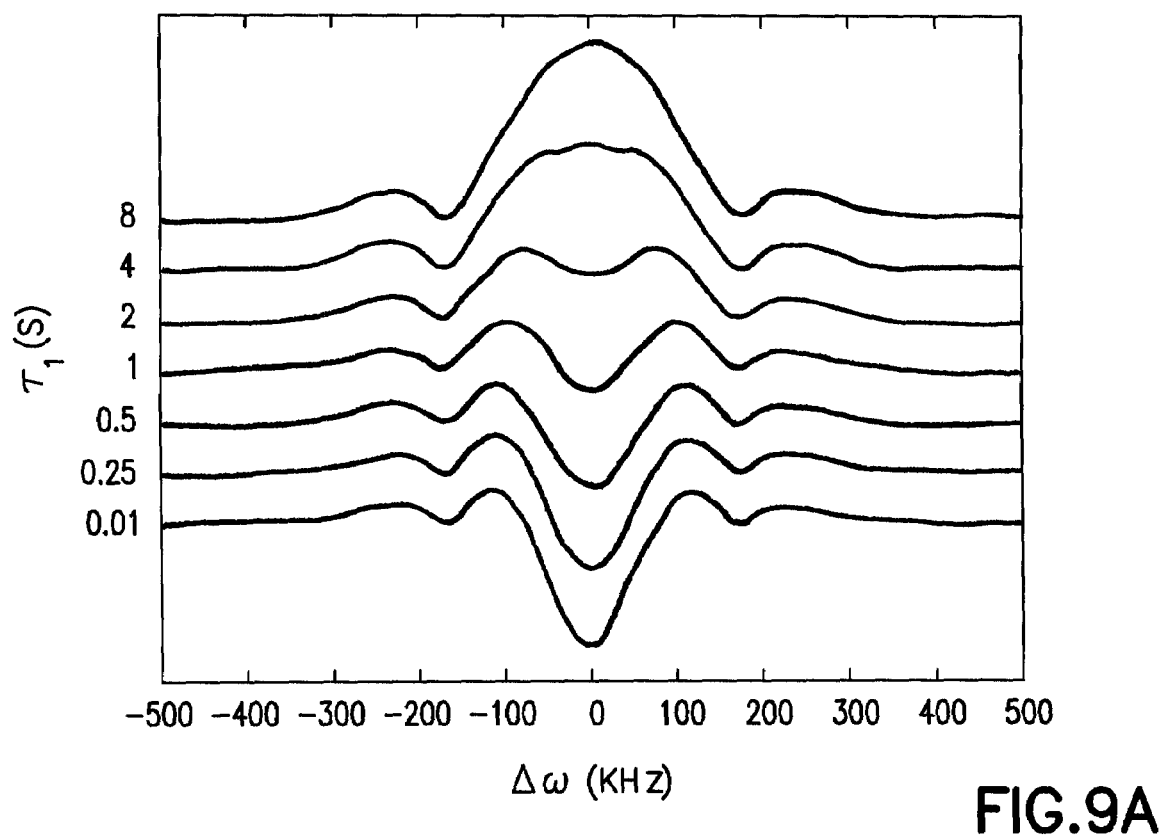
FIGS. 9A-D are illustrations of the time dependence of measured spectra for decomposition examples using Sample A.
Figure 9B:
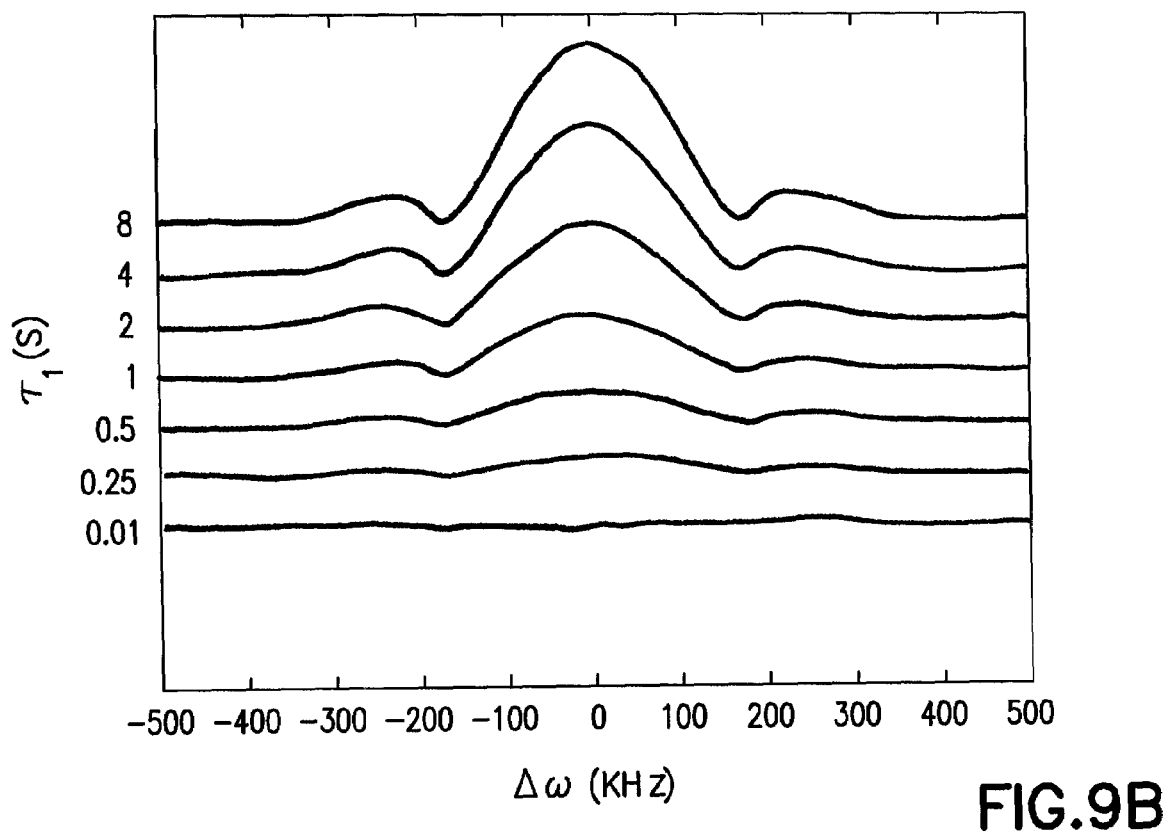
Figure 9C:
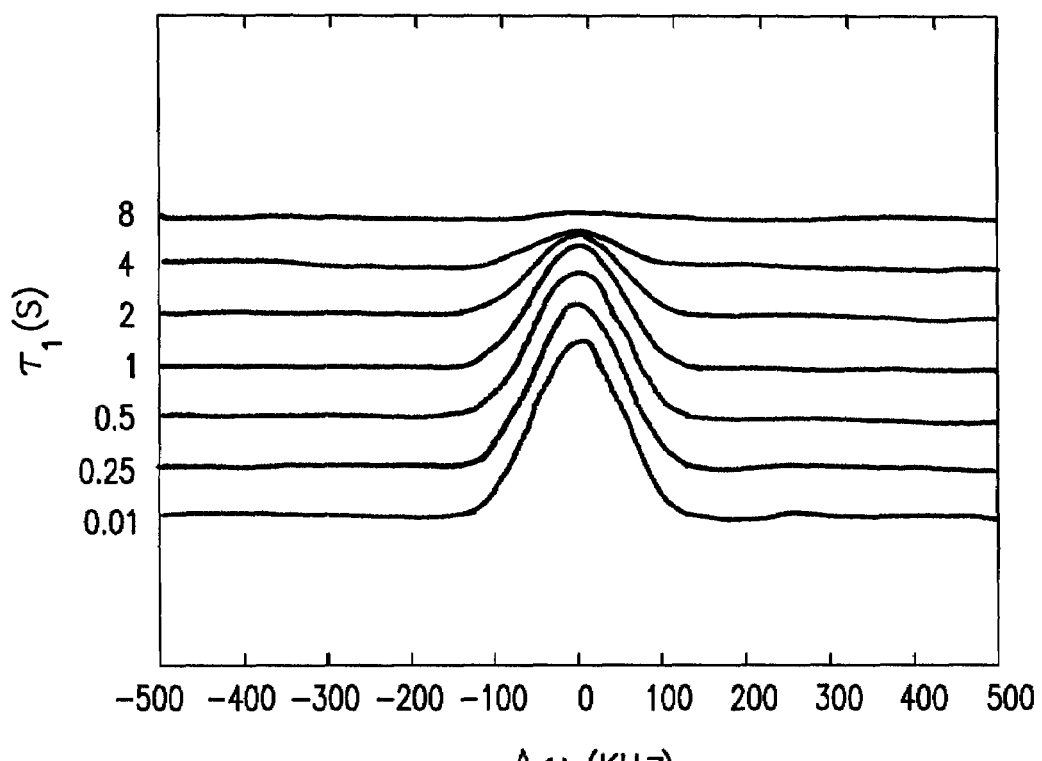
Figure 9D:
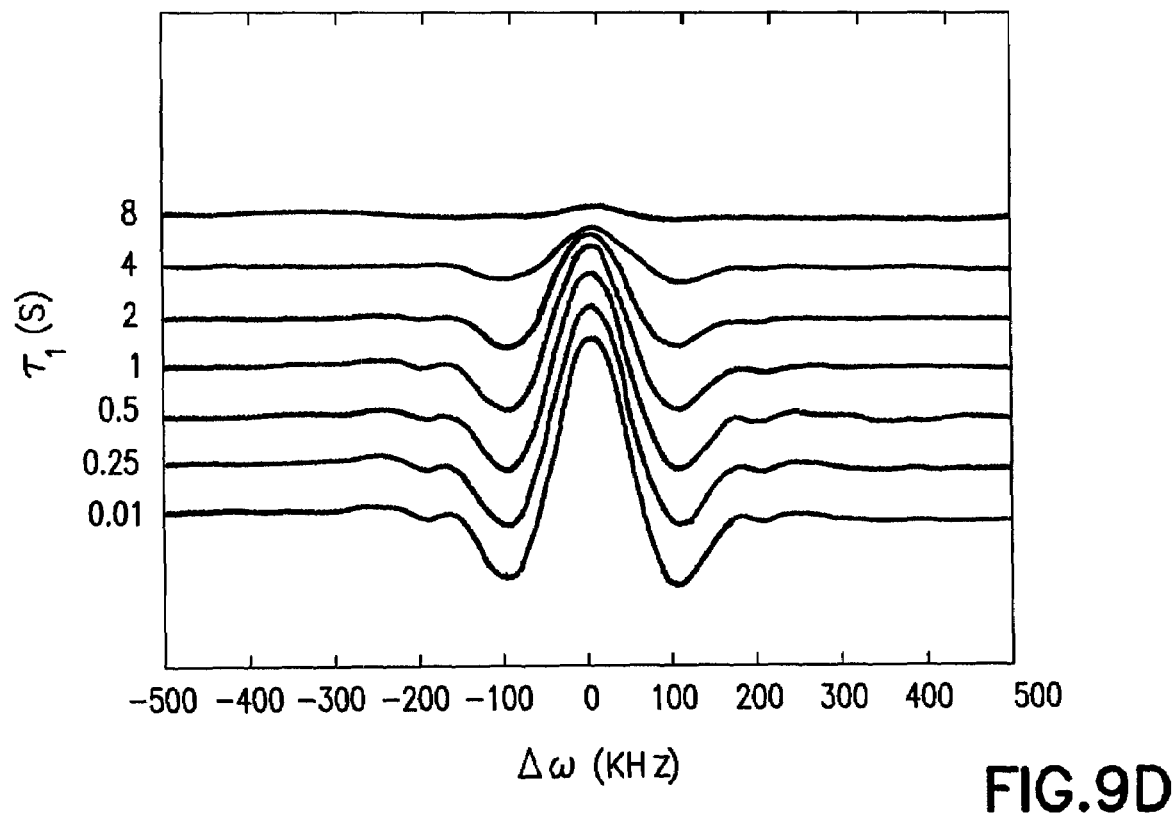

Referring to FIGS. 9A-D, there is illustrated the time dependence of the example spectra taken for Sample A for the set of pulse sequences discussed above. Frequency domain data are shown as a function of longitudinal magnetization evolution time, $\tau_1$, with logarithmic spacing between spectra. All data in this example were acquired for a fringe field frequency of 1.7 MHz and a static field gradient of 13 G/cm. FIGS. 9A, 9B and 9C illustrate the results from a FIR/SR decomposition example. Specifically, FIG. 9A illustrates FIR spectra and FIG. 9B illustrates SR spectra. FIG. 9C illustrates FIR/SR decay component spectra. As can be seen from FIGS. 9A and 9C, the decomposition process may isolate the region of the spectrum that has been perturbed by the inversion. In other words, the decomposition separates the "hole" from the background spectrum. This hole then decays via $T_1$ relaxation without substantial change in shape, as shown in FIG. 9C. FIG. 9D illustrates the decay component of the SPARLM example. Qualitatively, this shape shares the time-independent quality of the decay component of the FIR/SR sequence, but shows some additional structure from the multiple pulses involved in the SPARLM inversion sequence. This illustrates the possibility of more complicated inversion profiles while retaining the speed of the $T_1$ decomposition technique.

Having discussed several signal shapes for $T_1$ decomposition examples, there are now presented some examples that illustrate the potential speed of $T_1$ measurement that these signal shapes may provide. As mentioned above, one advantage of a decomposition method according to aspects of the invention is the measurement of a simple decay curve which can be obtained with measurement times, $\tau_1$, significantly below the 3-5 $T_1$ range required for a recovery example.

Figure 11:
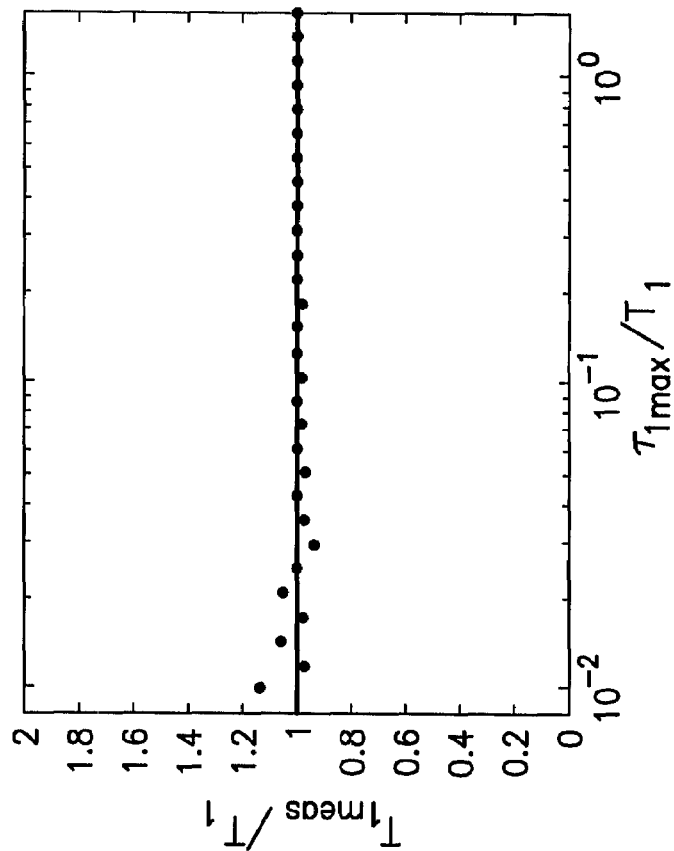
FIG. 11 is a plot of normalized measured $T_1$ values as a function of measurement range.
Figure 10:
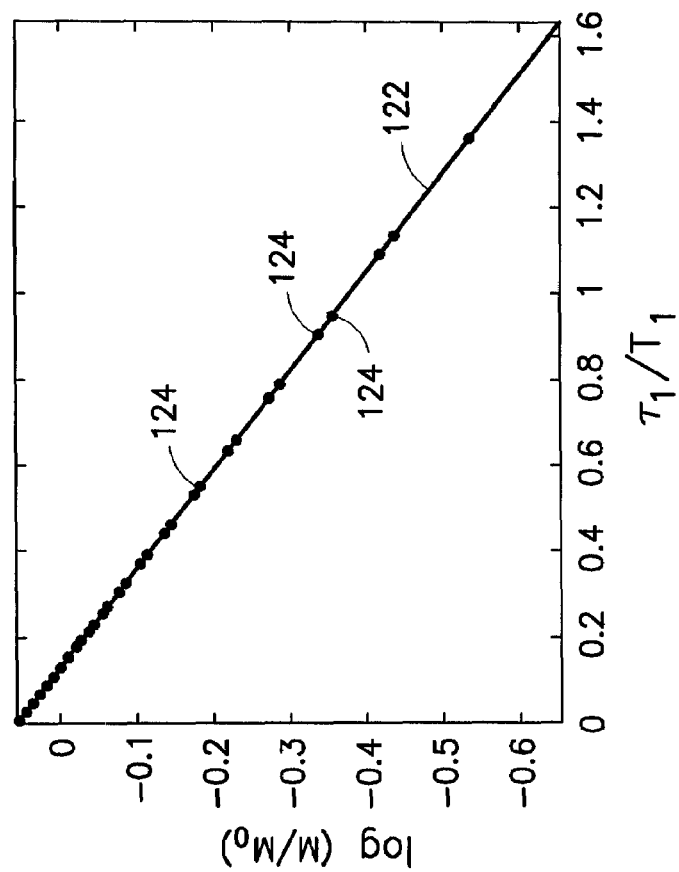
FIG. 10 is a plot of $T_1$ fit accuracy as a function of measurement range

In one example, the SPARLM method was tested with Sample A (a water sample) which exhibits a single relaxation time, $T_1$, of approximately 2.5 s. A set of SPARLM examples was performed on Sample A placed in a field gradient of 13 G/cm. Each example included four measurement points, $\tau_1$, over a range of measurement time. Referring to FIG. 10, there is illustrated a single exponential fit $M=M_0\exp(-\tau_1/T_1)$ for $T_1$ measurement accuracy as a function of measurement range to the complete data set. The solid line 122 represents the fit and a solid dots 124 represent measured data points. Referring to FIG. 11, there are illustrated measured $T_1$ values (normalized to an expected $T_1$ value of 2.5 s) as a function of the upper limit of each four-point data range, $\tau_{1max}$. Accurate results (within 5%) were observed for measurement times as short as approximately 0.05 $T_1$.

Two-dimensional relaxation examples were performed using both SPARLM and conventional saturation-recovery sequences to demonstrate an advantage of using SPARLM in measuring the long $T_1$ components in a mixture. In a first example, the sample used referred to herein as Sample B, contained two separate water compartments with different $T_1$ values of 2.5 s and 0.1 s. In a second example, the sample used, referred to herein as Sample C, included a water saturated Berea sandstone rock in one compartment and tap water in another compartment. The tap water was diluted with unprotonated deuterium oxide ($D_2O$) to make its contribution to the magnetization comparable to that of the water-saturated rock. The Berea rock possesses a distribution of relaxation times over the approximate range: 10 ms<$T_1$<1 s, owing to its distribution of pore sizes and the dominant surface relaxation mechanism.

For Sample B, SPARLM2d examples (i.e., using a two-dimensional (2d) SPARLM sequence) were performed with a series of $\tau_1$ delays detected by 2000 echoes (using CPMG detection). SR examples (i.e., using the SR sequence) were also performed on the Sample B with the same $\tau_1$ list and echo number. Two-dimensional Laplace transforms using a fast Laplace inversion (FLI) algorithm were performed to obtain two-dimensional $T_1$-$T_2$ spectra in three cases for the two types of examples (SPARLM2d and SR) separately. Three different analysis cases were used, having different $\tau_1$ lists with a maximum $\tau_1$ ($\tau_{1max}$) of 1, 0.0251 and 0.063 seconds, respectively. As stated above, the long $T_1$ component in Sample B is 2.5 s and thus, the three cases correspond to $\tau_1/T_1$ values of 0.4, 0.1 and 0.0025. In order to focus upon measurement rather than prepolarization effects, $\tau_0$ was set conservatively to 3 s. These examples illustrate the ability of the two types of pulse sequences (SPARLM2d and SR) to detect the long $T_1$ component with progressively shortened recovery time $\tau_1$.

Figure 12B:
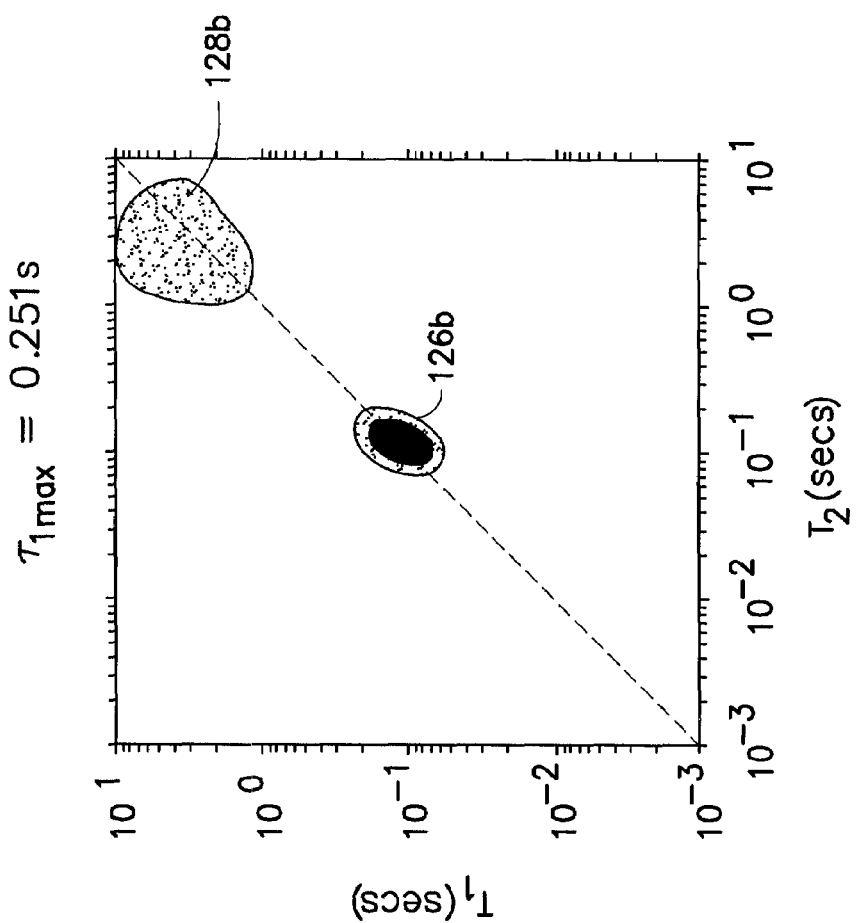
FIGS. 12A-C are $T_1$-$T_2$ maps from examples performed on a composite water sample (Sample B) using a SPARLM2d pulse sequence.
Figure 12A:
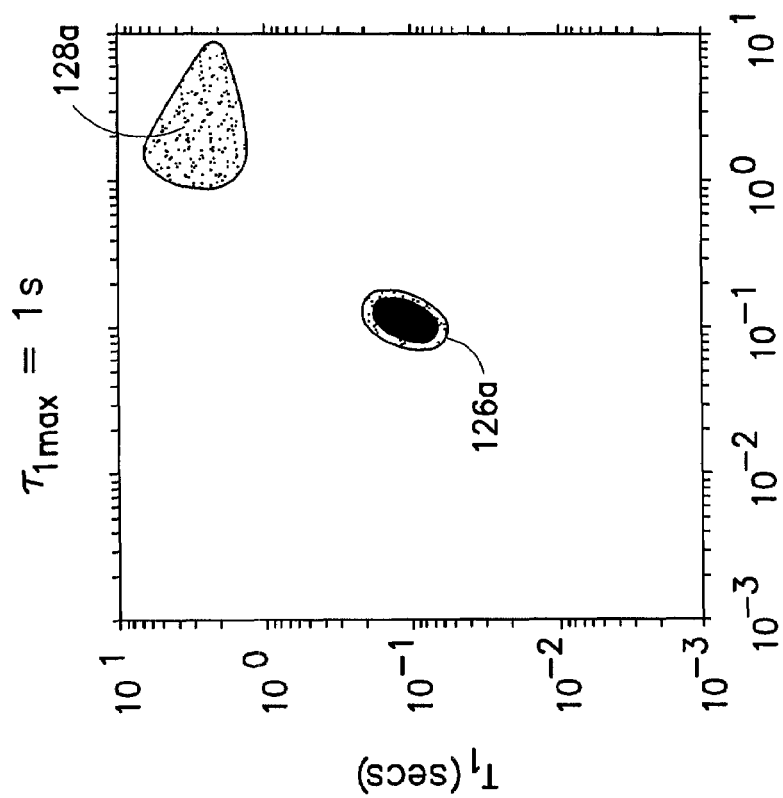
Figure 12D:
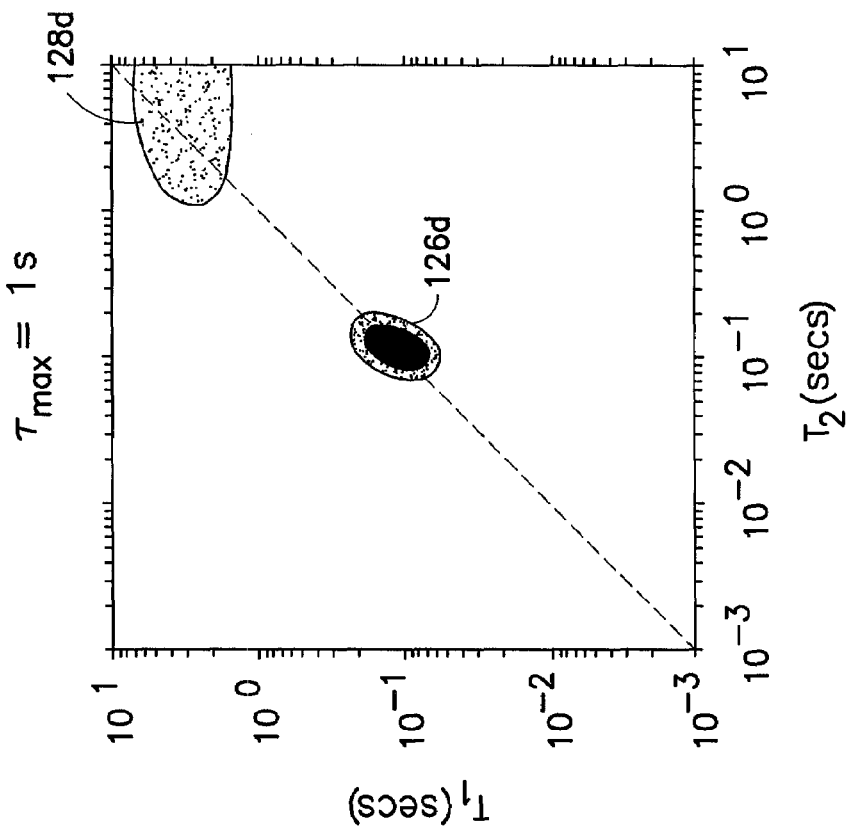
FIGS. 12D-F are $T_1$-$T_2$ maps from examples performed on Sample B using an SR pulse sequence.
Figure 12C:
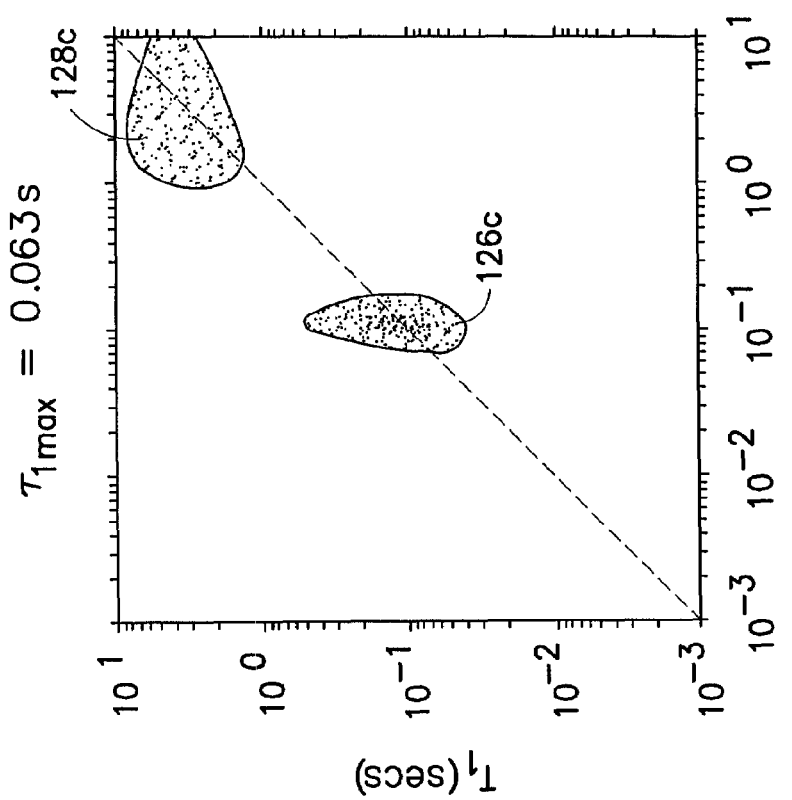
Figure 12F:
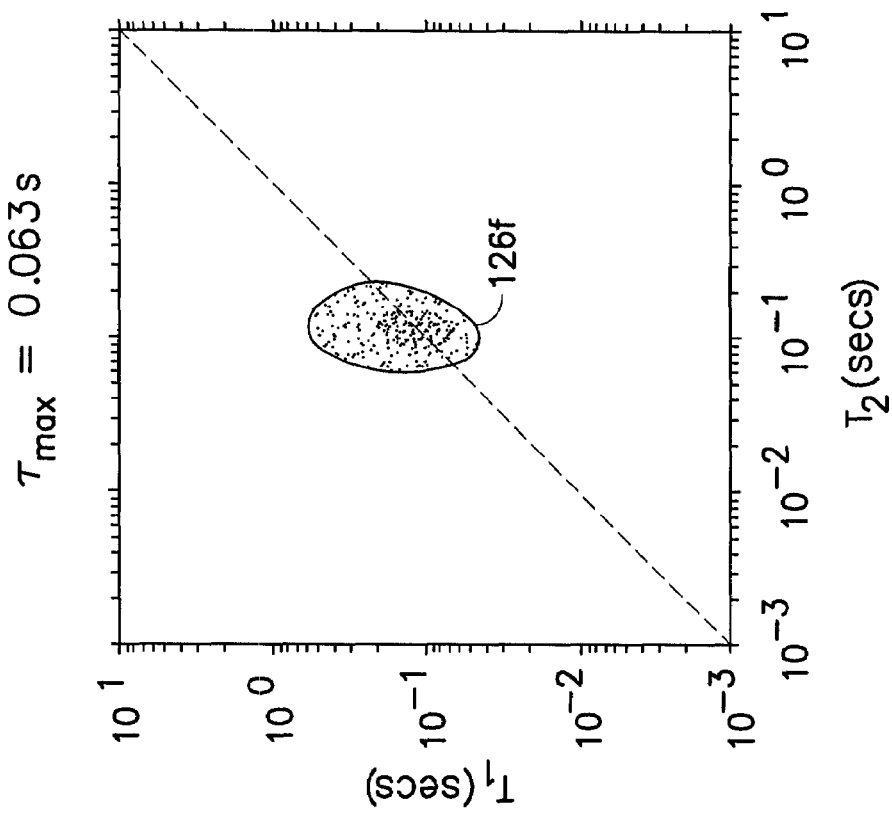
Figure 12E:
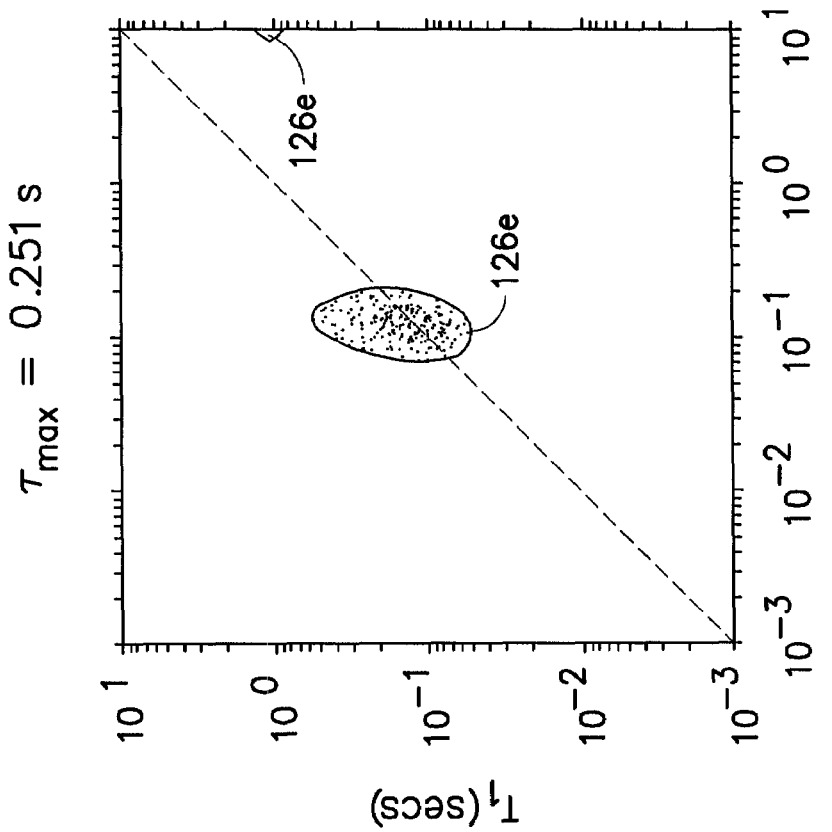

Referring to FIGS. 12A-F, there are illustrated the resulting two-dimensional $T_1$-$T_2$ spectra from these examples and analysis for Sample B. FIGS. 12A-C illustrate the results from the SPARLM2d examples and FIGS. 12D-F illustrate the results from the SR examples. In each figure, three contours of the distribution have been drawn if present in the data. The values of these contours are the same in each of FIGS. 12A-F and were chosen to be 10%, 50% and 90% of the maximum signal in the SPARLM2d distribution for $\tau_{1max}$=1 s. FIG. 12A illustrates the distribution from the SPARLM2d example with $\tau_{1max}$=1 s. FIG. 12B illustrates the distribution from the SPARLM2d example with $\tau_{1max}$=0.251 s. FIG. 12C illustrates the distribution from the SPARLM2d example with $\tau_{1max}$=0.063 s. FIG. 12D illustrates the distribution from the SR example with $\tau_{1max}$=1 s. FIG. 12E illustrates the distribution from the SR example with $\tau_{1max}$=0.251 s, and FIG. 12F illustrates the distribution from the SR example with $\tau_{1max}$=0.063 s. In each case, $T_1$ is represented on the vertical axis and $T_2$ is represented on the horizontal axis, both in units of seconds. In each figure, the intensity of the longer $T_1$ peak includes, at most, the 10% contour, and in some cases, none at all (FIGS. 12E,F).

Referring to FIG. 12A, two peaks 126a, 128a centered at $T_1$=0.1 s and $T_1$=3 s, respectively, are clearly visible. Similar peaks 126d and 128d, also approximately centered at $T_1$=0.1 s and $T_1$=3 s are visible in FIG. 12D. A comparison of FIG. 12A and FIG. 12D shows that the spectra are fairly similar in the appearance of both peaks, indicating that both examples are capable of measuring the longer $T_1$ at a recovery time $\tau_{1max}=1$ s. The relative broadening of the long $T_1$ peaks 128a,d is due to insufficient recovery time, $\tau_1$, range compared to the long $T_1$ component. As noted above, in the examples corresponding to FIGS. 12A and 12D, $\tau_{1max}$ is approximately equal to 0.4 times the long $T_1$ component. These results illustrates that, at the longest recovery time, both sequences work well and the SPARLM results are slightly better (less broadening of the peaks indicates a more accurate measurement). FIGS. 12B and 12E were obtained with $\tau_{1max}=0.251$ s, which is only one tenth of the long $T_1$ component. Comparing FIGS. 12A and 12B, it can be seen that the long $T_1$ peak 128b is further broadened compared to the peak 128a in FIG. 12A. However, it retains similar signal amplitude and location along both the $T_1$ and $T_2$ axes. In contrast, the spectrum from the SR example, illustrated in FIG. 12E, shows a long $T_1$ peak 128e with reduced amplitude and shifted position ($T_{1,apparent}=1$ s). The shorter $T_1$ peak 126e is also significantly affected and shows a large broadening along the $T_1$ (vertical) dimension. These results indicate that, at the shorter recovery time, the SPARLM sequence performs significantly better and may yield a more accurate $T_1$ measurement. FIGS. 12C and 12F, obtained with $\tau_{1max}=0.063$ s, only 0.0025 times the long $T_1$ component, demonstrate an even more dramatic comparison between the two sequences. In the SR example (FIG. 12F), the long $T_1$ peak is completely absent and even the short $T_1$ peak 126f is significantly affected. In contrast, the SPARLM example, data (FIG. 12C) still shows a clear separation between the two $T_1$ peaks 126c, 128c without drastic change in either their location or amplitude. Thus, these examples demonstrate that the SPARLM sequence decomposition technique discussed above is useful for measuring long relaxation times without requiring long measurement time.

Figure 13B:
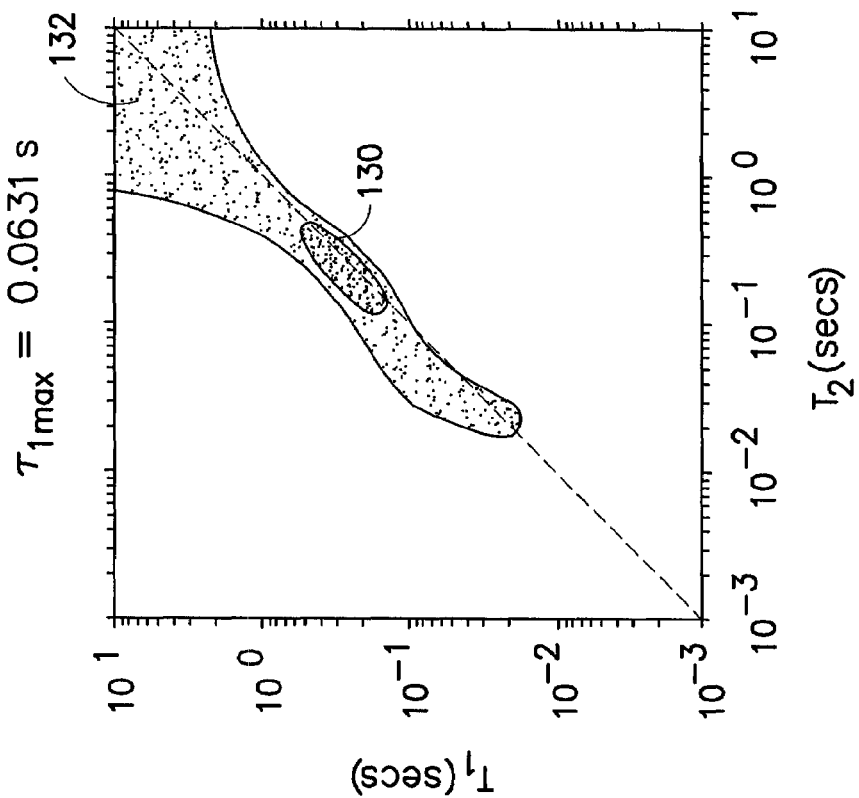
FIGS. 13A-C are $T_1$-$T_2$ maps from examples performed on a composite water and rock sample (Sample C) using a SPARLM2d pulse sequence.
Figure 13A:
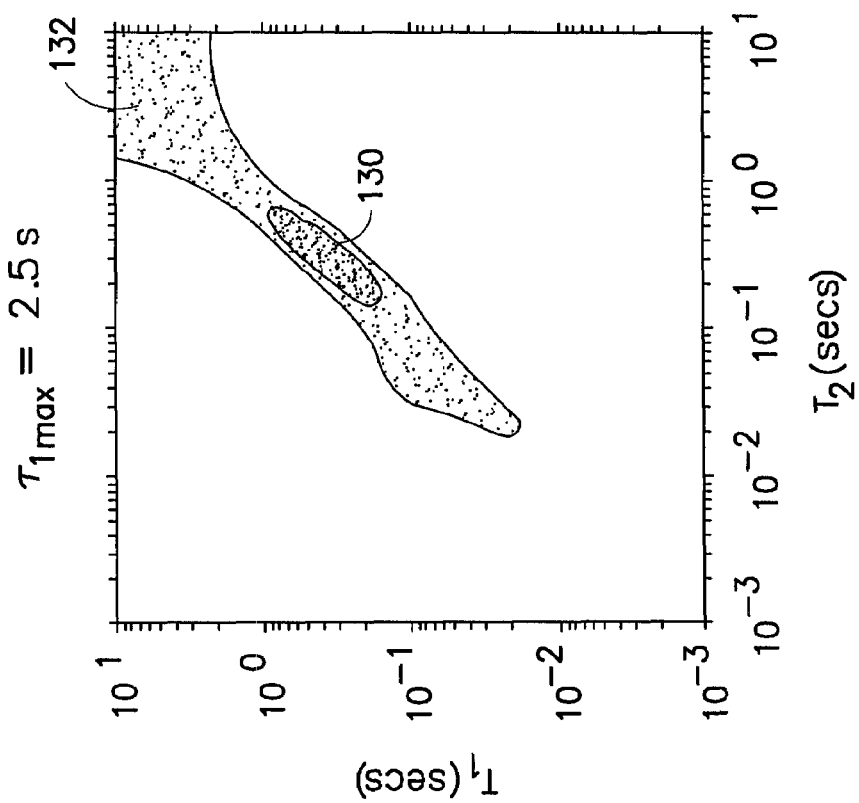
Figure 13D:
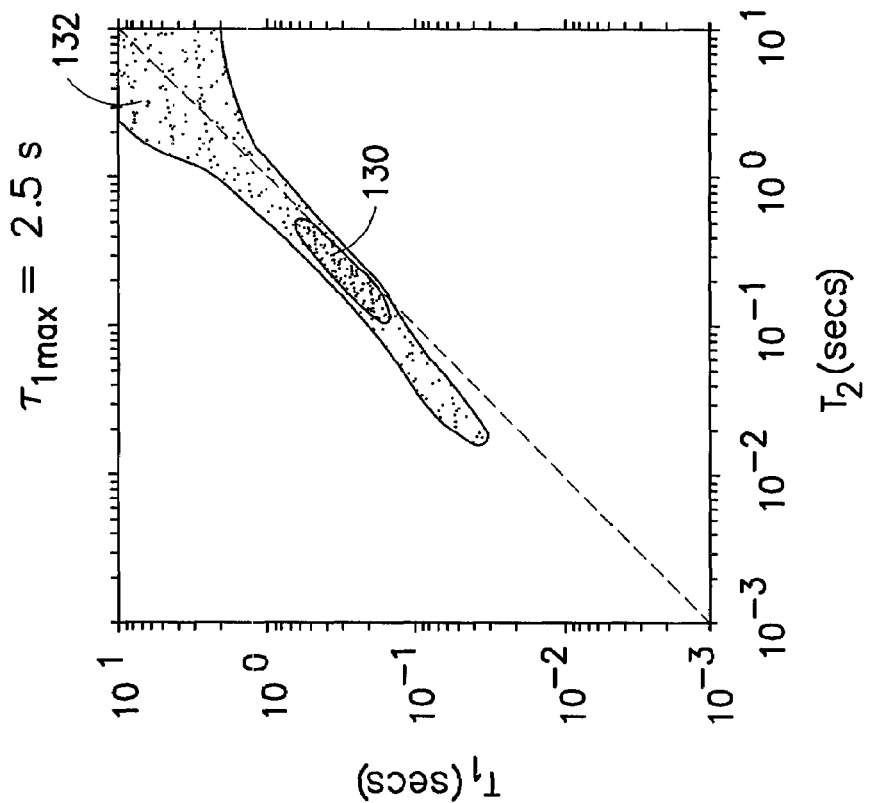
FIGS. 13D-F are $T_1$-$T_2$ maps from examples performed on Sample C using an SR pulse sequence.
Figure 13C:
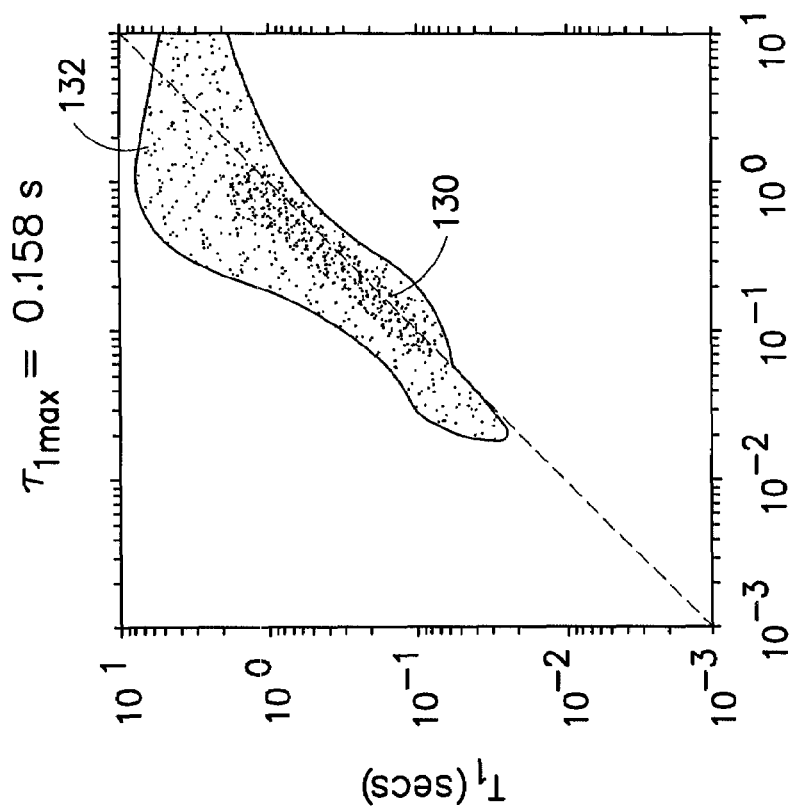
Figure 13F:
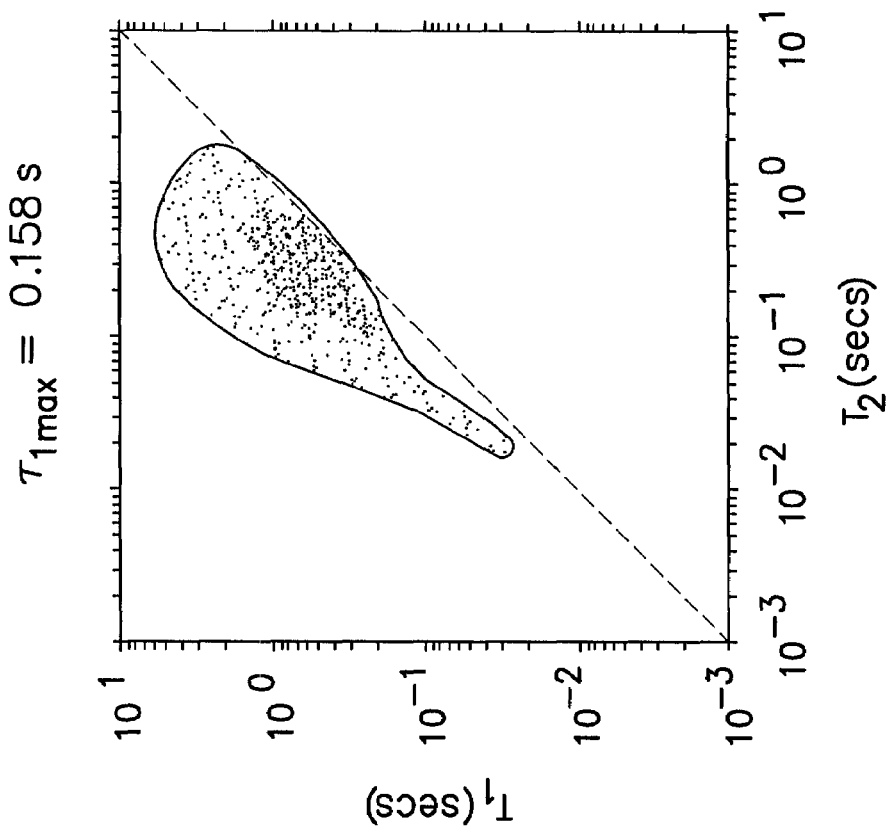
Figure 13E:
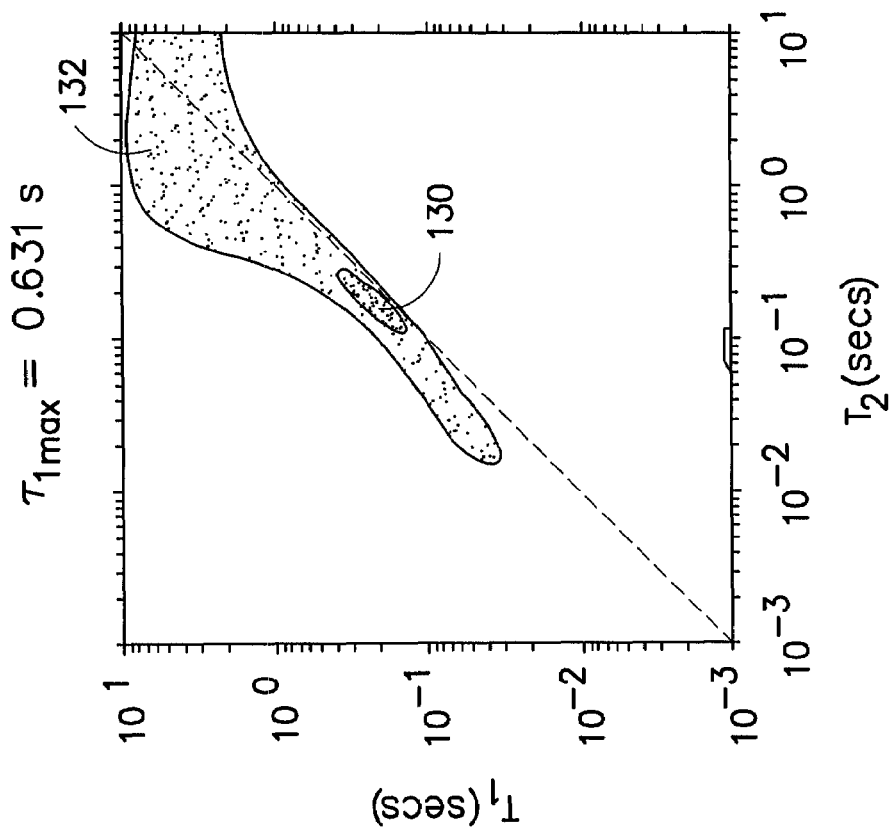

Examples using Sample C were also performed analogously to those described above using Sample B. In the Sample C series of examples, the measurement time limits employed were $\tau_{1max}=2.5$ s, 0.631 s, and 0.158 s, with a prepolarization time, $\tau_0$, of one second. FIGS. 13A-13F illustrate the resulting relaxation spectra from these examples. The contours displayed are the same for each figure and (if present) are at 10%, 50% and 90% of the maximum signal in the SPARLM2d distribution for $\tau_{1max}=2.5$ s. FIGS. 13A, 13B and 13C illustrate the distributions obtained from the SPARLM2d examples and FIGS. 13D, 13E and 13F illustrate the distributions obtained from the saturation recovery examples. As was the case for the Sample B data, the SPARLM2d spectra are more robust than are the saturation recovery spectra as a function of shortened measurement time $\tau_{1max}$. In all the SPARLM2d spectra, the signal 130 from the water confined in the Berea sandstone can be qualitatively distinguished from the free tap water signal 132 at the long relaxation time region of the spectrum. It is noted that the signal 130 shows a distribution of relaxation times due to surface relaxation from a range of pore sizes in the rock. In contrast, in the saturation recovery examples, the two signals are completely indistinguishable for $\tau_{1max}=0.158$ s=0.5 $T_{1,water}$ (FIG. 13F) while some separation between them still exists in the data from the SPARLM2d sequence (FIG. 13C). The SPARLM examples show less distortion with shortening of the measurement time, $\tau_{1max}$, and retains sensitivity to the longest $T_1$ component (i.e., from the tap water). These results show the applicability of SPARLM2d to more realistic samples containing a range of relaxation times, as is ubiquitous among water and oil-saturated rocks.

As discussed above, according to some aspects of the invention, improved $T_1$ measurements may be achieved through the decomposition of the measured echo shape into two components, the decay component and the recovery component. According to one embodiment, for any value of recovery time, the example echo shapes may be decomposed into a weighted sum of $s_r(t)$ and $s_d(t)$:

$$S_y(t) = a_r s_r(t) + a_d s_d(t) \tag{16}$$

Given the echo shapes $s_r(t)$ and $s_d(t)$, the amplitudes $a_r$ and $a_d$ can be extracted from a measured echo shape $S(t)$ by the following equations:

$$a_d = \frac{(s_d \cdot S)(s_r \cdot s_r) - (s_d \cdot s_r)(s_r \cdot S)}{(s_d \cdot s_d)(s_r \cdot s_r) - (s_d \cdot s_r)(s_r \cdot s_d)} \tag{17}$$

$$a_r = \frac{(s_r \cdot S)(s_d \cdot s_d) - (s_r \cdot s_1)(s_d \cdot S)}{((s_d \cdot s_d)(s_r \cdot s_r) - (s_d \cdot s_r)(s_r \cdot s_d))} \tag{18}$$

where: $(s_d \cdot S) = \int dt s^*_d(t) S(t)$ and other similar terms are integrals over the acquisition window.

The relative sizes of these amplitudes may be directly related to the longitudinal relaxation time by the equation:

$$\frac{a_d}{a_d + a_r} = \exp\{-\tau/T_1\} \tag{19}$$

Thus, by decomposing the signal into the decay and recovery components, as discussed above, and solving for the amplitudes, $T_1$ may be directly calculated from a measured echo shape.

In one embodiment, it may be preferable that the decomposition of the echo shape can be performed even with data of limited signal-to-noise ratio (as is often the case with data collected in grossly inhomogeneous fields). It may be particularly preferable if the components are orthogonal (or nearly orthogonal) to each other. In other words, the magnitude of the cross term $(s_d \cdot s_r)$ may be minimized, while keeping $(s_d \cdot s_d)$ and $(s_r \cdot s_r)$ as large as possible. For the standard CPMG sequence shown in FIG. 1, the two echo shapes (see FIGS. 2A and 2B) have a strong overlap and are far from orthogonal to each other. Quantitatively, the normalized cross term in this case is:

$$(s_d \cdot s_r)/\sqrt{(s_d \cdot s_d)(s_r \cdot s_r)} = -0.625 \tag{20}$$

This corresponds to an angle of approximately 129 degrees.

The general approach to the decomposition may not depend on the details of the pulses used. Therefore, it may be possible to improve the performance of the sequence of FIG. 1 by using more sophisticated pulses, such as composite pulses, frequency- or amplitude-modulated pulses, or the pulse sequences discussed above. In one embodiment, a pulse sequence may be designed such that the two components (i.e., the decay component and the recovery component) are substantially orthogonal. As discussed further below, in one embodiment, this may be achieved by designing the pulse sequences such that the different coherence pathways form echoes at different times. In another embodiment, orthogonality may be created by generating signals that are out of phase with one another. Although, in general, this may not be possible in the frequency domain because the refocusing pulses refocus only a single component in grossly inhomogeneous fields, it is possible in the time domain. For example, a decaying signal may be generated that is substantially anti-symmetric with respect to the offset frequency, $\omega_0$, and a recovering signal that is symmetric with respect to $\omega_0$. In this case, the two signals will form out of phase in the time domain. This may be achieved by using an inversion pulse that generates a longitudinal magnetization anti-symmetric with respect to the offset frequency, $\omega_0$.

Figure 14:
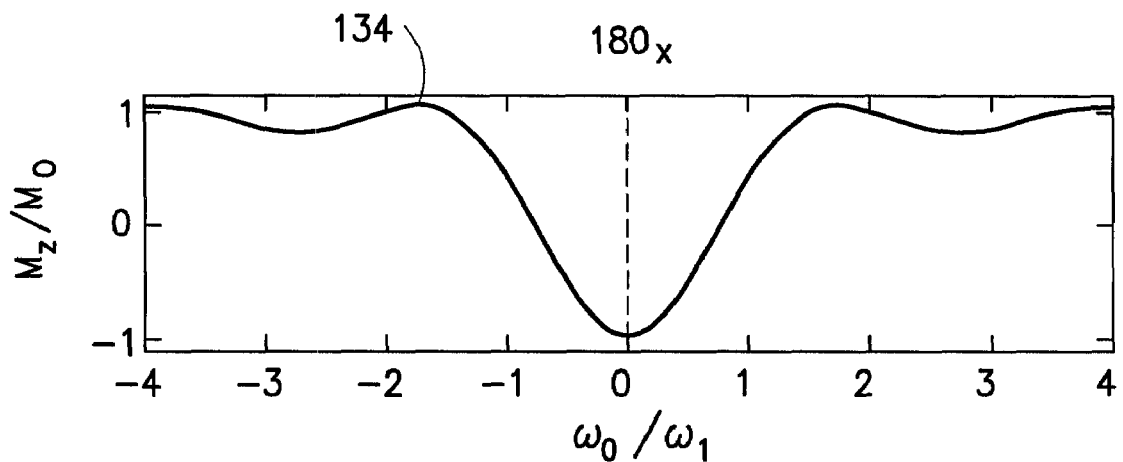
FIG. 14 is a plot of the calculated spectrum of the longitudinal magnetization after the initial 180° pulse produced by a standard inversion recovery CPMG sequence.

The standard 180° inversion pulse 100 shown in FIG. 1 generates a symmetric profile in the longitudinal magnetization, as shown in FIG. 14. As can be seen in FIG. 14, the magnetization 134 is clearly symmetric about $\omega_0/\omega_1$. According to one embodiment, a solution to create an anti-symmetric spectrum may include using a composite pulse sequence of the form:

$$127°_x - t_{90} - 127°_{\pm y} \quad (21)$$

Figure 15:
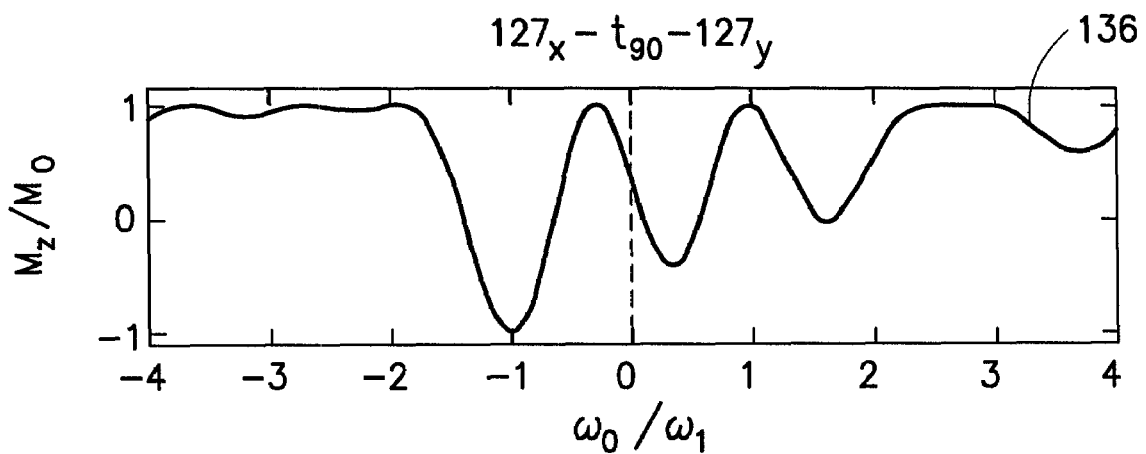
FIG. 15 is a plot of the calculated spectrum of the longitudinal magnetization after the initial inversion pulses produced by a modified inversion recovery CPMG sequence, according to an embodiment of the invention.

In this embodiment, two nominal 127° pulses (of duration $\sqrt{2}$ times longer than the nominal 90° pulse, $t_{90}$) are separated by a time, $t_{90}$, of free precession. This composite pulse may generate a large anti-symmetric component within $\pm 2\omega_1$ (where $\omega_1$ is the RF nutation frequency) of the offset frequency. In one example, at $\omega_0 = \pm \omega_1$, the resulting longitudinal magnetization is $\pm M_0$. In other words, in this example, the maximum magnitude is anti-symmetric with respect to frequency. FIG. 15 shows the longitudinal magnetization after the composite inversion pulse described by expression (21). It can be seen that this magnetization 136 is not symmetric about $\omega_0/\omega_1$. It is to be appreciated that other techniques may also be used to generate anti-symmetric spectrums and that the invention is not limited to the use of the example described above. For example, another means by which to create an anti-symmetric spectrum includes use of the half-adiabatic-fast-passage.

According to one embodiment, to refocus the magnetization produced by the preparation pulse sequence of expression (21), an off-resonance CPMG sequence may be used having the form:

$$127_x - (t_E/2 + \tau_a) - (127_x 127_{-x} - t_E)^N \quad (22)$$

where: $\tau_a = -t_{90}$.

With this sequence, the magnetization at $\pm \omega_1$ may be completely refocused. Thus, combining expressions (21) and (22), a modified inversion recovery CPMG sequence according to one embodiment of the invention may have the form:

$$(127°_x - t_{90} - 127°_{\pm y}) - \tau - (127_x - (t_E/2 + \tau_a) - (127_x 127_{-x} - t_E)^N) \quad (23)$$

Figure 16:
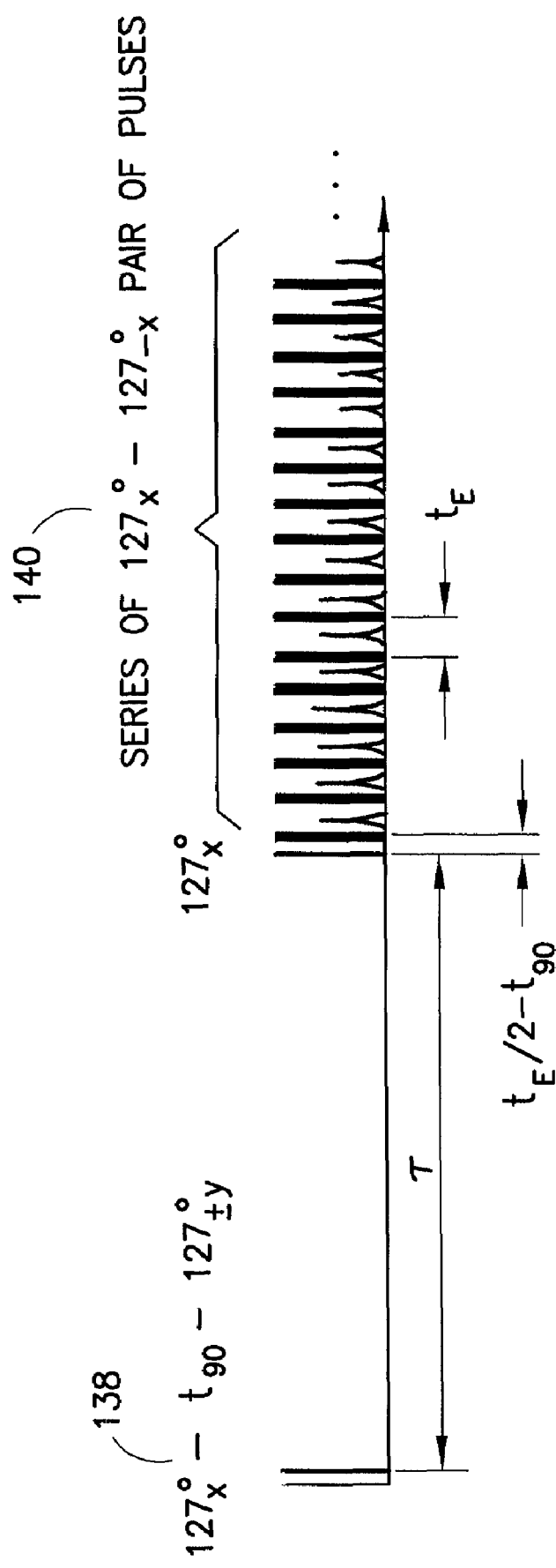
FIG. 16 is a timing diagram of a pulse sequence according to an embodiment of the invention.

An example of such a modified inversion recovery CPMG sequence is illustrated in FIG. 16. The sequence includes a composite inversion pulse 138, having the form described in expression (21), followed by a series 140 of refocusing pulses that begin after the recovery time, $\tau$, has elapsed, $t_E$ is the echo spacing, and $t_{90}$ and $t_{180}$ are the durations of nominal 90° and 180° pulses, respectively. With the phase of pulses and timing shown in FIG. 16, the spectrum of the decaying coherence pathway may be predominantly anti-symmetric with respect to $\omega_0$, whereas the spectrum of the recovering coherence pathway may be symmetric with respect to $\omega_0$.

Figure 17B:
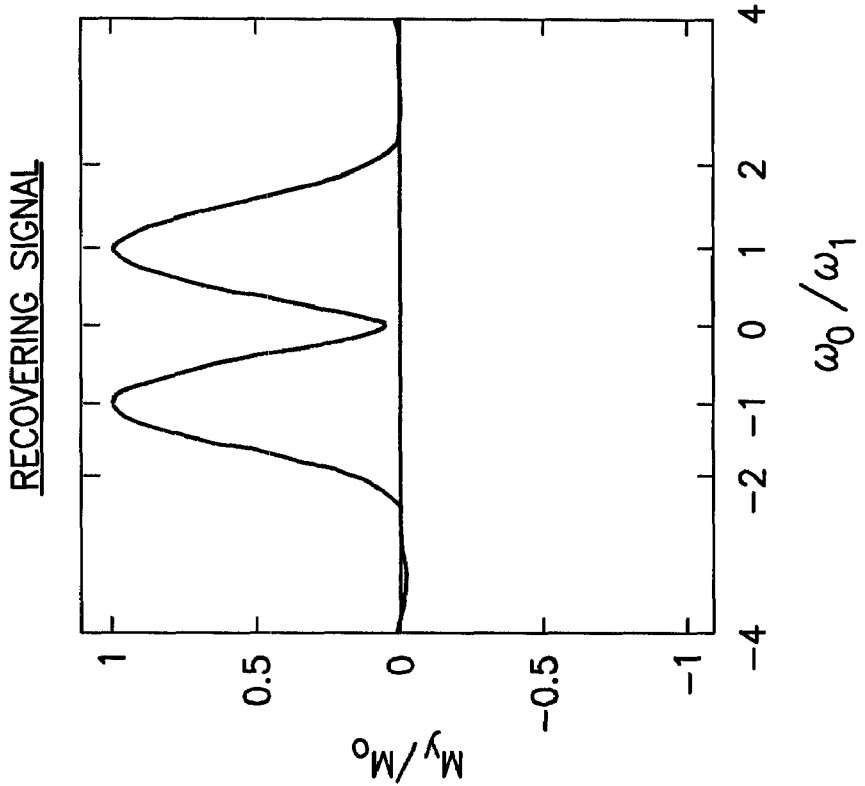
FIG. 17B is a plot of the spectrum of the recovering coherence-pathway for the same modified inversion recovery CPMG sequence according to an embodiment of the invention.
Figure 17A:
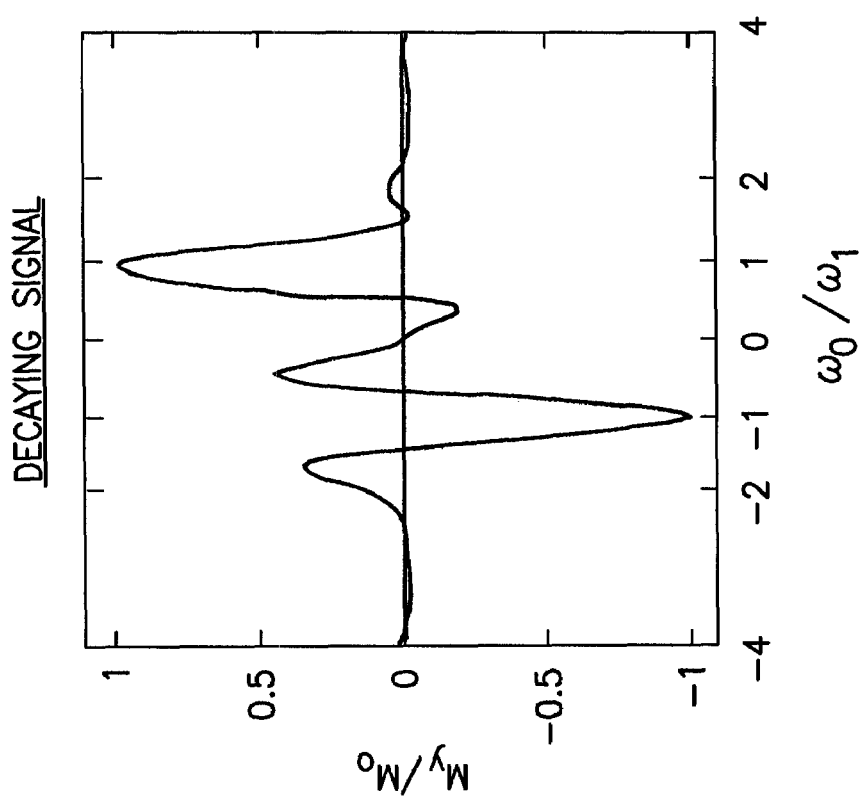
FIG. 17A is a plot of the spectrum of the decaying coherence pathway for a modified inversion recovery CPMG sequence according to an embodiment of the invention.
Figure 17D:
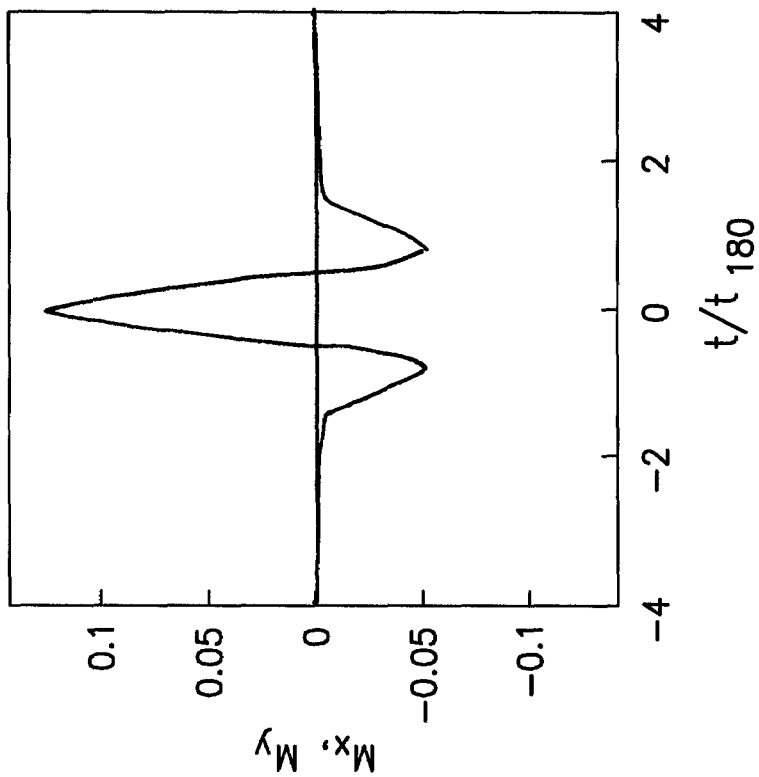
FIG. 17D is an illustration of the time domain echo shape for the recovering coherence pathway for the same modified inversion recovery CPMG sequence according to an embodiment of the invention.
Figure 17C:
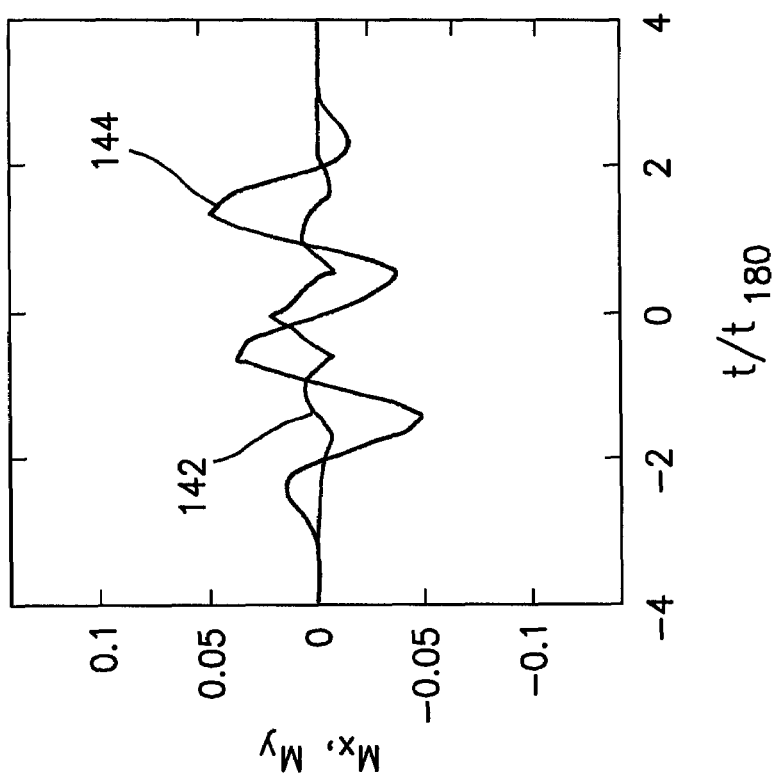
FIG. 17C is an illustration of the time domain echo shape for the decaying coherence pathway for the same modified inversion recovery CPMG sequence according to an embodiment of the invention

Referring to FIGS. 17A-D, there are illustrated calculated spectra and echo shapes from the pulse sequence described in expression (23). FIG. 17A illustrates the spectrum of the decaying coherence pathway for the modified sequence and FIG. 17B illustrates the spectrum of the recovering pathway. The spectra of both coherence pathways are in phase, but that of the recovering coherence pathway (see FIG. 17B) is symmetric with respect to the offset frequency, whereas that of the decaying coherence pathway (FIG. 17A) is mainly anti-symmetric. As a result, the signal in the time domain forms mainly out of phase for the recovering coherence pathway and mainly in phase for the decaying coherence pathway. The time domain echo shapes for the decaying coherence pathway and the recovering coherence pathway are illustrated in FIGS. 17C and 17D, respectively. In FIG. 17C, line 142 represents the in-phase component and line 144 represents the out-of-phase component. The smaller in-phase component in the decaying coherence pathway may be caused by the residual symmetric component in the spectrum of this coherence pathway.

Figure 18A:
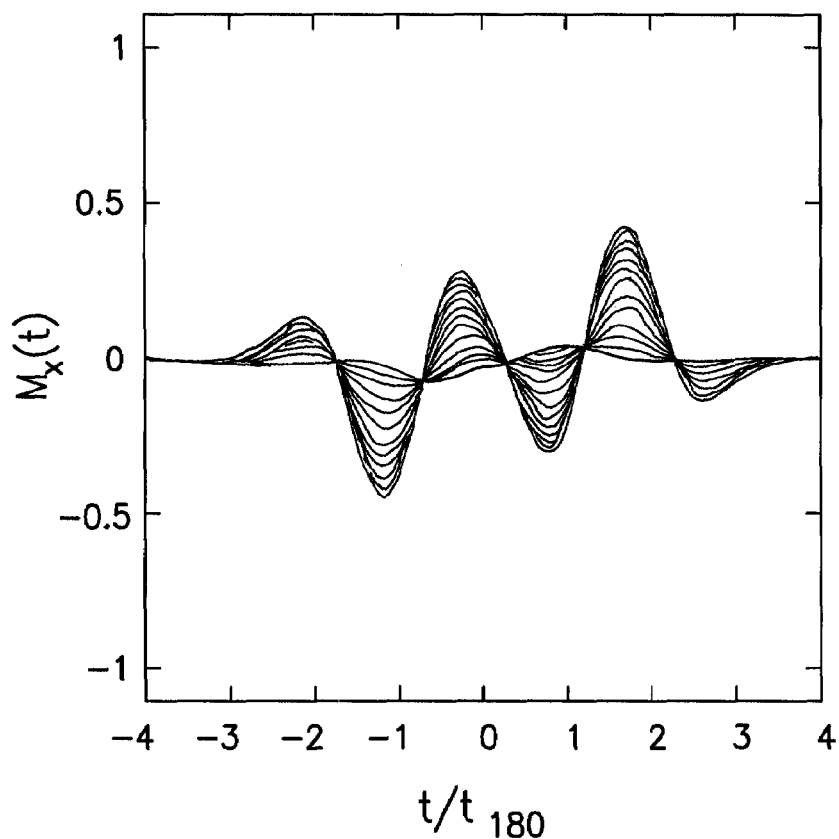
FIG. 18A is a plot of the in-phase component of example echo shapes with the modified pulse sequence according to an embodiment of the invention.
Figure 18B:
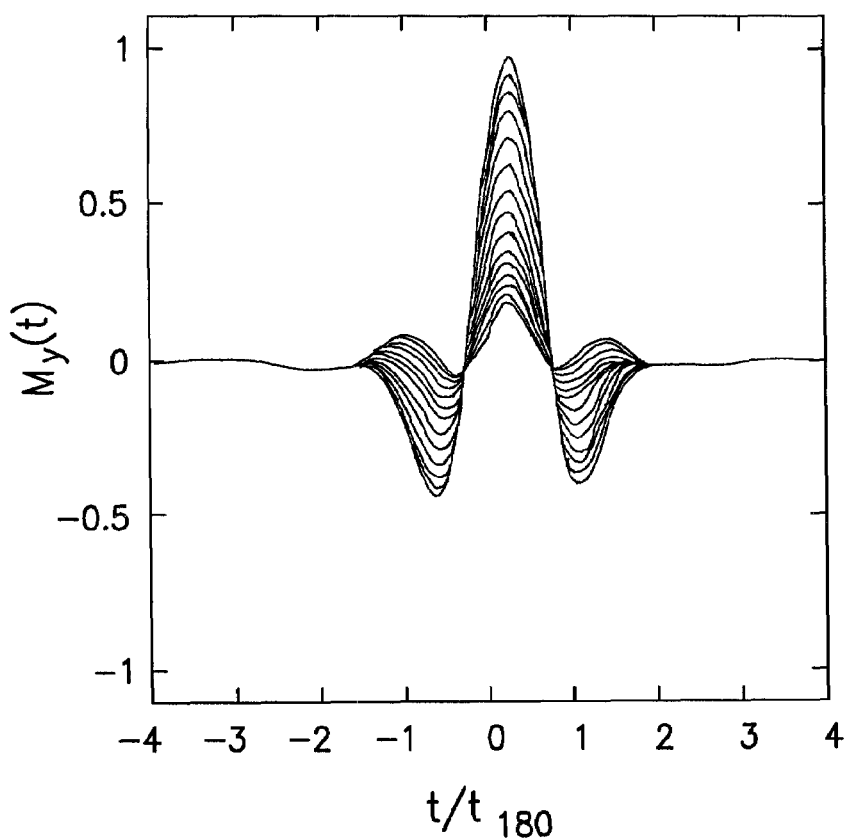
FIG. 18B, is a plot of the out-of-phase component of example echo shapes with the modified pulse sequence according to an embodiment of the invention.

To confirm the above calculations, an example was performed using the sequence described in expression (22). The echo shapes were extracted by averaging the $10^{th}$ to $110^{th}$ echo. FIGS. 18A and 18B illustrate example results of echo shapes with the modified pulse sequence according to an embodiment of the invention. In FIG. 18A, the in-phase component is illustrated and in FIG. 18B, the out-of-phase component is illustrated. The different shapes in each figure correspond to different values of recovery time, $\tau$. As can be seen by comparing FIGS. 18A and 18B to FIGS. 17C and 17D, the shapes agree well with the calculated results. When the recovery time, $\tau$, is increased, the out-of-phase signal decays, whereas the in-phase signal grows. The ratio of the out-of-phase to in-phase signal may be directly related to the relative size of the recovery time, $\tau$, to the relaxation time, $T_1$.

Figure 19:
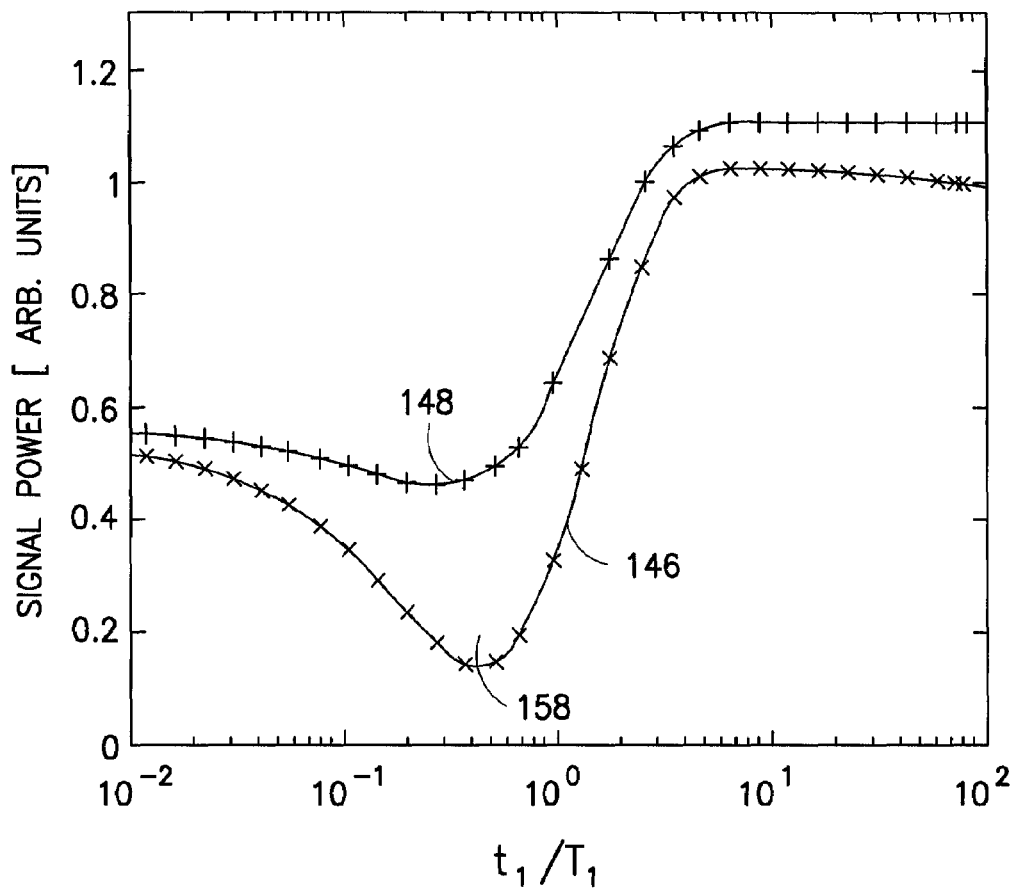
FIG. 19 is a plot of signal power (represented on the vertical axis) versus a ratio of the relaxation time, $T_1$, to the recovery time, $\tau$, (represented on the horizontal axis) for different pulse sequences.

In addition, the signal power of the two signals $s_r(t)$ and $s_d(t)$ may also be significantly increased. Referring to FIG. 19, there is illustrated a plot of signal power (represented on the vertical axis) versus a ratio of the relaxation time, $T_1$, to the recovery time, $\tau$, (represented on the horizontal axis) for different pulse sequences. Line 146 represents data from an example using the standard inversion recovery CPGM sequence (illustrated in FIG. 1) operated on resonance. Line 142 represents data from an example using the modified inversion recovery CPGM sequence described by expression (23). It can be seen that the modified inversion recovery CPMG sequence may generate signals that are of comparable amplitude, or slightly larger, as those of the standard sequence. With the standard sequence (se FIG. 1), there may be substantial cancellation between the signals of the two coherence pathways when the recovery time is close to log 2 $T_1$. This may lead to a pronounced dip 158 in the signal power of the CPMG echoes. This problem may be avoided with the modified sequence according to an embodiment of the invention because the two contributions may be predominantly out of phase and therefore do not cancel.

Figure 20:
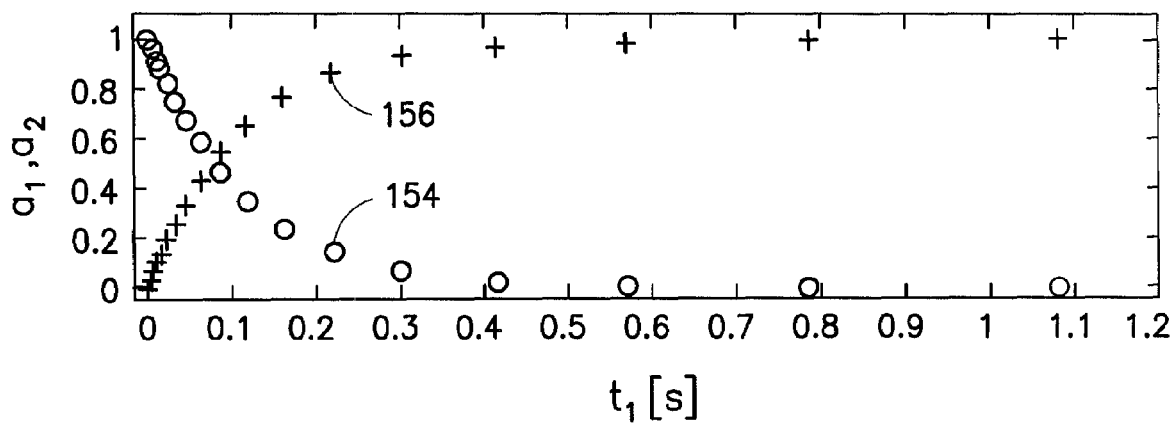
FIG. 20 is as plot of extracted amplitudes for the decaying coherence pathway and recovering coherence pathway.

The decomposition of the example echo shapes into the components of the two coherence pathways may still be described by equation (7). The amplitudes of the decay and recovery components may be extracted from the echo shapes shown in FIGS. 18A and 18B using equations (17) and (18). Referring to FIG. 20, there are illustrated the extracted amplitudes for the decaying coherence pathway (data set 154) and recovering coherence pathway (data set 156). There is excellent agreement with the expected exponential dependence on $\tau/T_1$.

The modified sequence according to an embodiment of the invention may not generate a perfectly anti-symmetric longitudinal magnetization after the inversion pulse. As a consequence, the decaying coherence pathway may generate a small in-phase component, as shown in FIG. 17C. In one embodiment, it may be possible to extract the purely anti-symmetric signal of this coherence pathway by phase cycling. For example, referring to FIG. 16, changing the phase of the second pulse in the sequence 138 from +y to -y may effectively invert the frequency axis. In other words, this change may only affect the anti-symmetric signal. If the signals generated by the two sequences are subtracted from one another, only the anti-symmetric, out-of-phase signal may contribute. This may result in an exact subtraction of the recovering signal over the whole spectrum.

The above-described composite pulse sequence may significantly improve the orthogonality of the two signals $s_r(t)$ and $s_d(t)$. In one example, the normalized cross term may be:

$$(s_d \cdot s_r)/\sqrt{(s_d \cdot s_d)(s_r \cdot s_r)} = 0.15 \quad (24)$$

This may be a significant improvement compared to the cross term value of −0.625 for the standard CPMG sequence discussed above.

With any $T_1$ sequence, the signal power will depend on the ratio of $T_1/\tau$. A robust single-shot method for extraction of porosity, $T_2$, and $T_1$ may require a weak dependence in order to allow acquisition over a wide range of parameters. With the standard inversion recovery CPMG operated on resonance, the decaying and recovery signals exactly cancel for $T_1 = \tau/\log 2$ and no additional information can be obtained. With the modified sequence, the dependence of the signal power on the ratio $T_1/\tau$ is much weaker, as shown in FIG. 10.

Figure 21:
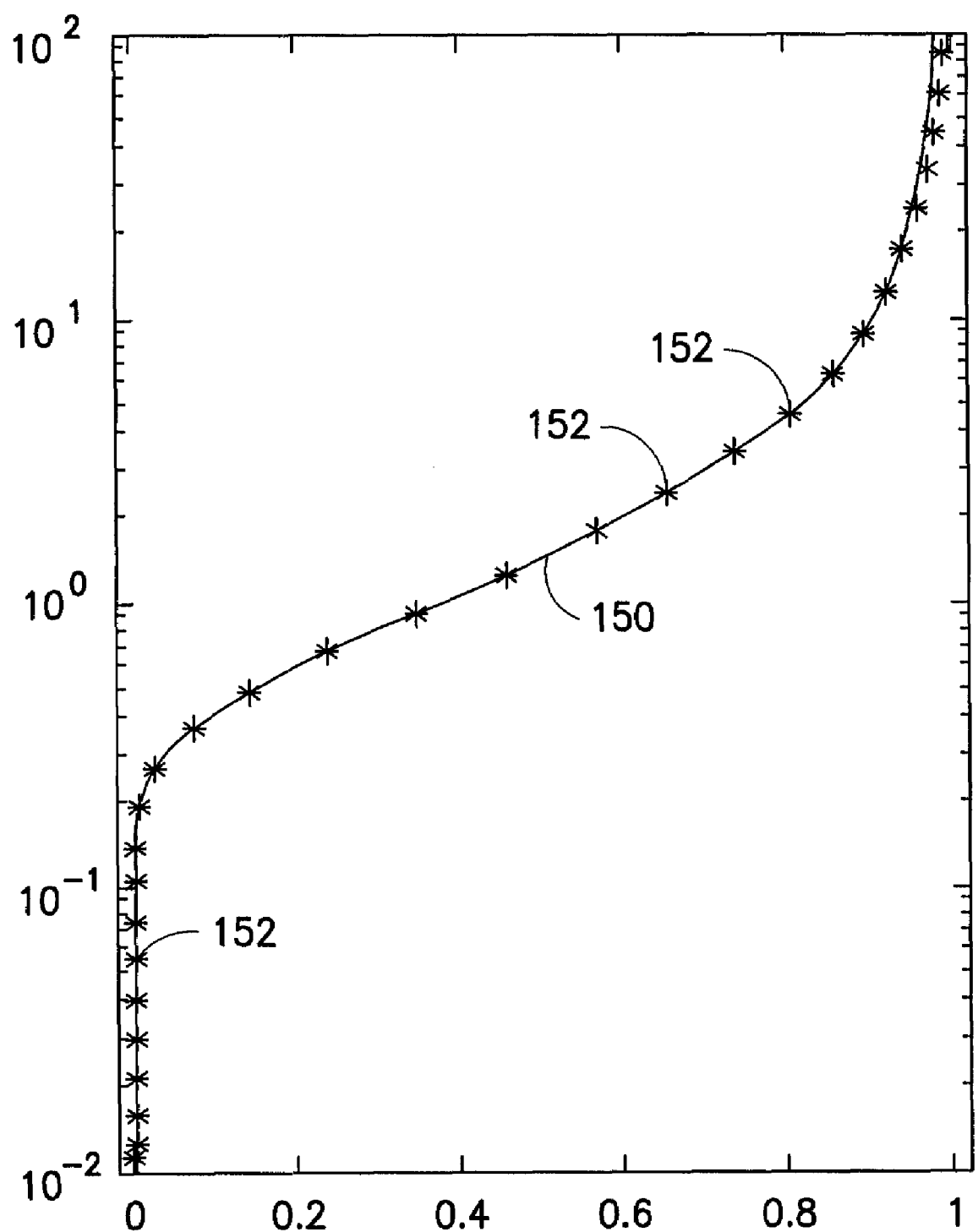
FIG. 21 is a plot of the relationship between the longitudinal relaxation time and the relative size of the amplitudes of the decaying and recovering coherence pathways.

As discussed above, the amplitudes of the $a_r$ and $a_d$ of the component signals can be extracted from a measured echo shape S(t) according to equations (17) and (18), and $T_1$ ay be found from the amplitudes according to equation (19). Referring to FIG. 20, there is illustrated the relationship between the longitudinal relaxation time, $T_1$, and the relative sizes of the amplitudes of the decaying and coherence pathways. The ratio $T_1/\tau$ is represented on the vertical axis and the amplitude ratio from equation (19) is represented on the vertical axis. Line 150 represents theoretical results from equation (19). The measured echo shapes from the above-described example were also decomposed into a weighted sum of $s_r(t)$ and $s_d(t)$ using equation (16). The corresponding amplitudes, found using equations (17) and (18). In FIG. 21, the series of data points 152 represent results from the above-described example using a modified inversion recovery CPMG sequence according to an embodiment of the invention. It can be seen that the ratio of the amplitudes $a_d/(a_d+a_r)$ agrees well with the prediction from equation (19). Thus, the amplitudes of the two components may be accurately described by equation (19). This example shows that it may be possible to extract $T_1$ from the echo shape in a single-scan measurement. For good sensitivity, FIG. 21 suggests that the recovery time, τ, may be chosen to be in the range of approximately 0.4 $T_1$ to 10 $T_1$. It is to be appreciated that is if $T_1$ is characterized by a distribution $f(T_1)$, (as may be the case with complex samples, such as water or oil saturated rock) then equation (19) may be replaced by:

$$\frac{a_d}{a_d + a_r} = \frac{\int dT_1 f(T_1) \exp\{-\tau/T_1\}}{\int dT_1 f(T_1)} \quad (25)$$

Various pulse sequences and analysis techniques according to aspects and embodiments of the invention may be used in many applications where fast $T_1$ measurements may be desirable. For example, such applications may include identifying the presence of light condensate and fluids with high GOR, and performing measurements in "super-k" zones in carbonate reservoirs. In some carbonate reservoirs, thin high-permeability zones may completely dominate the flow properties of a formation. Such zones may be characterized by large pores where $T_1$ approaches the bulk relaxation time. It has been difficult to identify these zones reliably with conventional $T_2$-based NMR logging approaches because of diffusion and motion effects. However, as described above, $T_1$ may be far less affected by such diffusion or motion effects, and thus fast, accurate measurements of $T_1$ according to embodiments of the invention may be useful in identifying and quantifying these zones. For example, if the formation is characterized by a bi-modal $T_1$ distribution with widely separated contributions $f_{short}(T_1)$ and $f_{long}(T_1)$, as is the case in some gas zones or super-k zones, it may be preferable to place the recovery time, τ, in the gap between the two contributions. In this case, the amplitudes $a_d$ and $a_r$ may correspond to the porosities associated with the short and long $T_1$ values, respectively. This may apply even if the $T_2$ distributions of the two contributions are overlapping.

In another example, the pulse sequences and analysis techniques of embodiments of the invention may be used for a single-shot $T_1$, $T_2$ and porosity measurement. For narrow relaxation time distributions, the modified inversion recovery CPMG sequence described above may be used to obtain all three quantities in a single measurement. That is, $T_1$ may be obtained from the echo shape, as described above, $T_2$ may be obtained from the decay of the echo amplitudes as known in the art, and the porosity may be obtained from the initial amplitudes. In this example, it may preferable to have the recovery time, τ, chosen between 0.4 and 10 of the expected $T_1$ value. In another example, the average relaxation rate, $1/T_1$, may be obtained in a formation with long relaxation times by performing measurements with multiple recovery times. As discussed above, the average $T_1$ relaxation rate may be obtained from the amplitudes of the decaying signal, $a_d(\tau)$, for measurements with recovery time much less than $T_1$.

Figure 22:
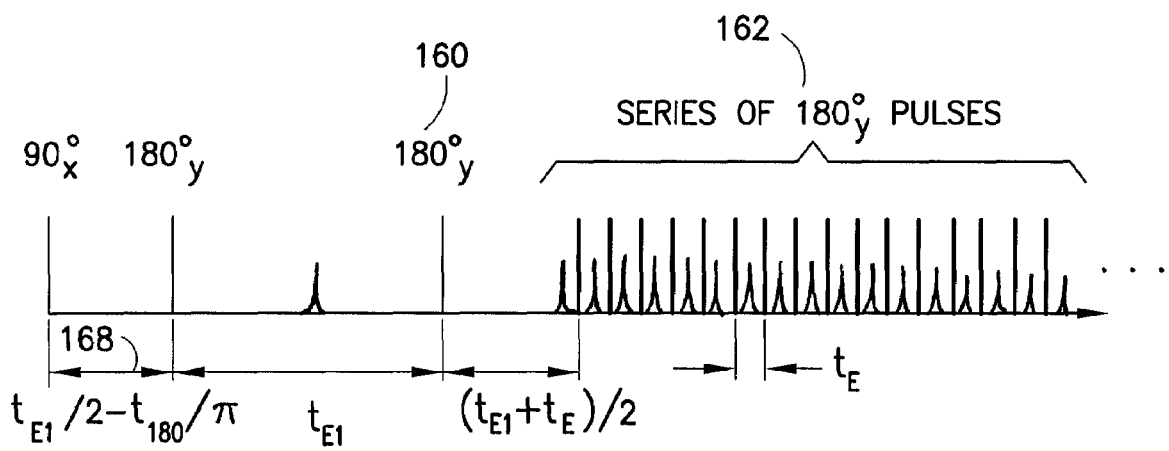
FIG. 22 is a timing diagram of one example of a diffusion editing pulse sequence.

According to another embodiment, the above-described techniques of encoding NMR information in the echo shape may also be applied to diffusion measurements. For example, if more than two pulses are applied in grossly inhomogeneous fields, multiple echoes may form that have different sensitivities to diffusion in the static background gradient. In one embodiment, it may be preferable that at least some echoes form at nearly identical times so that CPMG detection may be used. An example of a standard diffusion editing pulse sequence is illustrated in FIG. 22. In the illustrated example, the pulse sequence comprises a CPMG sequence wherein the first two echo spacings have been increased to encode diffusion information. This type of sequence may allow the echo signal to be formed by contributions from direct and stimulated echo coherence pathways. More specifically, after the second 180° pulse 160 the direct echo and stimulated echo coherence pathways may generate an echo at the same time that may then be refocused by the subsequent long series of 180° pulses 162. This refocusing may be used to increase the signal-to-noise ratio for the echo shape measurement, as discussed above. In one example, the signal may be maximized if the first pulse spacing 166 is reduced from $t_E/2$ to $t_E/2 - t_{180}/\pi$, as indicated in FIG. 22.

In one example, if the $s_{de}(t)$ and $s_{se}(t)$ are the echo shapes of the direct and stimulated echo coherence pathways, respectively, during the CPMG detection (in the absence of diffusion) then the measured echo shape may be given by:

$$S(t) \propto s_{de}(t) \exp\left\{-\frac{1}{6} \gamma^2 g^2 t_{E1}^3 D\right\} + s_{se}(t) \exp\left\{-\frac{1}{3} \gamma^2 g^2 t_{E1}^3 D\right\} \quad (26)$$

where:

g is the magnetic field gradient;

D is the diffusion coefficient; and $t_{E1}$ is the echo spacing of the first two echoes.

Figure 24B:
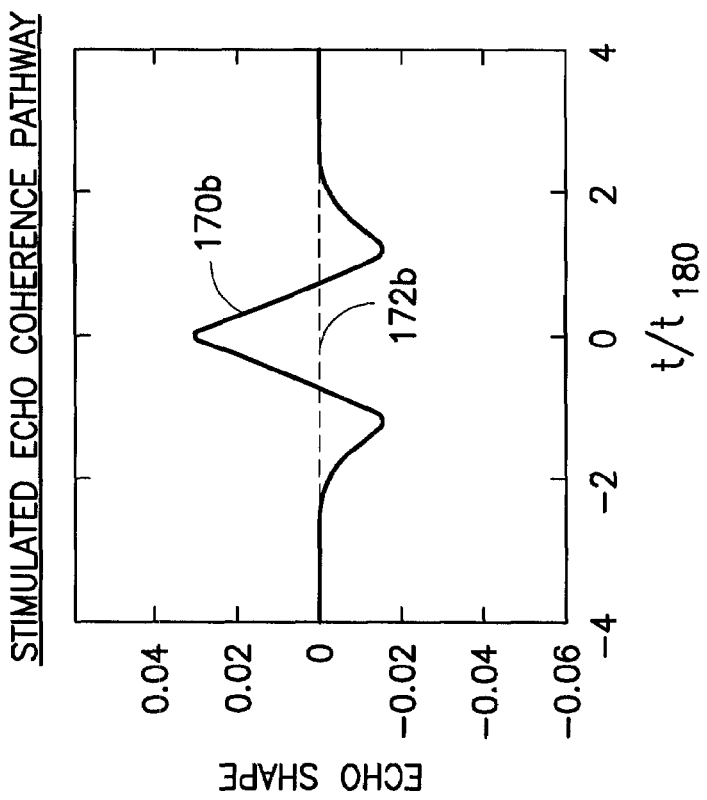
FIG. 24B is a plot of a calculated echo shape for the stimulated echo coherence pathway using the pulse sequence of FIG. 22.
Figure 24A:
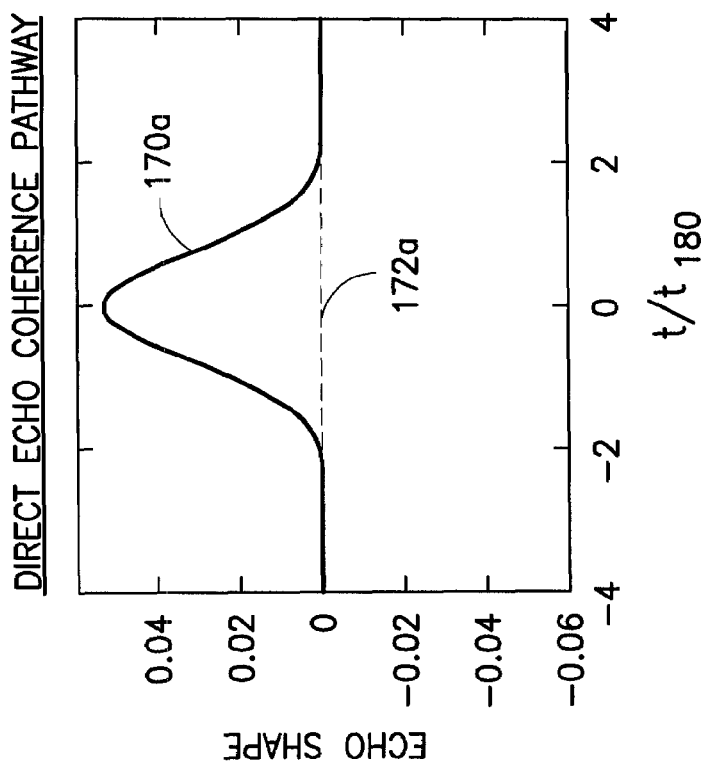
FIG. 24A is a plot of a calculated echo shape for the direct echo coherence pathway using the pulse sequence of FIG. 22.

The weights may depend on the diffusion and relaxation parameters of the sample, but the echo shapes the $s_{de}(t)$ and $s_{se}(t)$ may depend only on the RF pulses. Referring to FIGS. 24A and 24B, there are illustrated the calculated echo shapes $S_{de}(t)$ and $s_{se}(t)$ for the direct echo and stimulated echo contributions, respectively, that correspond to the pulse sequence of FIG. 22. The in-phase signal is shown as the solid lines 170a (direct echo. FIG. 24A) and 170b (stimulated echo. FIG. 24B), and the out-of-phase signals are shown as the dashed lines 172a (direct echo, FIG. 24A) and 172b (stimulated echo, FIG. 24B). For these calculations, it was assumed that the nominal flip angle, θ, was 98° (θ is proportional to the duration and strength of the RF pulse). It can be seen that for the pulse sequence illustrated in FIG. 22, referred to herein as Sequence A, the two contributions strongly overlap.

In one embodiment, if the two contributions can be separated, the relative amplitudes may be used to infer the diffusion coefficient from a measurement with a single encoding time. However, with the standard diffusion editing sequence, illustrated in FIG. 22, it may be difficult to separate the two components, $s_{de}(t)$ and $s_{se}(t)$ from each other. This may be due to the considerable overlap between the two components, as can be seen in FIGS. 24A and 24B. Therefore, according to aspects of the invention, there are provided some examples of modified pulse sequences that may allow a robust separation of the two contributions.

Figure 23:
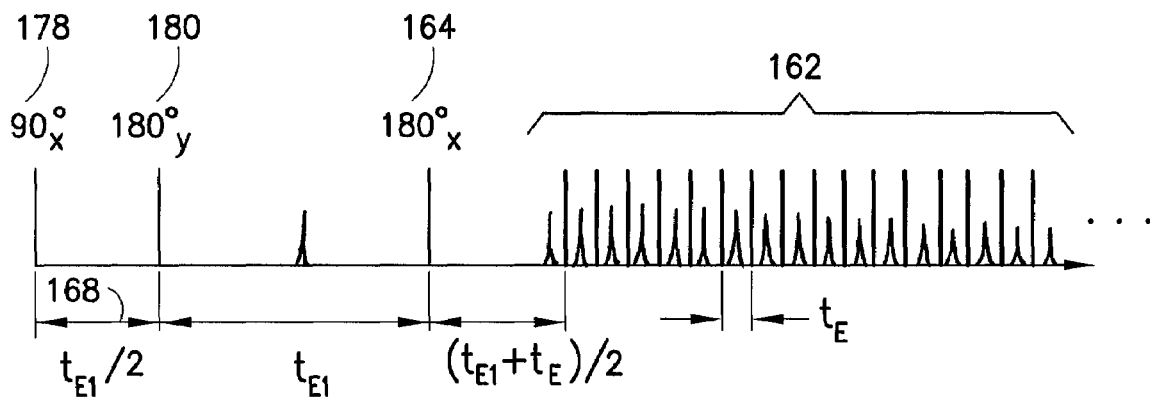
FIG. 23 is a timing diagram of another example of pulse sequence that may be used for diffusion encoding by phase separation, according to an embodiment of the invention.
Figure 25B:
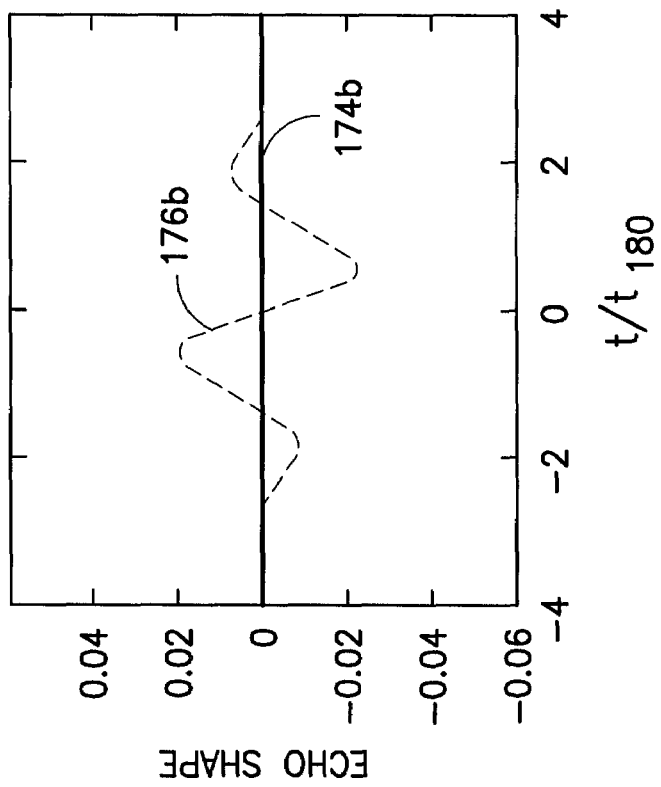
FIG. 25B is a plot of a calculated echo shape for the stimulated echo coherence pathway using the pulse sequence of FIG. 23.
Figure 25A:
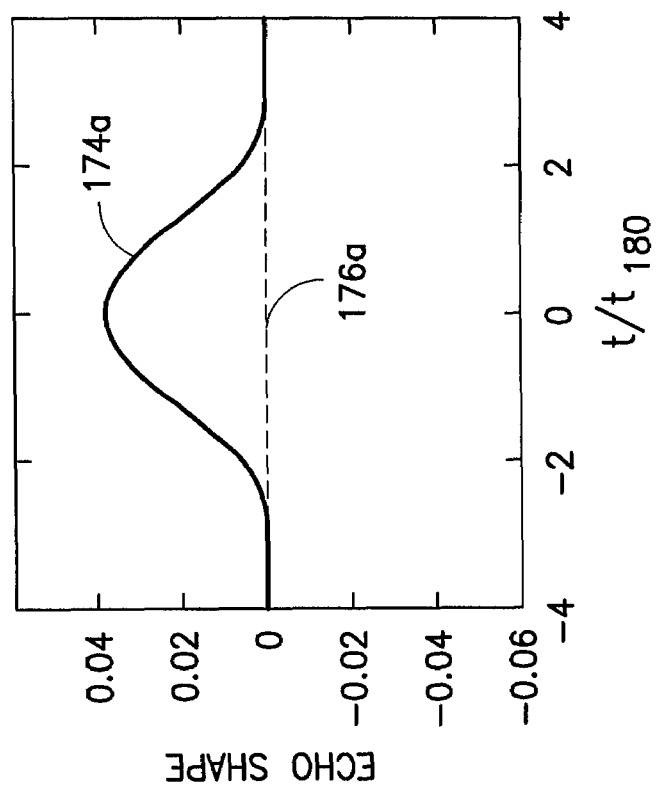
FIG. 25A is a plot of a calculated echo shape for the direct echo coherence pathway using the pulse sequence of FIG. 23.

According to one embodiment, a pulse sequence may be used that has the form illustrated in FIG. 23. In this embodiment, the phase of either the first or second 180° pulse may be changed by 90°. Referring to FIG. 23, in the illustrated example, the phase of the second 180° pulse 164 has been shifted from y to x. As a result, the signal of the two contributions may form out of phase to each other, analogous to the methods described above in reference to the $T_1$ measurements. Referring to FIGS. 25A and 25B, there are illustrated calculated echo shapes for the direct echo signal (FIG. 25A) and the stimulated echo signal (FIG. 25B). In FIG. 25A, the solid line 174a represents the in-phase signal and the dotted line 176a represents the out-of-phase signal. Similarly, in FIG. 25B, the in-phase signal is shown as solid line 174b and the out-of-phase signal is shown as dotted line 176b. Again, it was assumed that θ=98°. It can be seen that with Sequence B, the contribution from the stimulated echo (FIG. 25B) form out of phase with respect to the contribution from the direct echo (FIG. 25A). Thus, Sequence B may facilitate diffusion encoding by phase separation of the signals from the two coherence pathways. In addition, the timing of the first two pulses may be slightly adjusted compared to Sequence A. In sequence B (the sequence illustrated in FIG. 23), if the pulse spacing is left identical to that of Sequence A, the contribution of the direct echo may be maximized, while the contribution of the stimulated echo may be minimized. Therefore, in one example, the timing of Sequence B may be adjusted such that the first pulse spacing 168 may be $t_E/2$, as shown. This may greatly increase the stimulated echo contribution and only modestly decrease the direct echo signal.

Figure 26B:
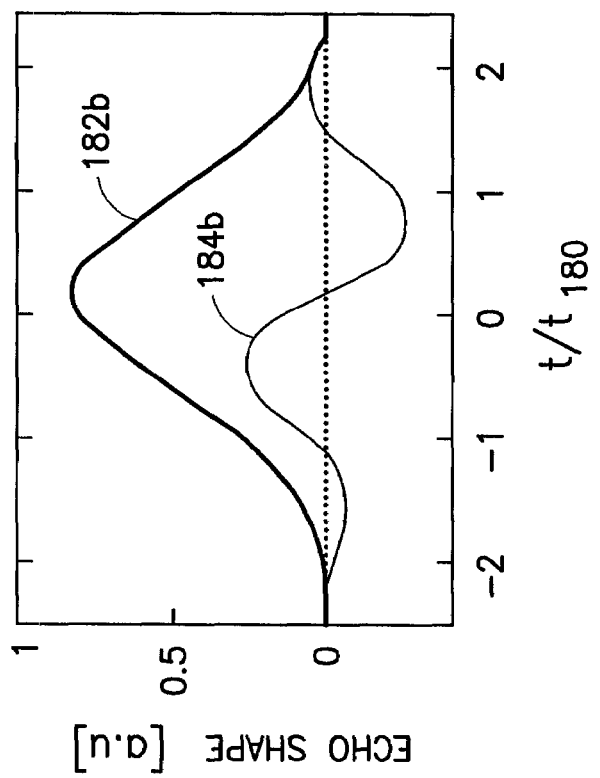
FIGS. 26A-E are plots of example echo shapes for the pulse sequence of FIG. 23 for a series of diffusion coefficient values.
Figure 26A:
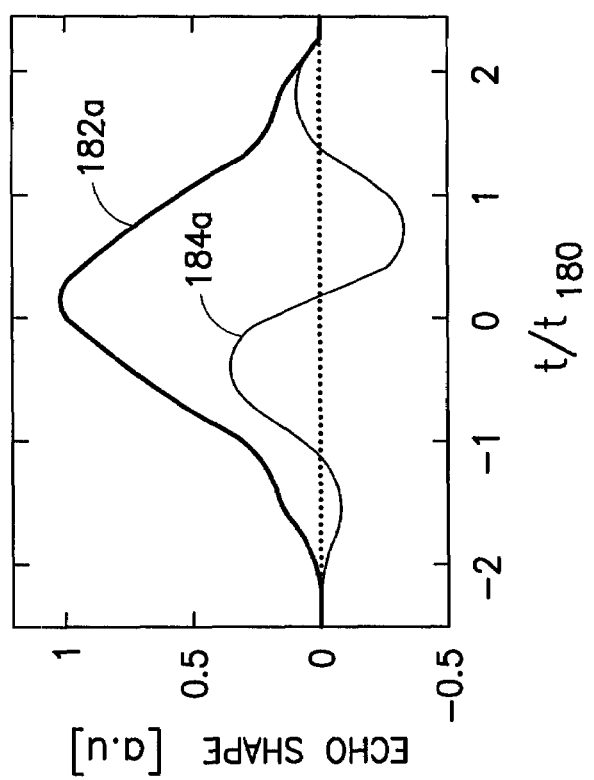
Figure 26D:
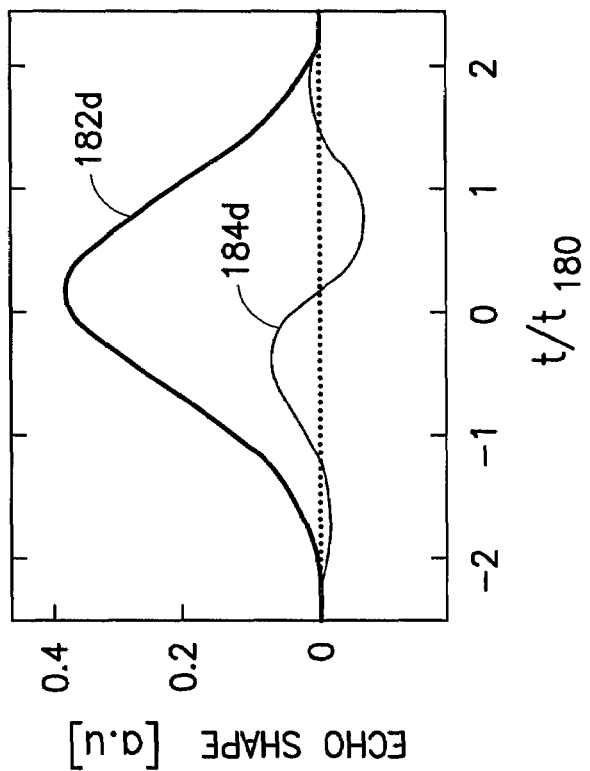
Figure 26C:
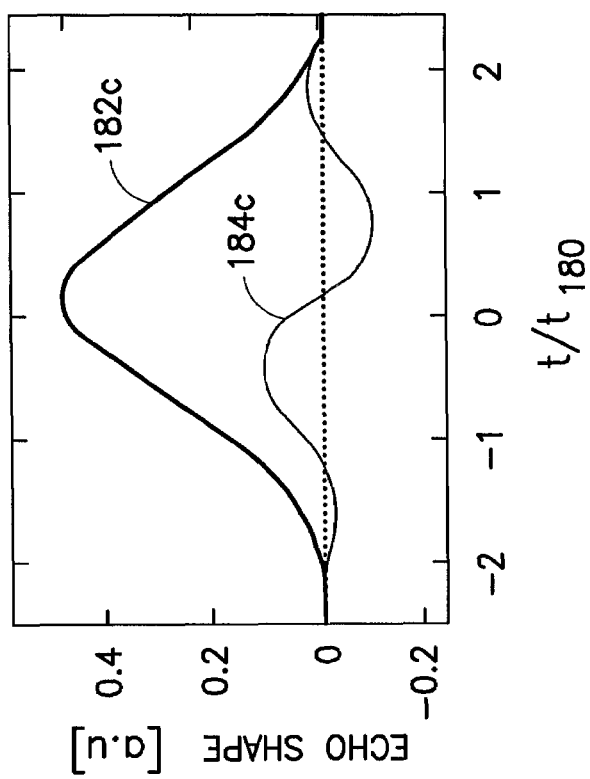
Figure 26E:
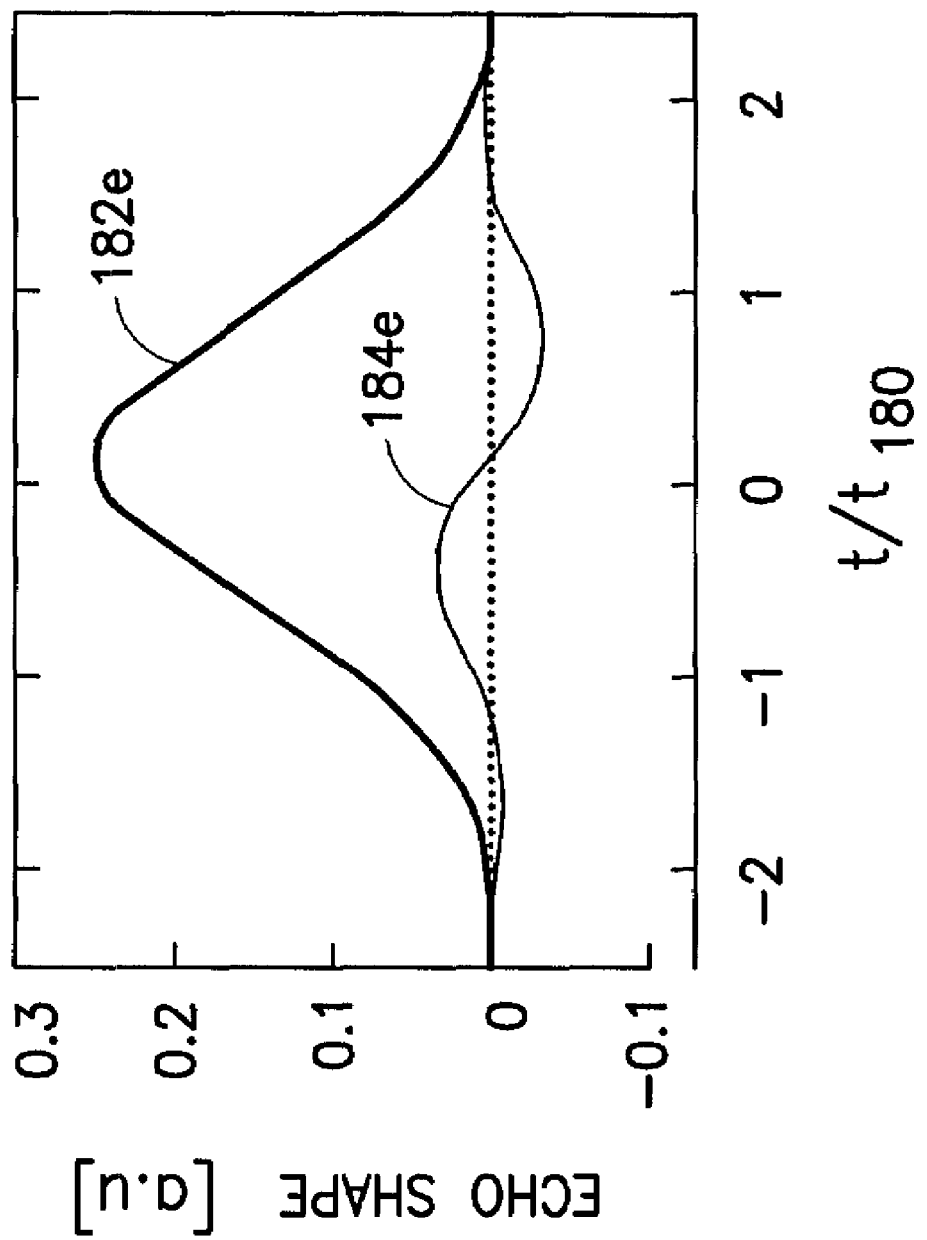

An example was performed to test Sequence B on a sample of doped water. In this example, the initial echo spacing, $t_{E1}$, was systematically increased in 32 steps to a maximum value of 17.1 ms. For each case, the CPMG detection comprises 2000 echoes that were acquired with an echo spacing of $t_{E1}$=424 μs. The durations of the nominal 90° pulse 178 and 180° pulses 180 and 164 were $t_{90}$=24 μs and were $t_{180}$=48 μs. Referring to FIGS. 26A-26E, there are illustrate the in-phase and out-of-phase components of measured echo shapes, S(t), for phase encoding of diffusion information using Sequence B. A series of five examples were performed with different values of the factor $\gamma^2 g^2 t^3_{E1} D$. FIGS. 26A-E illustrate the echo shapes during CPMG detection for each of these five different values. The echo shapes were extracted from the acquired data by averaging the shapes of the 100$^{th}$ to 300$^{th}$ echo. FIG. 26A shows the extracted echo shape for $\gamma^2 g^2 t^3_{E1} D$=0.01. Line 182a represents the in-phase signal and line 184a represents the out-of-phase signal. In FIG. 26B, the extracted echo shape for $\gamma^2 g^2 t^3_{E1} D$=0.4 is presented, with the in-phase signal shown as line 182b and the out-of-phase signal shown as line 184b. Similarly, in FIG. 26C, the echo shape for $\gamma^2 g^2 t^3_{E1} D$=3.1 is presented, with the in-phase signal shown as line 182c and the out-of-phase signal shown as line 184c. FIG. 26D illustrates the echo shape for $\gamma^2 g^2 t^3_{E1} D$=4.4. Line 182d represents the in-phase signal and line 184d represents the out-of-phase signal. Lastly, FIG. 26E illustrates the echo shape for $\gamma^2 g^2 t^3_{E1} D$=6.5, with line 182e representing the in-phase signal and line 184e representing the out-of-phase signal. It can be seen that, in agreement with the theoretical expectation illustrated in FIGS. 25A and 25B, there are both sizable in-phase and out-of-phase signals. The in-phase signals (lines 182a-e) are symmetric and are generated by the direct echo coherence pathways, while the out-of-phase signals (lines 184a-e) are anti-symmetric and are generated by the stimulated echo coherence pathways. As the initial echo spacing is increased, diffusion may become more important, and may preferentially reduce the out-of-phase component.

Figure 27A:
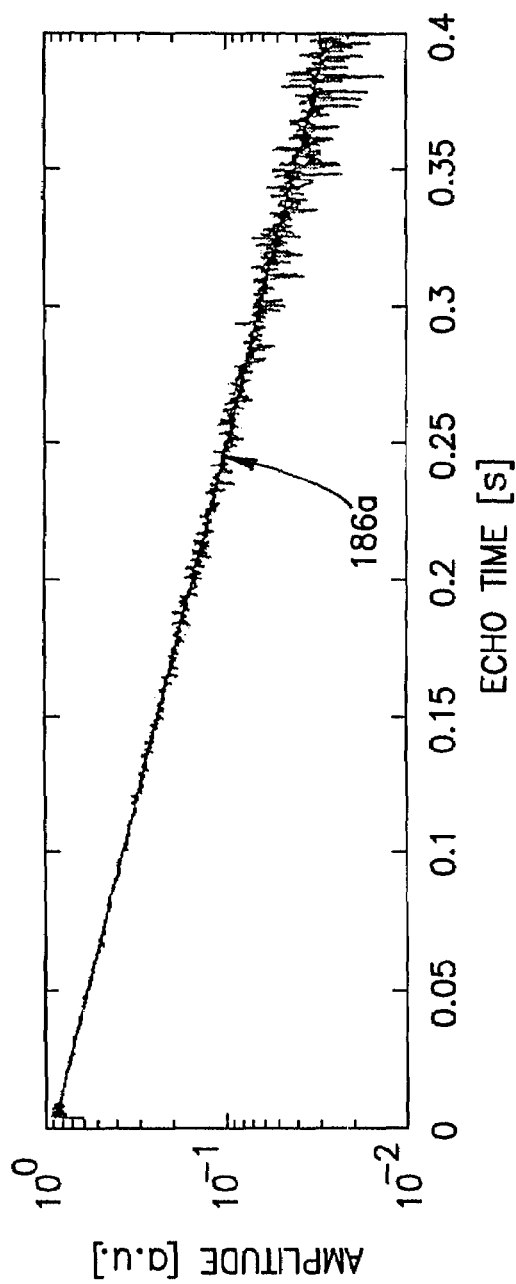
Figure 27B:
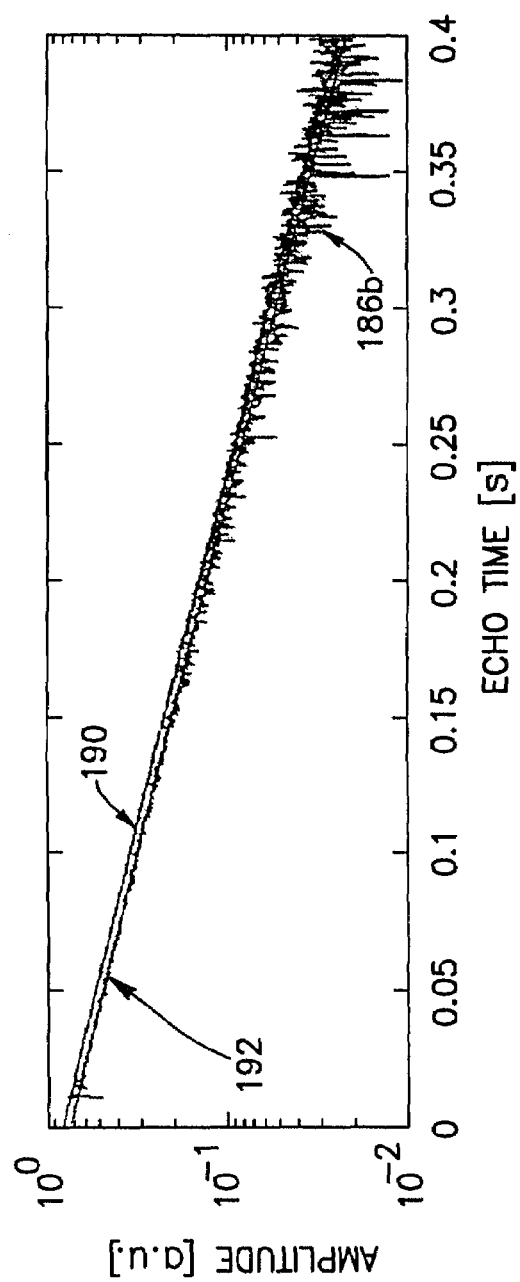
Figure 27E:
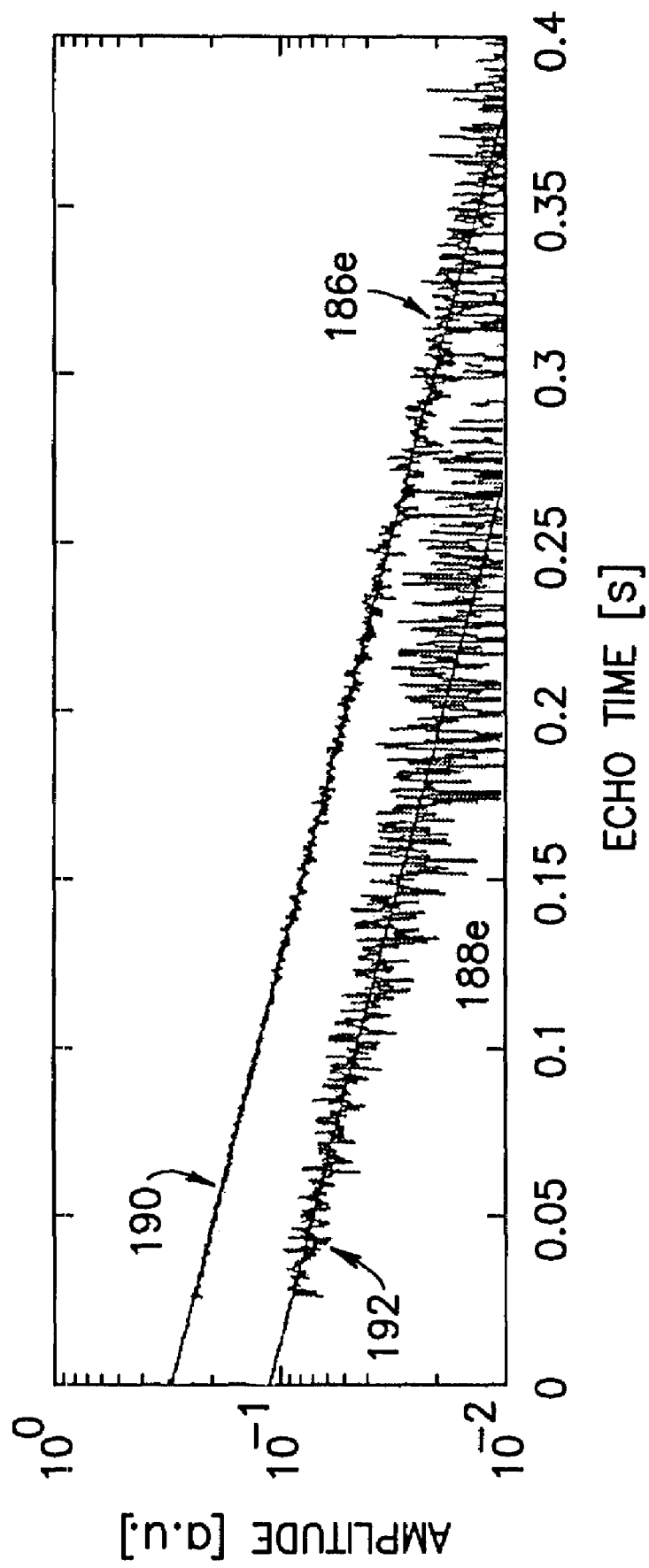

In one example, for each echo, the amplitudes of the two components may be extracted using as matched filters the expected echo shapes in the absence of diffusion. Extracted amplitudes, corresponding to the echo shapes shown in FIGS. 26A-E, are illustrated in FIGS. 27A-E versus time after the initial 90° pulse 178. Within the CPMG train, the echo shapes remain unchanged, as discussed above, and the amplitudes of all components may decay with substantially the same relaxation time. In FIGS. 27A-27E, amplitudes of the in-phase components are shown as series 186a-e, respectively, and the amplitudes of the out-of-phase signals are shown as series 188a-e, respectively. In FIGS. 27A and 27B, the two series are very close to one another and cannot be easily distinguished. However, the separation increases in FIGS. 27C-E. In each case, the solid lines 190 and 192 are an exponential fit to single exponential decays for the in-phase and out-of-phase components, respectively. Substantially identical transverse relaxation times, $T_{2,eff}$=114 ms, may be found for all measurements.

Figure 28:
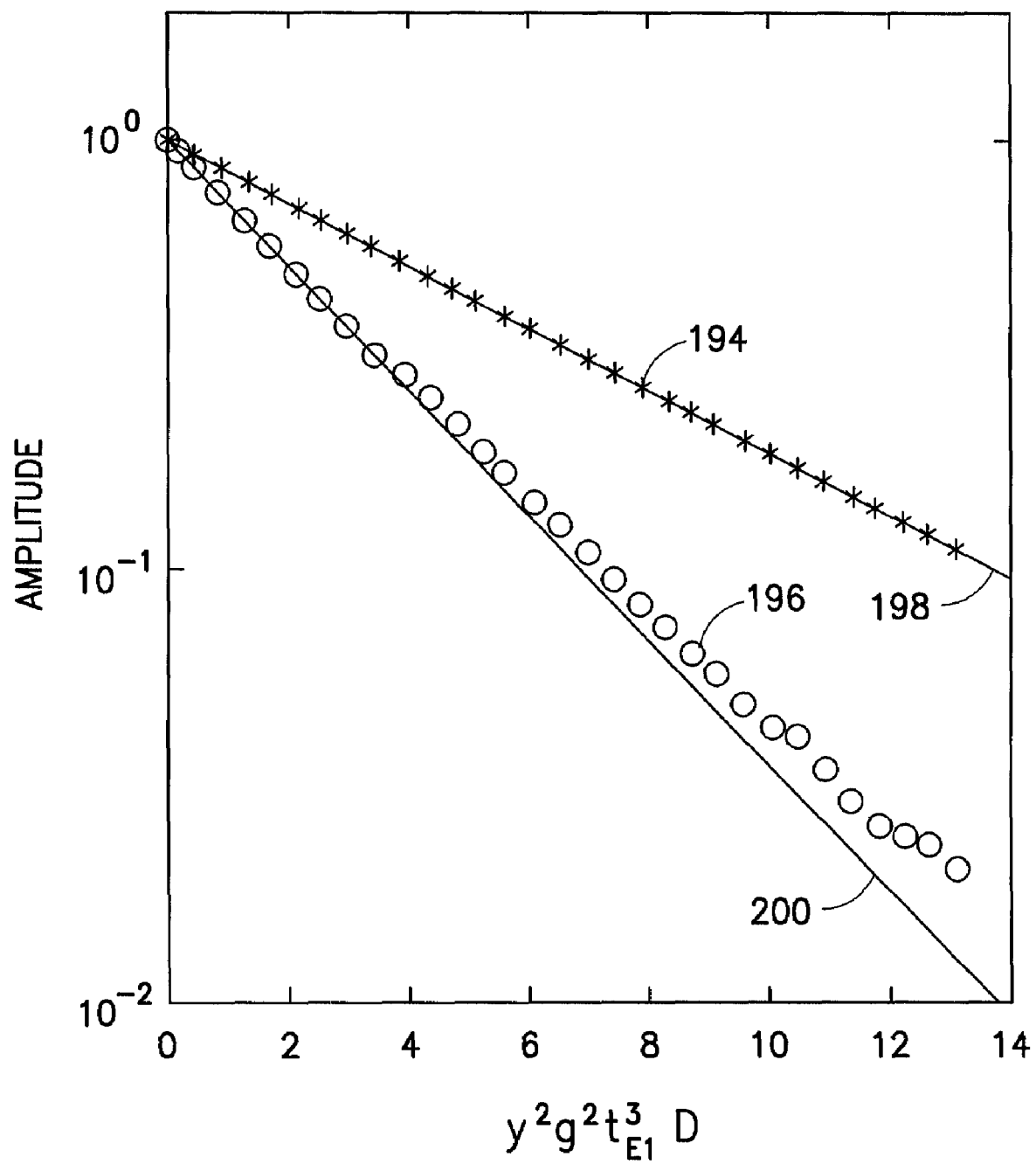
FIG. 28 is a plot of fitted amplitudes of the in-phase and out-of-phase echo signals versus the diffusion coefficient for the pulse sequence of FIG. 23.

Referring to FIG. 28, there is illustrated a plot of the fitted initial amplitudes, extrapolated to zero time, for the in-phase and out-of-phase components versus the dimensionless diffusion coefficient, $\gamma^2 g^2 t^3_{E1} D$. The initial amplitudes of the in-phase contribution are shown as series 194 and the initial amplitudes of the out-of-phase contribution are shown as series 196. The solid line 198 shows the expected dependence for the direct echo coherence pathway and the solid line 200 shows the expected dependence for the stimulated echo coherence pathway. It can be seen from FIG. 28 that the amplitudes of both the in-phase and out-of-phase components may decay exponentially as a function of the dimensionless diffusion coefficient, $\gamma^2 g^2 t^3_{E1} D$, but with exponents that differ by a factor of 2. This confirms that the in-phase and out-of-phase components are associated with the direct echo or stimulated echo coherence pathways, respectively. In addition, there is excellent agreement between the example results and the theoretical prediction of equation (26) (represented by lines 198 and 200). It should be noted that the amplitudes of the first few echoes show a characteristic transient effect, similar to that observed with a standard CPMG sequence. This is well understood in the art and is caused by imperfect averaging of the magnetization perpendicular to the net axis, n̂. As discussed above, these effects may affect only the first few echoes and therefore, for the later echoes, the asymptotic expression in equation (2) may be an excellent approximation. Also, for the higher values of the diffusion coefficient, $\gamma^2 g^2 t^3_{E1} D$, it can be seen that the measured amplitudes 196 of the out-of-phase component are somewhat above the theoretical prediction of line 200. This may be due to a small mixing of the direct echo coherence pathway into the out-of-phase signal. This mixing may be caused by asymmetries of the sample shape along the field gradient, asymmetry in the frequency response of the NMR detection system, or imperfect tuning.

Figure 29:
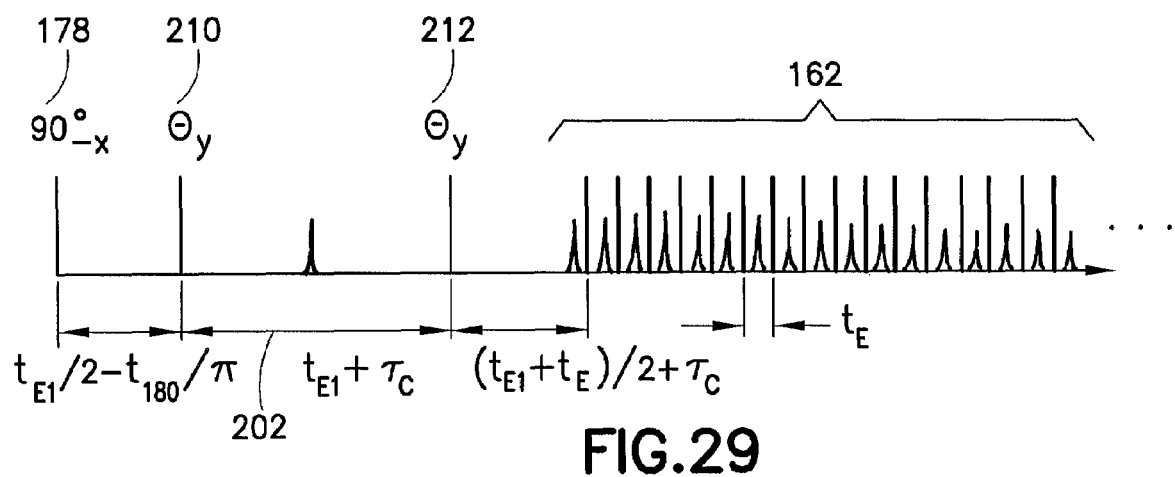
FIG. 29 is a timing diagram of a pulse sequence for diffusion encoding by time separation according to an embodiment of the invention.
Figure 30B:
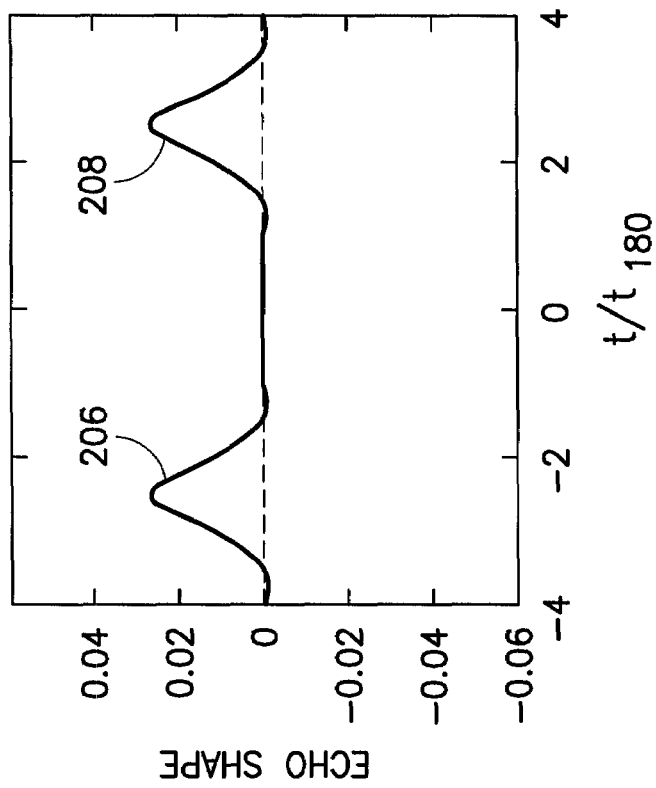
FIG. 30B is a plot of a calculated echo shape for the stimulated echo coherence pathway using the pulse sequence of FIG. 29.
Figure 30A:
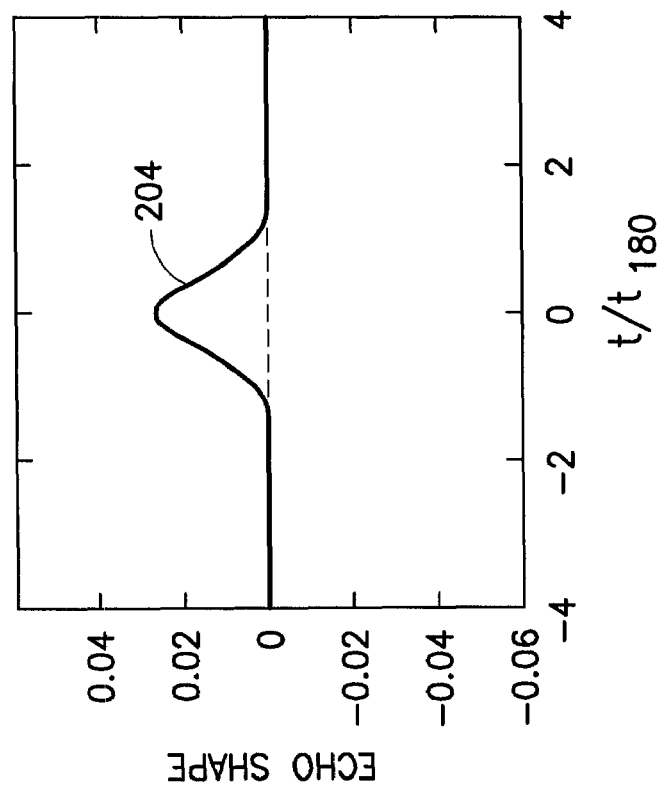
FIG. 30A is a plot of a calculated echo shape for the direct echo coherence pathway using the pulse sequence of FIG. 29.

According to another embodiment, a pulse sequence may be used to implement diffusion encoding by separating the contributions of the two coherence pathways temporally. One example of such a pulse sequence, referred to herein as Sequence C, is illustrated in FIG. 29. In one example, the two contributions (the direct echo and stimulated echo coherence pathways) may be separated directly in the time domain by increasing the second echo spacing 202 by a small amount, $\tau_c$. The stimulated echo may then form a duration, $\tau_c$, earlier than the direct echo. The echoes in the CPMG detection may then comprise a central peak 204 (illustrated in FIG. 30A) due to the direct echo and two symmetric side peaks 206 and 208 (see FIG. 30B) due to the stimulated echo. The two side peaks may be shifted by $\pm(\tau_c - 2t_{180}/\pi)$. The value of $\tau_c$ may be large enough to separate the two contributions (i.e., larger than $t_{180}$), but small enough so that the shifted peaks still lie within the detection window (i.e., less than $t_E/2$). In this calculation, the extra time delay, $\tau_c$, was 2.5 $t_{180}$. The nominal flip angle, $\theta$, may control the relative weights of the two coherence pathways, and was assumed, for this calculation, to be 98°.

An example was performed to test diffusion encoding by separating the contributions of the two coherence pathways in time using Sequence C. In this example, the durations of the nominal 90° pulse 178 and 180° pulses 210 and 212 were $t_{90}=12$ μs and were $t_{180}=24$ μs. The duration of the second and third pulses 210, 212 was set to 14 μs, corresponding to a nutation angle, $\theta=105°$ on resonance. The delay, $\tau_c$, was set to 60 μs=2.5 $t_{180}$. Data was acquired for 32 different initial echo spacing, $t_{E1}$, up to a maximum of 17.1 ms. The CPMG detection comprises 2000 echoes, acquired with an echo spacing of $t_E=400$ μs.

Figure 31A:
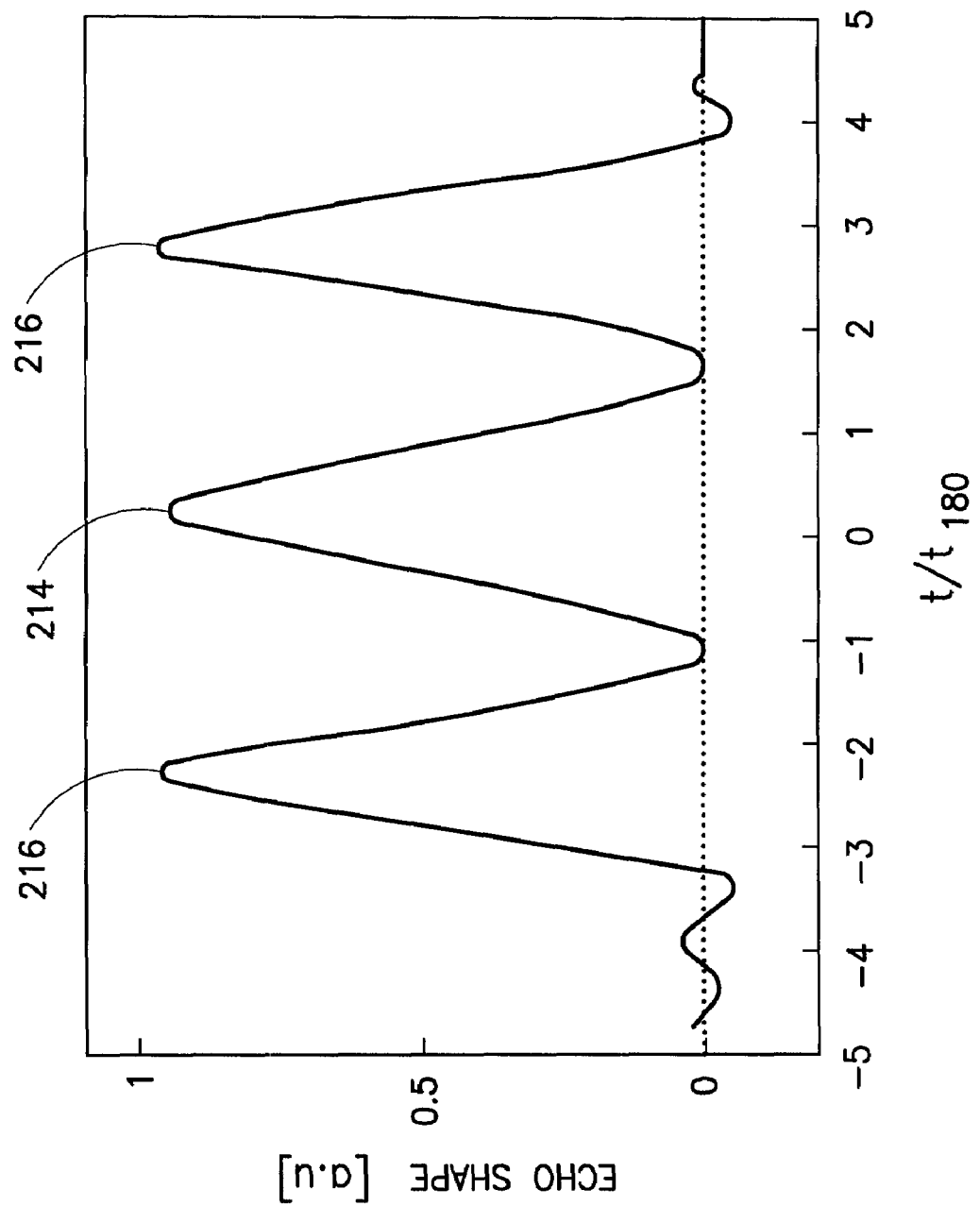
FIGS. 31A-E are plots of example echo shapes for the pulse sequence of FIG. 29 for a series of diffusion coefficient values.
Figure 31B:
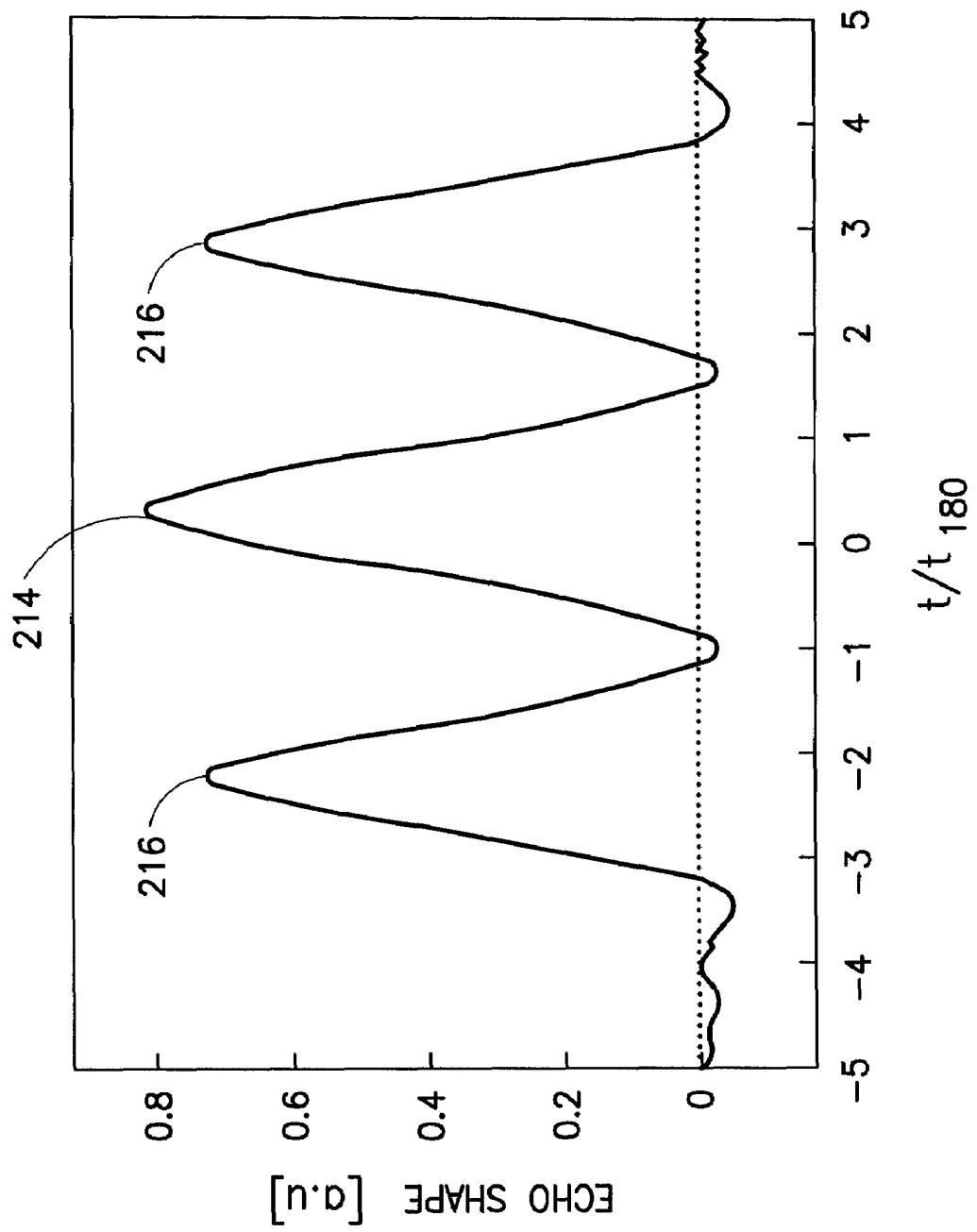
Figure 31C:
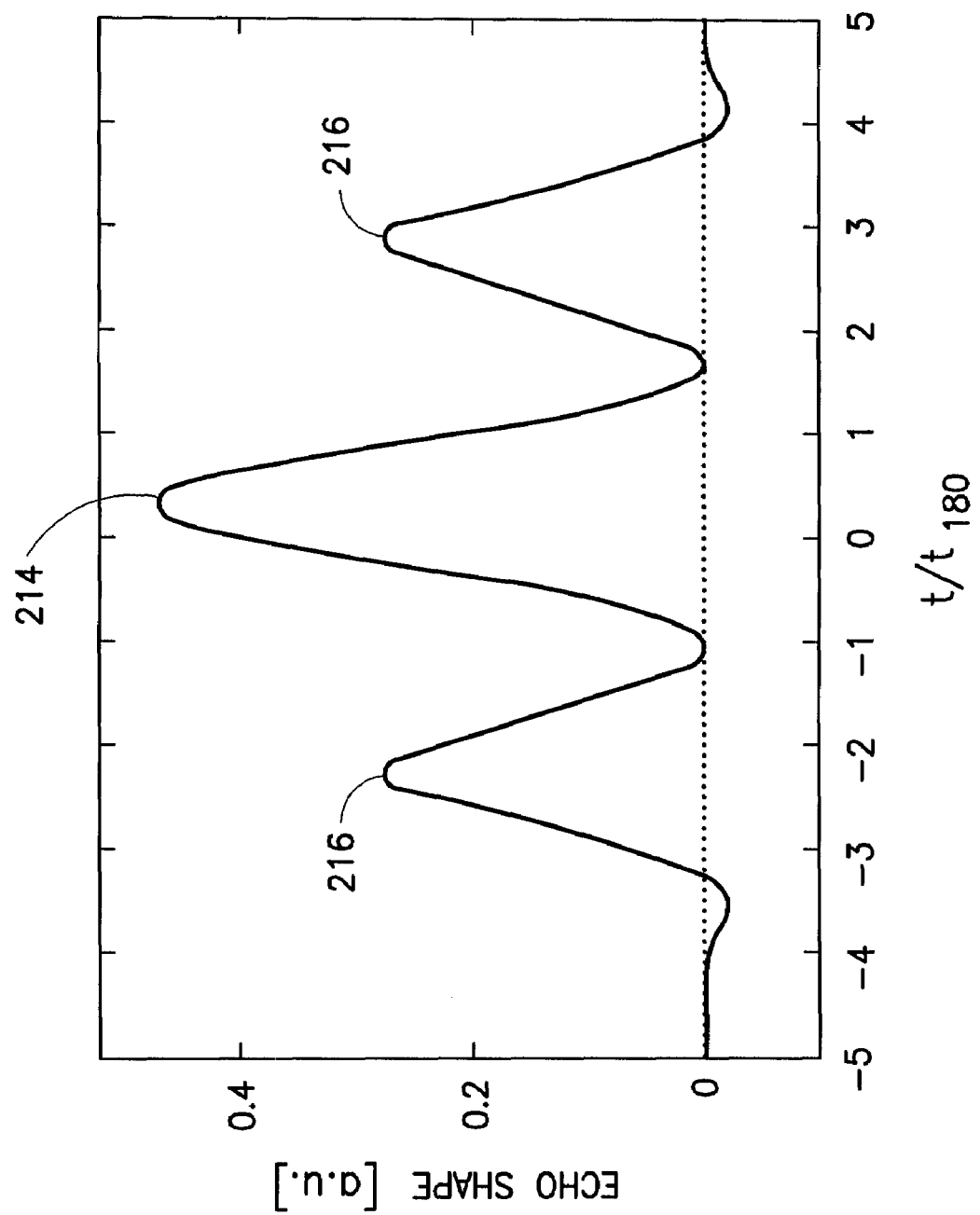
Figure 31D:
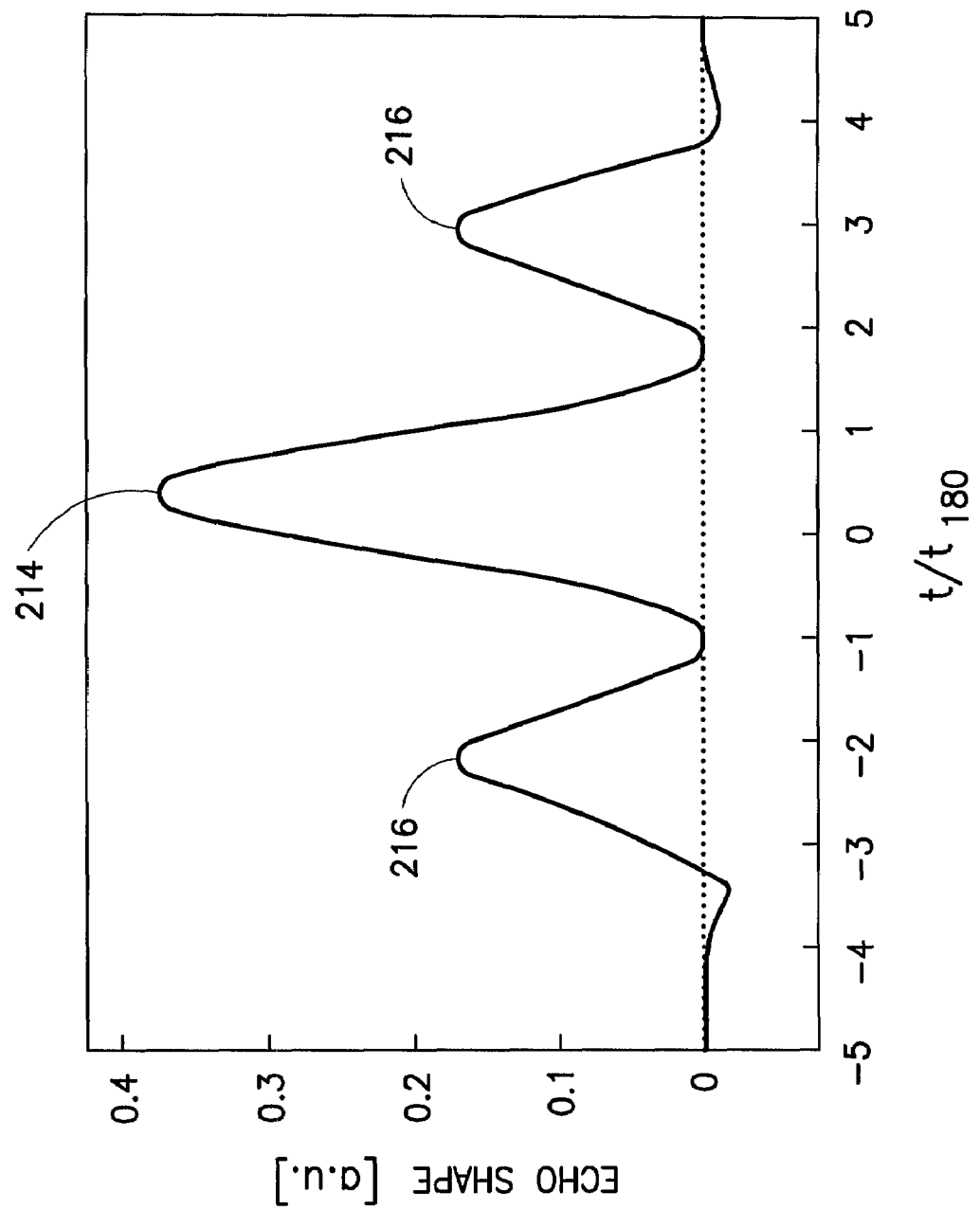
Figure 31E:
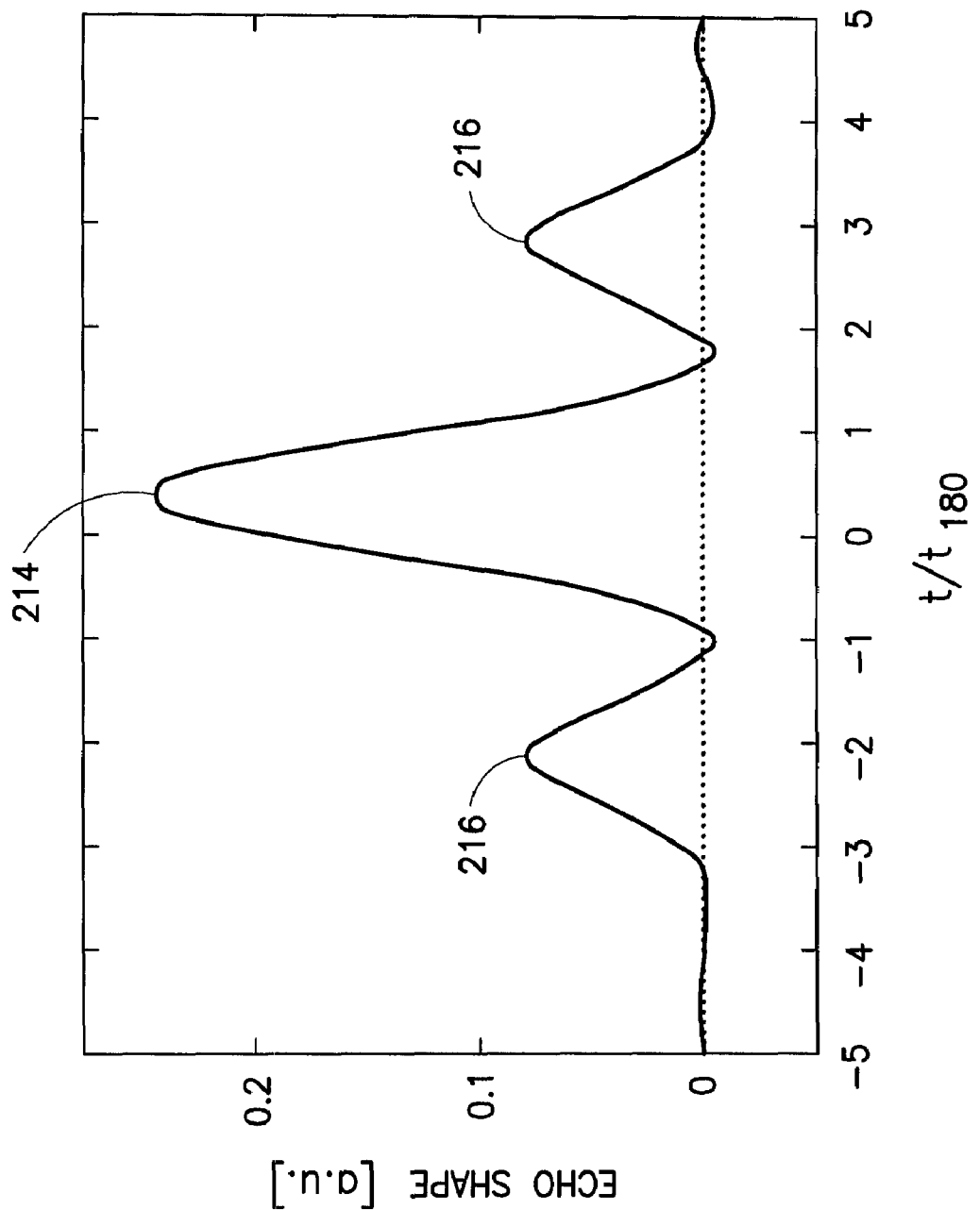

Referring to FIGS. 31A-E, there are illustrated results from this example. Again, five examples with different diffusion coefficients (i.e., different initial echo spacing) were performed. In each of FIGS. 31A-E, the in phase components of the echo shape, S(t), are illustrated as a function of time. FIG. 31A shows the echo shape for $\gamma^2 g^2 t^3_{E1} D=0.01$, FIG. 31B shows the echo shape for $\gamma^2 g^2 t^3_{E1} D=0.4$, FIG. 31C shows the echo shape for $\gamma^2 g^2 t^3_{E1} D=3.1$, FIG. 31D shows the echo shape for $\gamma^2 g^2 t^3_{E1} D=4.5$, and FIG. 31E shows the echo shape for $\gamma^2 g^2 t^3_{E1} D=6.7$. As can be seen in the figures, the echoes form in phase with a central peak 214 and two symmetrical satellite peaks 216. When the diffusion constant is small (i.e., diffusion is not an important effect), the amplitudes of the central peak and the two satellite peaks are very similar. As the initial echo spacing is increased, corresponding to a larger value of the diffusion coefficient (and the progression from FIG. 31A to FIG. 31E), the satellite peaks, which are due to stimulated echo coherence pathway, attenuate more than does the central peak which is generated by the direct echo coherence pathway.

Figure 32:
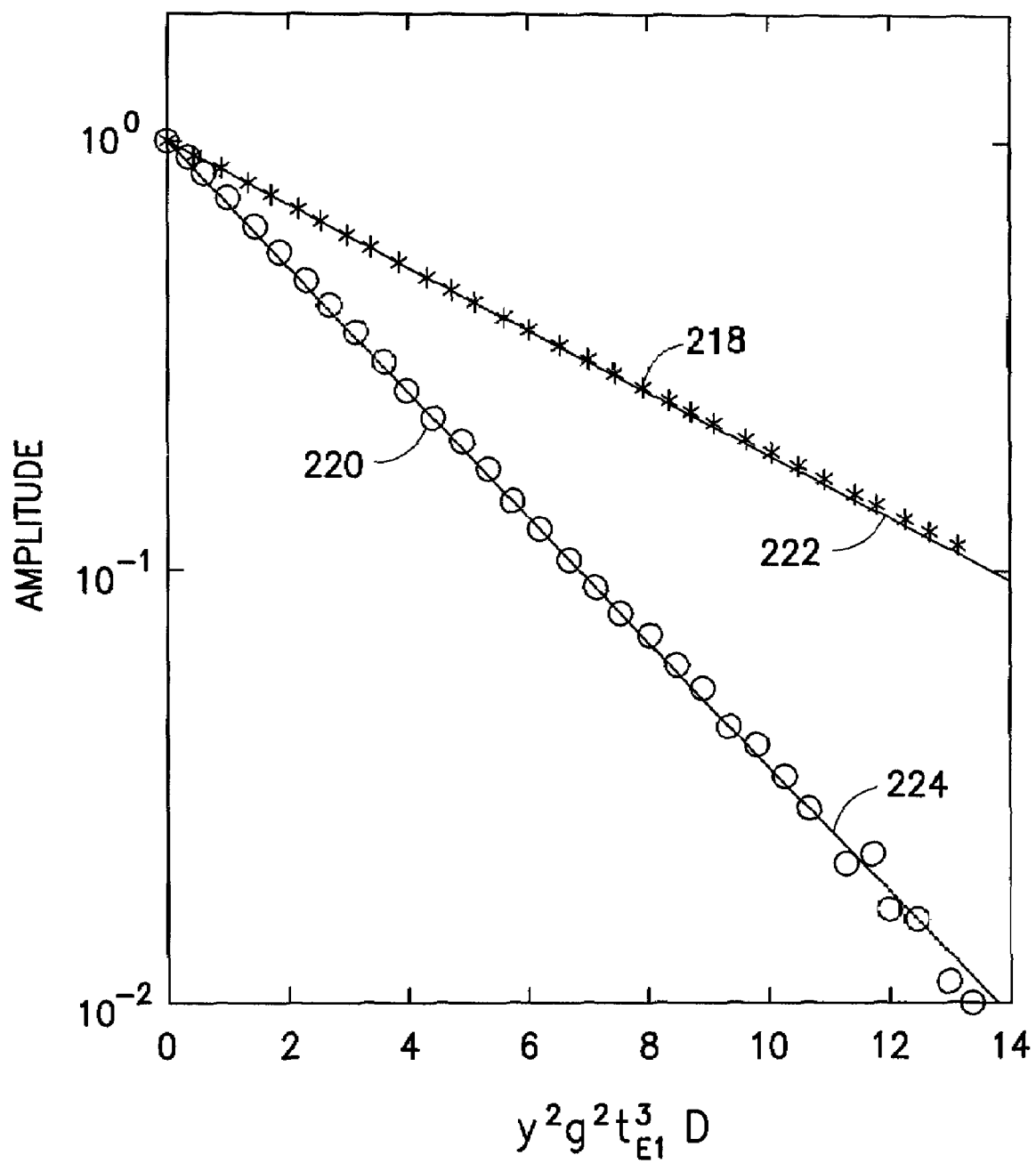
FIG. 32 is a plot of fitted amplitudes of the in-phase and out-of-phase echo signals versus the diffusion coefficient for the pulse sequence of FIG. 29.

As discussed above in reference to Sequence B, the amplitudes of the two components may be extracted using the expected echo shapes for the two pathways as matched filters. From the decay of these amplitudes, the transverse relaxation time, $T_{2,eff}$ may be extracted, as discussed above. For this example, a value of $T_{2,eff}=114$ ms was obtained, the same as for the example using Sequence B. Referring to FIG. 32, there is illustrated a plot of the fitted amplitudes of the two contributions versus the dimensionless diffusion coefficient, $\gamma^2 g^2 t^3_{E1} D$ for diffusion encoding by temporal separation of the two contributions. The fitted initial amplitudes of the central peak are represented by data series 218 and the fitted initial amplitude of the satellite peaks are represented by data series 220. Line 222 is an expected dependence of the direct echo coherence pathway, and line 224 is the expected dependence of the stimulated echo coherence pathway. It can be seen that there is excellent agreement between the example results and the theoretical predictions (lines 222 and 224), even at high values of the diffusion coefficient (corresponding to large diffusion effects).

These examples illustrate that for both implementations of diffusion encoding in the echo shape (i.e., by phase separation or time separation), the value of the diffusion coefficient may be extracted from the measurement with a single value of $t_{E1}$. The results shown in FIGS. 28 and 32 demonstrate that the ratio of the amplitudes of the two components may be directly related to the diffusion coefficient. It is to be appreciated that the principles of the invention are not limited to the example pulse sequences described and illustrated herein, and other pulse sequences may also be used to measure diffusion, relaxation, and other parameters. For example, in samples where $T_1$ is not equal to $T_2$, some relaxation effects may be present during the encoding sequence that may have an effect on the diffusion coefficient measurement. Therefore, in another example, a pulse sequence may be used to compensate for such relaxation effects by choosing two coherence pathways that have identical relaxation, but different diffusion sensitivities.

Aspects of the invention described herein in reference to a single-shot $T_1$ measurement may also be extended to other applications. For example, any of the diffusion sequences described herein (e.g., Sequences A, B or C) may also be used for the detection and quantification of flow or convection. In one example, to the first order, the direct echo coherence pathway may be unaffected by flow, whereas the in-phase amplitude of the stimulated echo coherence pathway may be sensitive to the mean squared displacement of the spins with respect to the applied magnetic fields. When coherent motion dominates, this measurement may provide a single-shot determination of the magnitude of the average flow velocity.

According to various aspects and embodiments of the invention, it may be possible to encode information in grossly inhomogeneous fields not only in the amplitude, but also in the shape of the echoes in a CPMG train. This may allow a variety of measurements, including single-shot measurements of diffusion and $T_1$. Having thus described several aspects and embodiments of the invention, modifications and/or improvements may be apparent to those skilled in the art and are intended to be part of this disclosure. For example, it is to be understood that the invention may not require the use of CPMG detection, and other detection sequences may be used, such as a free induction decay sequence or a spin echo sequence. It is to be appreciated that the invention is not limited to the specific examples described herein and that the principles of the invention may be applied to a wide variety applications. The above description is therefore by way of example only, and includes any modifications and improvements that may be apparent to one of skill in the art. The scope of the invention should be determined from proper construction of the appended claims and their equivalents.

The invention claimed is:

1. A method of measuring diffusion in a sample in a Nuclear Magnetic Resonance (NMR) system, the method comprising:

using the NMR system for applying a sequence of RF pulses to the sample, the sequence including an encoding portion and a detection portion;

acquiring an echo signal using the detection portion of the sequence of RF pulses;

decomposing the echo signal into at least two coherence pathway components; and distinguishing between each coherence pathway component from the at least two coherence pathway components so as to analyze the at least two coherence pathway components to determine a diffusion coefficient; and storing the determined diffusion coefficient.

2. The method as claimed in claim 1, wherein decomposing the echo signal into at least two coherence pathway components includes decomposing the echo signal into a direct echo component and a stimulated echo component.

3. The method as claimed in claim 2, wherein analyzing the at least two coherence pathway components includes:

extracting a first amplitude of the direct echo component;

extracting a second amplitude of the stimulated echo component; and determining the diffusion coefficient from a ratio of the first and second amplitudes.

4. The method as claimed in claim 2, wherein the detection portion of the sequence of RF pulses comprises a Carr-Purcell-Meiboom-Gill (CPMG) pulse train.

5. The method as claimed in claim 2, wherein the encoding portion of the sequence of RF pulses comprises a pair of 180° pulses having phases that differ by 90°.

6. A nuclear magnetic resonance (NMR) measurement device comprising:

a transmitter constructed and arranged to generate a sequence of RF pulses and to apply the sequence of RF pulses to a sample;

a receiver constructed and arranged to receive an NMR echo signal from the sample; and a processor constructed and arranged to decompose the NMR echo signal into at least two coherence pathway components, distinguishing between each coherence pathway component from the at least two coherence pathway components so as to analyze at least one of the two coherence pathway components to determine a parameter of the sample.

7. The nuclear magnetic resonance measurement device as claimed in claim 6, wherein the sequence of RF pulses comprises an encoding portion and a detection portion.

8. The nuclear magnetic resonance measurement device as claimed in claim 7, wherein the detection portion comprises a Carr-Purcell-Meiboom-Gill (CPMG) pulse train.

9. The nuclear magnetic resonance measurement device as claimed in claim 8, wherein the encoding portion of the sequence of RF pulses comprises a pair of 127° pulses separated from one another by a first time period.

10. The nuclear magnetic resonance measurement device as claimed in claim 8, wherein the encoding portion of the sequence of RF pulses comprises a pair of 180° pulses having phases that differ by 90°.

11. The nuclear magnetic resonance measurement device as claimed in claim 6, wherein the processor is constructed and arranged to decompose the NMR echo signal into a decay component and a recovery component.

12. The nuclear magnetic resonance measurement device as claimed in claim 11, wherein the parameter of the sample is a longitudinal relaxation time of the sample, and wherein the processor is constructed and arranged to analyze the decay component to obtain a measurement of the longitudinal relaxation time of the sample.

13. The nuclear magnetic resonance measurement device as claimed in claim 6, wherein the processor is constructed and arranged to decompose the NMR echo signal into a direct echo component and a stimulated echo component.

14. The nuclear magnetic resonance measurement device as claimed in claim 13, wherein the parameter of the sample is a diffusion coefficient, and wherein the processor is constructed and arranged to analyze the direct echo component and the stimulated echo component to determine the diffusion coefficient.

15. The nuclear magnetic resonance measurement device as claimed in claim 14, wherein the processor is constructed and arranged to analyze the direct echo component to extract a first amplitude, and to analyze the stimulated echo component to extract a second amplitude of the stimulated echo component; and wherein the processor is configured to determine the diffusion coefficient from a ratio of the first and second amplitudes.

* * * * *